US012496358B2

(12) United States Patent
Schrum et al.

(10) Patent No.: US 12,496,358 B2
(45) **Date of Patent: *Dec. 16, 2025**

(54) MODIFIED NUCLEOSIDES, NUCLEOTIDES, AND NUCLEIC ACIDS, AND USES THEREOF

(71) Applicant: ModernaTX, Inc., Cambridge, MA (US)

(72) Inventors: Jason P. Schrum, Philadelphia, PA (US); Suhaib Siddiqi, Burlington, MA (US); Kenechi Ejebe, New York, NY (US)

(73) Assignee: ModernaTX, Inc., Cambridge, MA (US)

( * ) Notice: Subject to any disclaimer, the term of this patent is extended or adjusted under 35 U.S.C. 154(b) by 399 days.

This patent is subject to a terminal disclaimer.

(21) Appl. No.: 18/045,805

(22) Filed: Oct. 11, 2022

(65) Prior Publication Data

US 2024/0033379 A1 Feb. 1, 2024

Related U.S. Application Data

(60) Continuation of application No. 16/047,574, filed on Jul. 27, 2018, now abandoned, which is a continuation of application No. 15/493,829, filed on Apr. 21, 2017, now Pat. No. 10,064,959, which is a division of application No. 15/143,364, filed on Apr. 29, 2016, now Pat. No. 9,657,295, which is a continuation of application No. 13/739,212, filed on Jan. 11, 2013, now Pat. No. 9,334,328, which is a continuation of application No. 13/481,127, filed on May 25, 2012, now abandoned, which is a continuation of application No. 13/251,840, filed on Oct. 3, 2011, now abandoned.

(60) Provisional application No. 61/404,413, filed on Oct. 1, 2010.

(51) Int. Cl.

| | |
|---|---|
| ***C12N 15/11*** | (2006.01) |
| ***A61K 48/00*** | (2006.01) |
| ***C07H 19/10*** | (2006.01) |
| ***C07H 21/02*** | (2006.01) |
| ***C07K 16/00*** | (2006.01) |
| ***C07K 16/28*** | (2006.01) |
| ***C12N 5/071*** | (2010.01) |
| ***C12N 15/10*** | (2006.01) |
| ***C12N 15/113*** | (2010.01) |
| ***C12N 15/67*** | (2006.01) |
| ***C12P 21/00*** | (2006.01) |
| ***G01N 33/559*** | (2006.01) |

(52) U.S. Cl.

CPC ......... *A61K 48/0066* (2013.01); *C07H 19/10* (2013.01); *C07H 21/02* (2013.01); *C07K 16/00* (2013.01); *C07K 16/2887* (2013.01); *C12N 5/0602* (2013.01); *C12N 15/102* (2013.01); *C12N 15/11* (2013.01); *C12N 15/1136* (2013.01); *C12N 15/1138* (2013.01); *C12N 15/67* (2013.01); *C12P 21/00* (2013.01); *G01N 33/559* (2013.01); *C07K 2317/24* (2013.01); *C12N 2310/3341* (2013.01); *C12N 2310/335* (2013.01)

(58) Field of Classification Search

CPC .... A61K 48/0066; C07H 19/10; C07K 16/00; C07K 16/2887; C07K 2317/24; C12N 15/102; C12N 15/11; C12N 5/0602; C12P 21/00; G01N 33/559

See application file for complete search history.

(56) References Cited

U.S. PATENT DOCUMENTS

| | | | | |
|---|---|---|---|---|
| 9,334,328 | B2 * | 5/2016 | Schrum | C12P 21/00 |
| 10,064,959 | B2 * | 9/2018 | Schrum | C12P 21/00 |
| 11,911,474 | B2 | 2/2024 | De Fougerolles et al. | |
| 12,364,763 | B2 | 7/2025 | De Fougerolles et al. | |
| 2024/0252645 | A1 | 8/2024 | De Fougerolles et al. | |
| 2025/0057954 | A1 | 2/2025 | De Fougerolles et al. | |
| 2025/0064937 | A1 | 2/2025 | De Fougerolles et al. | |
| 2025/0090666 | A1 | 3/2025 | De Fougerolles et al. | |

FOREIGN PATENT DOCUMENTS

| | | | |
|---|---|---|---|
| EP | 3112467 | A1 | 1/2017 |
| EP | 3287525 | A1 | 2/2018 |
| EP | 3611266 | B1 | 11/2022 |
| WO | WO-2005/039551 | A2 | 5/2005 |
| WO | WO-2007024708 | A2 | 3/2007 |
| WO | WO-2007/041774 | A1 | 4/2007 |
| WO | WO-2008052770 | A2 | 5/2008 |

OTHER PUBLICATIONS

U.S. Appl. No. 61/404,413, Afeyan et al.
U.S. Appl. No. 61/470,451, Afeyan et al.
Alexopoulou et al., "Recognition of double-stranded RNA and activation of NF-κB by Toll-like receptor 3," Nature 413:732-38 (2001).
Berg et al., Chapter 4: DNA, RNA, and the Flow of Genetic Information. *Biochemistry, Sixth Edition*. W.H. Freeman and Company, 107, 119, 126 (2007) (5 pages).
Berry & Associates, 2009 Product Catalog, downloaded Sep. 3, 2024 (288 pages).
Charette et al., "Pseudouridine in RNA: What, Where, How, and Why," IUBMB Life 49(5);341-51 (2000).
Conrad et al., "Enzymatic synthesis of 2'-modified nucleic acids: identification of important phosphate and ribose moieties in RNase P substrates," Nucleic Acids Res 23(11):1845-53 (1995).
De Wet et al., "Firefly Luciferase Gene: Structure and Expression in Mammalian Cells," Mol Cell Bio 7(2):725-37 (1987).
Diebold et al., "Innate antiviral responses by means of TLR7-mediated recognition of single-stranded RNA," Science. 303(5663): 1529-31 (2004).
Feng et al., "MDA5 Detects the Double-Stranded RNA Replicative Form in Picornavirus-Infected Cells," Cell Rep 2(5);1187-96 (Nov. 2012).

(Continued)

*Primary Examiner* — Jezia Riley
(74) *Attorney, Agent, or Firm* — Clark & Elbing LLP

(57) ABSTRACT

The present disclosure provides modified nucleosides, nucleotides, and nucleic acids, and methods of using thereof.

1 Claim, 24 Drawing Sheets

Specification includes a Sequence Listing.

(56) References Cited

OTHER PUBLICATIONS

Gallie et al., "Heat Shock Disrupts Cap and Poly(A) Tail Function during Translation and Increases mRNA Stability of Introduced Reporter mRNA," Plant Physiol 108(4):1703-13 (1995).
Gallie et al., "Post-transcriptional regulation in higher eukaryotes: The role of the reporter gene in controlling expression," Mol Gen Genet 228:258-64 (1991).
Hames et al., Processing of Eukaryotic Pre-mRNA. *Biochemistry, Third Edition*. Taylor & Francis Group, 220-7 (2005) (10 pages).
Heil et al., "Species-Specific Recognition of Single-Stranded RNA via Toll-like Receptor 7 and 8." *Science* 303(5663):1526-9 (with supplementary material) (2004) (8 pages).
Helm, M., "Post-transcriptional nucleotide modification and alternative folding of RNA," Nucleic Acids Res 34(2):721-33 (2006).
Ivanov et al., "RNA Synthesis by T7 Rna Polymerase Supported Primer Extension," J Mol Biol 38(5):674-9 (2004).
Karikó et al., "Incorporation of pseudouridine into mRNA yields superior nonimmunogenic vector with increased translational capacity and biological stability," Mol Ther. 16(11):1833-40 (2008).
Karikó et al., Supplementary material for "Incorporation of Pseudouridine in mRNA Yields Superior Nonimmunogenic Vector with Increased Translational Capacity and Biological Stability," Mol Ther 16(11):1833-40 (2008) (4 pages).
Kozak, M., "Regulation of translation via mRNA structure in prokaryotes and eukaryotes," Gene 361:13-37 (2005).
Limbach et al., "Summary: the modifiers nucleosides of RNA," Nucleic Acids Res. 22(12):2183-96 (1994).
Matsumoto et al., "Establishment of a monoclonal antibody against human Toll-like receptor 3 that blocks double-stranded RNA-mediated signaling," Biochem Biophys Res Commun 293(5):1364-9 (2002).
McCloskey et al., "Post-transcriptional modification in archaeal tRNAs: identities and phylogenetic relations of nucleotides from mesophilic and hyperthermophilic *Methanococcales*," Nucleic Acids Res 29(22):4699-706 (2001).
Milligan et al., Synthesis of Small RNAs Using T7 Rna Polymerase. *Methods in Enzymology*, vol. 180. Academic Press, Inc., 51-62 (1989).
MMESSAGE mMACHINE Kit Product Manual, Ambion/Invitrogen. Last revised Jan. 4, 2007 (34 pages).
Motorin et al., "Appendix 1: Chemical Structures and Classification of Posttranscriptionally Modified Nucleosides in RNA," *Modification and Editing of RNA*. ASM Press, 543-9 (1998).
Newby et al., "Investigation of Overhauser effects between pseudouridine and water protons in RNA helices," Proc Natl Acad Sci 99(20):12697-702 (2002) (6 pages).
Oliva et al., "Accurate energies of hydrogen bonded nucleic acid base pairs and triplets in tRNA tertiary interactions," Nucleic Acids Res 34(3):865-79 (2006).
Pascolo, Chapter 3: Vaccination With Messenger RNA. *Methods in Molecular Medicine, vol. 127: DNA Vaccines: Methods and Protocols: Second Edition*. Saltzman et al., Humana Press Inc., 23-40 (2006).
Pascolo, S. Vaccination with messenger RNA (mRNA). Handb Exp Pharmacol. 2008; 183:221-235.
Pelletier et al., "The involvement of mRNA secondary structure in protein synthesis," Biochem Cell Biol 65(6):576-81 (1987).
R&D Systems, ELISA Catalog & Reference Guide 2007, downloaded Sep. 3, 2024 (60 pages).
Rehm et al., 5b Mutations, *Biotechnology, A Comprehensive Treatise in 8 Volumes, vol. 1: Microbial Fundamentals*. H.J. Rehm and G. Reed, 282 (1981) (3 pages).
Song et al., "$m^7$GpppG cap dependence for efficient translation of *Drosophila* 70-kDa heat-shock-protein (Hsp70) mRNA," Eur J Biochem 232(3):778-88 (1995).
Sprinzl et al., "Compilation of tRNA sequences and sequences of tRNA genes," Nucleic Acids Res 26(1):148-53 (1998).
Williams et al., "Messenger Nucleic Acids." *The Encyclopedia of Biochemistry*. Reinhold Publishing Corporation, 513, 692 (1967) (4 pages).
Wurm et al., "The ribosome assembly factor Nep1 responsible for Bowen-Conradi syndrome is a pseudouridine-N1-specific methyltransferase," Nucleic Acids Res 38(7):2387-98 (Apr. 2010).
Zhou et al., "Synthesis of Functional mRNA in Mammalian Cells by Bacteriophage T3 RNA Polymerase," Mol Cell Biol 10(9):4529-37 (1990).

* cited by examiner

FIG. 5A

| Hu-G-CSF modRNA | Keratinocyte well hu-G-CSF (ng/ml) | KG-1 well hu-G-CSF (ng/ml) |
|---|---|---|
| Vehicle | 0.0177 | 0.0189 |
| Scramble | 0.6217 | 0.0086 |
| Chem 7 | ≥5 | ≥5 |
| Chem 20 | ≥5 | ≥5 |
| Chem 46 | ≥5 | ≥5 |
| Chem 53 | ≥5 | ≥5 |

| Hu-G-CSF modRNA | Keratinocyte well hu-G-CSF (ng/ml) | Kasumi-1 well hu-G-CSF (ng/ml) |
|---|---|---|
| Vehicle | 0.0434 | 0.0256 |
| Scramble | 0.0655 | 0.3317 |
| Chem 6 | ≥5 | ≥5 |
| Chem 7 | ≥5 | ≥5 |
| Chem 20 | ≥5 | ≥5 |
| Chem 37 | ≥5 | ≥5 |
| Chem 46 | ≥5 | ≥5 |
| Chem 48 | ≥5 | ≥5 |
| Chem 49 | ≥5 | ≥5 |
| Chem 53 | ≥5 | ≥5 |

| # | Sample ID | User name | Date and Time | Nucleic Acid Conc. | Unit | A260 | A280 | 260/280 | 260/230 | Sample Type | Factor |
|---|---|---|---|---|---|---|---|---|---|---|---|
| 21 | UNMODIFIED NTP's | lab | 8/15/2011 11:45:55 AM | 1599.6 | ng/µl | 39.990 | 17.841 | 2.24 | 2.41 | RNA | 40.00 |

| # | Sample ID | User name | Date and Time | Nucleic Acid Conc. | Unit | A260 | A280 | 260/280 | 260/230 | Sample Type | Factor |
|---|---|---|---|---|---|---|---|---|---|---|---|
| 2 | N1-methyl-A | lab | 8/16/2011 11:35:49 AM | 20.1 | ng/μl | 0.503 | 0.288 | 1.75 | 0.92 | RNA | 40.00 |

| Sample ID | User name | Date and Time | Nucleic Acid Conc. | Unit | A260 | A280 | 260/280 | 260/230 | Sample Type | Factor |
|---|---|---|---|---|---|---|---|---|---|---|
| N6-methyl-2-amino-Purine | lab | 8/16/2011 11:38:29 AM | 1112.4 | ng/µl | 27.811 | 17.607 | 1.58 | 1.40 | RNA | 40.00 |

| # | Sample ID | User name | Date and Time | Nucleic Acid Conc. | Unit | A260 | A280 | 260/280 | 260/230 | Sample Type | Factor |
|---|---|---|---|---|---|---|---|---|---|---|---|
| 2 | 2-thio-CTP | lab | 8/15/2011 11:26:59 AM | 259.2 | ng/µl | 6.479 | 4.719 | 1.37 | 1.30 | RNA | 40.00 |

| # | Sample ID | User name | Date and Time | Nucleic Acid Conc. | Unit | A260 | A280 | 260/280 | 260/230 | Sample Type | Factor |
|---|---|---|---|---|---|---|---|---|---|---|---|
| 4 | pseudo-iso-CTP | lab | 8/15/2011 11:29:10 AM | 1332.5 | ng/µl | 33.311 | 13.674 | 2.44 | 1.79 | RNA | 40.00 |

| # | Sample ID | User name | Date and Time | Nucleic Acid Conc. | Unit | A260 | A280 | 260/280 | 260/230 | Sample Type | Factor |
|---|---|---|---|---|---|---|---|---|---|---|---|
| 6 | 5-iodo-UTP | lab | 8/15/2011 11:31:06 AM | 1179.4 | ng/µl | 29.486 | 16.726 | 1.76 | 1.10 | RNA | 40.00 |

| # | Sample ID | User name | Date and Time | Nucleic Acid Conc. | Unit | A260 | A280 | 260/280 | 260/230 | Sample Type | Factor |
|---|---|---|---|---|---|---|---|---|---|---|---|
| 7 | N1 methyl-pseudoUTP | lab | 8/15/2011 11:32:15 AM | 1408.1 | ng/µl | 35.202 | 18.565 | 1.90 | 2.17 | RNA | 40.00 |

| # | Sample ID | User name | Date and Time | Nucleic Acid Conc. | Unit | A260 | A280 | 260/280 | 260/230 | Sample Type | Factor |
|---|---|---|---|---|---|---|---|---|---|---|---|
| 15 | ITP | lab | 8/15/2011 11:40:05 AM | 225.1 | ng/µl | 5.628 | 5.781 | 0.97 | 1.05 | RNA | 40.00 |

| # | Sample ID | User name | Date and Time | Nucleic Acid Conc. | Unit | A260 | A280 | 260/280 | 260/230 | Sample Type | Factor |
|---|---|---|---|---|---|---|---|---|---|---|---|
| 18 | N1-methyl-GTP | lab | 8/15/2011 11:43:10 AM | 161.5 | ng/μl | 4.036 | 2.917 | 1.38 | 0.67 | RNA | 40.00 |

| Sample ID | User name | Date and Time | Nucleic Acid Conc. | Unit | A260 | A280 | 260/280 | 260/230 | Sample Type | Factor |
|---|---|---|---|---|---|---|---|---|---|---|
| pseudo-iso-CTP/N1-methyl-pseudo-UTP | lab | 9/2/2011 3:48:37 PM | 1268.3 | ng/µl | 31.707 | 17.208 | 1.84 | 1.64 | RNA | 40.00 |

| Sample ID | User name | Date and Time | Nucleic Acid Conc. | Unit | A260 | A280 | 260/280 | 260/230 | Sample Type | Factor |
|---|---|---|---|---|---|---|---|---|---|---|
| Pyr-CTP | lab | 9/12/2011 2:03:00 PM | 1103.7 | ng/µl | 27.592 | 11.101 | 2.49 | 1.14 | RNA | 40.00 |

| Sample ID | User name | Date and Time | Nucleic Acid Conc. | Unit | A260 | A280 | 260/280 | 260/230 | Sample Type | Factor |
|---|---|---|---|---|---|---|---|---|---|---|
| 5-Me-CTP/N1-Me-pseudo-UTP | lab | 9/12/2011 3:47:12 PM | 1094.3 | ng/μl | 27.358 | 16.135 | 1.70 | 2.11 | RNA | 40.00 |

MODIFIED NUCLEOSIDES, NUCLEOTIDES, AND NUCLEIC ACIDS, AND USES THEREOF

CLAIM OF PRIORITY

This application is a continuation application of U.S. application Ser. No. 16/047,574, abandoned, which is a continuation application of U.S. application Ser. No. 15/493,829, filed on Apr. 21, 2017, issued as U.S. Pat. No. 10,064,959 on Sep. 4, 2018, which is a divisional application of U.S. application Ser. No. 15/143,364, filed on Apr. 29, 2016, issued as U.S. Pat. No. 9,657,295 on May 23, 2017, which is a continuation of U.S. application Ser. No. 13/739,212, filed on Jan. 11, 2013, issued as U.S. Pat. No. 9,334,328 on May 10, 2016, which is a continuation of U.S. application Ser. No. 13/481,127, filed on May 25, 2012, abandoned, which is a continuation of U.S. application Ser. No. 13/251,840, filed on Oct. 3, 2011, abandoned, which claims priority to and the benefit of U.S. Provisional Application Ser. No. 61/404,413, filed on Oct. 1, 2010, the contents of each of which are incorporated herein by reference in their entireties.

INCORPORATION BY REFERENCE OF SEQUENCE LISTING

The instant application contains a Sequence Listing which has been submitted electronically in XML format and is hereby incorporated by reference in its entirety. Said XML copy, created on Oct. 3, 2022, is named 50858-121008_Sequence_Listing_10_3_22. xml and is 12,288 bytes in size.

BACKGROUND

Naturally occurring RNAs are synthesized from four basic ribonucleotides: ATP, CTP, UTP and GTP, but may contain post-transcriptionally modified nucleotides. Further, approximately one hundred different nucleoside modifications have been identified in RNA (Rozenski, J, Crain, P, and McCloskey, J. (1999). The RNA Modification Database: 1999 update. Nucl Acids Res 27: 196-197). The role of nucleoside modifications on the immuno-stimulatory potential, stability, and on the translation efficiency of RNA, and the consequent benefits to this for enhancing protein expression and producing therapeutics however, is unclear.

There are multiple problems with prior methodologies of effecting protein expression. For example, heterologous deoxyribonucleic acid (DNA) introduced into a cell can be inherited by daughter cells (whether or not the heterologous DNA has integrated into the chromosome) or by offspring. Introduced DNA can integrate into host cell genomic DNA at some frequency, resulting in alterations and/or damage to the host cell genomic DNA. In addition, multiple steps must occur before a protein is made. Once inside the cell, DNA must be transported into the nucleus where it is transcribed into RNA. The RNA transcribed from DNA must then enter the cytoplasm where it is translated into protein. This need for multiple processing steps creates lag times before the generation of a protein of interest. Further, it is difficult to obtain DNA expression in cells; frequently DNA enters cells but is not expressed or not expressed at reasonable rates or concentrations. This can be a particular problem when DNA is introduced into cells such as primary cells or modified cell lines.

There is a need in the art for biological modalities to address the modulation of intracellular translation of nucleic acids.

SUMMARY

The present disclosure provides, inter alia, modified nucleosides, modified nucleotides, and modified nucleic acids which can exhibit a reduced innate immune response when introduced into a population of cells, both in vivo and ex vivo. Further, these modified nucleosides, modified nucleotides, and modified nucleic acids described herein can disrupt binding of a major groove interacting partner with the nucleic acid. Because of the reduced immunogenicity and the decrease in major groove interactions, these modified nucleosides, modified nucleotides, and modified nucleic acids can be more efficient during protein production than, e.g., unmodified nucleic acids.

Thus, the present disclosure provides compounds comprising nucleotides that can disrupt binding of a major groove binding partner with a nucleic acid, wherein the nucleotide has decreased binding affinity to the major groove binding partner.

The present disclosure further provides compounds having Formula I:

I

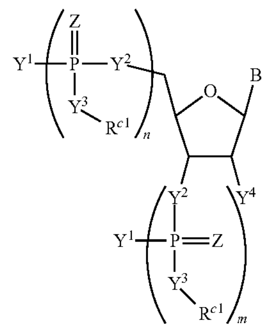

wherein constituent variables are provided herein.

The present disclosure further provides nucleic acid sequences of at least two nucleotides comprising a compound of Formula I-d:

I-d

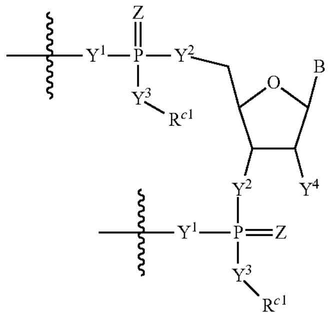

wherein constituent variables are provided herein.

The present disclosure further provides compositions comprising at least one compound of Formula I.

The present disclosure further provides pharmaceutical compositions comprising a compound of Formula I.

The present disclosure further provides methods of preparing nucleic acid sequences of at least two nucleotides of a compound of Formula I-d.

The present disclosure further provides methods of amplifying nucleic acid sequences of at least two nucleotides of a compound of Formula I-d.

The present disclosure further provides kits comprising a compound of Formula I.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF DRAWINGS

FIG. 5A is a table showing results from an Enzyme-linked immunosorbent assay (ELISA) for human-G-CSF secreted from in vitro-transfected Human Keratinocyte cells sampled from individual wells in a co-culture 24-well tissue culture plate 42 hours post-transfection with 750 ng of each indicated hu-G-CSF-encoding modRNA.

DETAILED DESCRIPTION

Figure 1A:
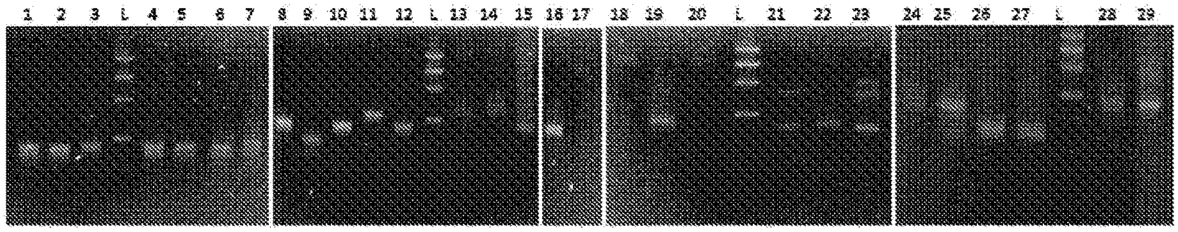
FIGS. 1A and 1B depict images of non-denaturing agarose gels of each in vitro-transcribed modified RNA.

The present disclosure provides, inter alia, modified nucleosides, modified nucleotides, and modified nucleic acids that exhibit a reduced innate immune response when introduced into a population of cells. The modified nucleosides, modified nucleotides, and modified nucleic acids can be chemically modified on the major groove face, thereby disrupting major groove binding partner interactions, which cause innate immune responses.

In general, exogenous unmodified nucleic acids, particularly viral nucleic acids, introduced into cells induce an innate immune response, resulting in cytokine and interferon (IFN) production and cell death. However, it is of great interest for therapeutics, diagnostics, reagents and for biological assays to deliver a nucleic acid, e.g., a ribonucleic acid (RNA) inside a cell, either in vivo or ex vivo, such as to cause intracellular translation of the nucleic acid and production of the encoded protein. Of particular importance is the delivery and function of a non-integrative nucleic acid, as nucleic acids characterized by integration into a target cell are generally imprecise in their expression levels, deleteriously transferable to progeny and neighbor cells, and suffer from the substantial risk of causing mutation. Provided herein in part are nucleic acids encoding useful polypeptides capable of modulating a cell's function and/or activity, and methods of making and using these nucleic acids and polypeptides. As described herein, these nucleic acids are capable of reducing the innate immune activity of a population of cells into which they are introduced, thus increasing the efficiency of protein production in that cell population. Further, one or more additional advantageous activities and/or properties of the nucleic acids and proteins of the present disclosure are described.

Further, the modified nucleosides, modified nucleotides, and modified nucleic acids described herein can be modified on the major groove face. These major groove modifications can allow for alterations, e.g. a decrease, in the interaction of the modified nucleosides, modified nucleotides, and modified nucleic acids with a binding groove partner.

Accordingly, in a first aspect, the present disclosure provides compounds comprising a nucleotide that can disrupts binding of a major groove interacting, e.g. binding, partner with a nucleic acid, wherein the nucleotide has decreased binding affinity to major groove interacting, e.g. binding, partners. In another aspect, the present disclosure provides compounds comprising a nucleotide that contains chemical modifications, wherein the nucleotide can have altered binding to major groove interacting, e.g. binding, partners.

In some embodiments, the chemical modifications are located on the major groove face of the nucleobase, and wherein the chemical modifications can include replacing or substituting an atom of a pyrimidine nucleobase with an amine, an SH, an alkyl (e.g., methyl or ethyl), or a halo (e.g., chloro or fluoro).

In some embodiments, the chemical modifications can be located on the major groove face of the nucleobase, and wherein the chemical modification can include replacing or substituting an atom of a pyrimidine nucleobase with an amine, an SH, a methyl or ethyl, or a chloro or fluoro.

In some embodiments, the chemical modifications can be located on the sugar moiety of the nucleotide.

In some embodiments, the chemical modifications can be located on the phosphate backbone of the nucleotide. In some embodiments, the chemical modifications can alter the electrochemistry on the major groove face of the nucleotide.

In another aspect, the present disclosure provides nucleotides that contain chemical modifications, wherein the nucleotide reduces the cellular innate immune response, as compared to the cellular innate immune induced by a corresponding unmodified nucleic acid.

In another aspect, the present disclosure provides nucleic acid sequences comprising at least two nucleotides, the nucleic acid sequence comprising a nucleotide that disrupts binding of a major groove interacting partner with the nucleic acid sequence, wherein the nucleotide has decreased binding affinity to the major groove binding partner.

In another aspect, the present disclosure provides compositions comprising a compound as described herein.

In some embodiments, the composition is a reaction mixture.

In some embodiments, the composition is a pharmaceutical composition.

In some embodiments, the composition is a cell culture.

In some embodiments, the compositions further comprise an RNA polymerase and a cDNA template.

In some embodiments, the compositions further comprise a nucleotide selected from the group consisting of adenosine, cytosine, guanosine, and uracil.

In a further aspect, the present disclosure provides for methods of synthesizing a pharmaceutical nucleic acid, comprising providing a complementary deoxyribonucleic acid (cDNA) that encodes a pharmaceutical protein of interest; selecting a nucleotide that is known to disrupt a binding of a major groove binding partner with a nucleic acid, wherein the nucleotide has decreased binding affinity to the major groove binding partner; and contacting the provided cDNA and the selected nucleotide with an RNA polymerase, under conditions such that the pharmaceutical nucleic acid is synthesized.

In some embodiments, the pharmaceutical nucleic acid is a ribonucleic acid (RNA).

In a further aspect, the present disclosure provides for methods of making a pharmaceutical formulation comprising a physiologically active secreted protein, comprising transfecting a first population of human cells with a pharmaceutical nucleic acid made by the methods described herein, wherein the secreted protein is active upon a second population of human cells.

In some embodiments, the secreted protein is capable of interacting, e.g. binding, with a receptor on the surface of at least one cell present in the second population.

In some embodiments, the secreted protein is Granulocyte-Colony Stimulating Factor (G-CSF).

In some embodiments, the second population contains myeloblast cells that express the G-CSF receptor.

In a further aspect, the present disclosure provides for methods of making a pharmaceutical formulation comprising human cells comprising a physiologically active secreted protein, comprising transfecting a first population of human cells with a pharmaceutical nucleic acid made by the methods described herein, wherein the secreted protein is active upon a second population of human cells.

Definitions

At various places in the present specification, substituents of compounds of the present disclosure are disclosed in groups or in ranges. It is specifically intended that the present disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further intended that the compounds of the present disclosure are stable. As used herein "stable" refers to a compound that is sufficiently robust to survive isolation to a useful degree of purity from a reaction mixture, and preferably capable of formulation into an efficacious therapeutic agent.

It is further appreciated that certain features of the present disclosure, which are, for clarity, described in the context of separate embodiments, can also be provided in combination in a single embodiment. Conversely, various features of the present disclosure which are, for brevity, described in the context of a single embodiment, can also be provided separately or in any suitable subcombination.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 12, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, and the like. As used herein, "alkoxy" refers to an —O-alkyl group. Example alkoxy groups include methoxy, ethoxy, propoxy (e.g., n-propoxy and isopropoxy), t-butoxy, and the like.

As used herein, "alkynyl" refers to an alkyl group having one or more triple carbon-carbon bonds. Example alkynyl groups include ethynyl, propynyl, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "halo" or "halogen" includes fluoro, chloro, bromo, and iodo. As used herein, "therapeutic agent" refers to any agent that, when administered to a subject, has a therapeutic, diagnostic, and/or prophylactic effect and/or elicits a desired biological and/or pharmacological effect.

As used herein, "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

As used herein, "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions.

As used herein, "biologically active" refers to a characteristic of any substance that has activity in a biological system and/or organism. For instance, a substance that, when administered to an organism, has a biological effect on that organism, is considered to be biologically active. In particular embodiments, where a nucleic acid is biologically active, a portion of that nucleic acid that shares at least one biological activity of the whole nucleic acid is typically referred to as a "biologically active" portion.

As used herein, "conserved" refers to nucleotides or amino acid residues of a polynucleotide sequence or amino acid sequence, respectively, that are those that occur unaltered in the same position of two or more related sequences being compared. Nucleotides or amino acids that are relatively conserved are those that are conserved amongst more related sequences than nucleotides or amino acids appearing elsewhere in the sequences. In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another.

As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

As used herein, a "functional" biological molecule is a biological molecule in a form in which it exhibits a property and/or activity by which it is characterized.

As used herein, "in vitro" refers to events that occur in an artificial environment, e.g., in a test tube or reaction vessel, in cell culture, in a Petri dish, etc., rather than within an organism (e.g., animal, plant, or microbe).

As used herein, "in vivo" refers to events that occur within an organism (e.g., animal, plant, or microbe).

As used herein, "isolated" refers to a substance or entity that has been (1) separated from at least some of the components with which it was associated when initially produced (whether in nature or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

As used herein, "subject" or "patient" refers to any organism to which a composition in accordance with the present disclosure may be administered, e.g., for experimental, diagnostic, prophylactic, and/or therapeutic purposes. Typical subjects include animals (e.g., mammals such as mice, rats, rabbits, non-human primates, and humans) and/or plants.

As used herein, "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

An individual who is "suffering from" a disease, disorder, and/or condition has been diagnosed with or displays one or more symptoms of a disease, disorder, and/or condition.

An individual who is "susceptible to" a disease, disorder, and/or condition has not been diagnosed with and/or may not exhibit symptoms of the disease, disorder, and/or condition. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

As used herein, "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to a disease, disorder, and/or condition, to treat, improve symptoms of, diagnose, prevent, and/or delay the onset of the disease, disorder, and/or condition.

As used herein, "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors may regulate transcription of a target gene alone or in a complex with other molecules.

As used herein, "treating" refers to partially or completely alleviating, ameliorating, improving, relieving, delaying onset of, inhibiting progression of, reducing severity of, and/or reducing incidence of one or more symptoms or features of a particular disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. In some embodiments, treatment comprises delivery of a protein associated with a therapeutically active nucleic acid to a subject in need thereof.

As used herein, "unmodified" refers to a nucleic acid prior to being modified, e.g. adenosine, guanosine, cytosine, thymidine, and uracil, or a naturally occurring amino acid. The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Compounds of the present disclosure also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the present disclosure can also include all isotopes of atoms occurring in the intermediates or final compounds. Isotopes include those atoms having the same atomic number but different mass numbers. For example, isotopes of hydrogen include tritium and deuterium.

The term "compound," as used herein, is meant to include all stereoisomers, geometric isomers, tautomers, and isotopes of the structures depicted.

In some embodiments, the compounds of the present disclosure are substantially isolated. By "substantially isolated" is meant that the compound is at least partially or substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof. Methods for isolating compounds and their salts are routine in the art.

The compounds of the present disclosure, and salts thereof, can also be prepared in combination with solvent or water molecules to form solvates and hydrates by routine methods.

The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17 th ed., Mack Publishing Company, Easton, Pa., 1985, p. 1418 and *Journal of Pharmaceutical Science,* 66, 2 (1977), each of which is incorporated herein by reference in its entirety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present disclosure also includes prodrugs of the compounds described herein. As used herein, "prodrugs" refer to any carriers, typically covalently bonded, which release the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively.

Examples of prodrugs include, but are not limited to, acetate, formate and benzoate derivatives of alcohol and amine functional groups in the compounds of the present disclosure. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entirety.

Modified Nucleosides and Nucleotides

The present disclosure provides for modified nucleosides and nucleotides. As described herein "nucleoside" is defined as a compound containing a five-carbon sugar molecule (a pentose or ribose) or derivative thereof, and an organic base, purine or pyrimidine, or a derivative thereof. As described herein, "nucleotide" is defined as a nucleoside consisting of a phosphate group. The nucleosides and nucleotides described herein are generally chemically modified on the major groove face. In some embodiments, the major groove chemical modifications can include an amino group, a thiol group, an alkyl group, or a halo group.

Table 1 below identifies the chemical faces of each canonical nucleotide. Circles identify the atoms comprising the respective chemical regions.

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine,

| | | Major Groove Face | Minor Groove Face | Watson-Crick Base-pairing Face |
|---|---|---|---|---|
| Pyrimidines | Cytidine: | 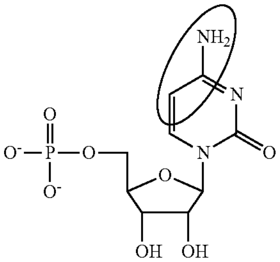 [SMILES: Nc1ccn(C2OC(COP(=O)([O-])[O-])C(O)C2O)c(=O)n1] | 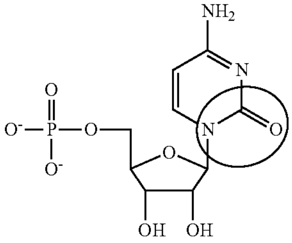 [SMILES: Nc1ccn(C2OC(COP(=O)([O-])[O-])C(O)C2O)c(=O)n1] | 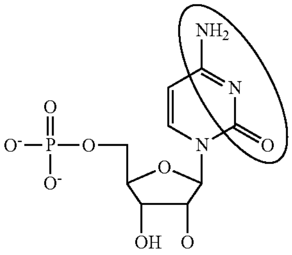 [SMILES: Nc1ccn(C2OC(COP(=O)([O-])[O-])C(O)C2O)c(=O)n1] |
| | Uridine: | 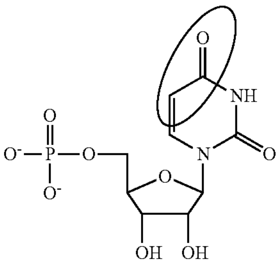 [SMILES: O=c1ccn(C2OC(COP(=O)([O-])[O-])C(O)C2O)c(=O)[nH]1] | 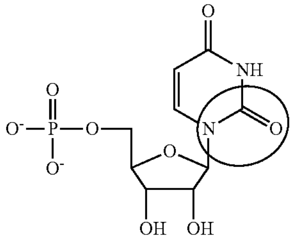 [SMILES: O=c1ccn(C2OC(COP(=O)([O-])[O-])C(O)C2O)c(=O)[nH]1] | 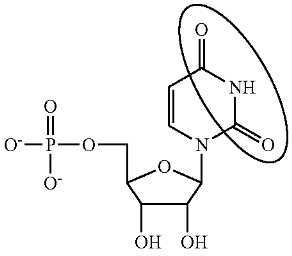 [SMILES: O=c1ccn(C2OC(COP(=O)([O-])[O-])C(O)C2O)c(=O)[nH]1] |
| Purines | Adenosine: | 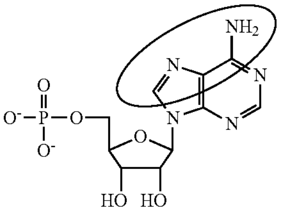 [SMILES: Nc1ncnc2c1ncn2C1OC(COP(=O)([O-])[O-])C(O)C1O] | 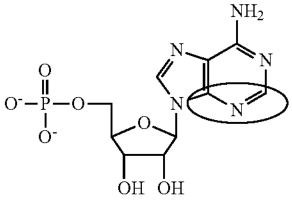 [SMILES: Nc1ncnc2c1ncn2C1OC(COP(=O)([O-])[O-])C(O)C1O] | 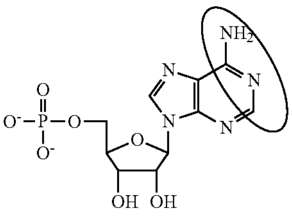 [SMILES: Nc1ncnc2c1ncn2C1OC(COP(=O)([O-])[O-])C(O)C1O] |
| | Guanosine: | 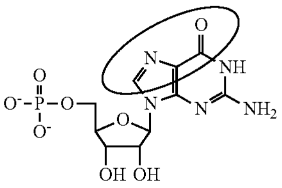 [SMILES: Nc1nc2c(ncn2C2OC(COP(=O)([O-])[O-])C(O)C2O)c(=O)[nH]1] | 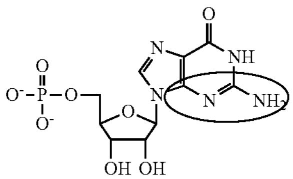 [SMILES: Nc1nc2c(ncn2C2OC(COP(=O)([O-])[O-])C(O)C2O)c(=O)[nH]1] | 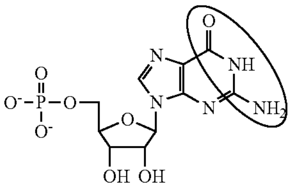 [SMILES: Nc1nc2c(ncn2C2OC(COP(=O)([O-])[O-])C(O)C2O)c(=O)[nH]1] |

2-methoxy-5-methyl-cytidine, 4-methoxy-pseudoisocytidine, and 4-methoxy-1-methyl-pseudoisocytidine.

In other embodiments, modified nucleosides include 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarb amoyladenosine, 2-methylthio-N6-threonyl carbamoyladenosine, N6, N6-dimethyladenosine, 7-methyladenine, 2-methylthio-adenine, and 2-methoxy-adenine.

In some embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2, N2-dimethylguanosine, 8-oxo-guanosine, 7-methyl-8-oxo-guanosine, 1-methyl-6-thio-guanosine, N2-methyl-6-thio-guanosine, and N2, N2-dimethyl-6-thio-guanosine.

In some embodiments, the nucleotide can be modified on the major groove face and can include replacement of the hydrogen on C-5 of uracil with a methyl group or a halo group.

In some embodiments, the nucleoside and nucleotide can be a compound of Formula I:

I

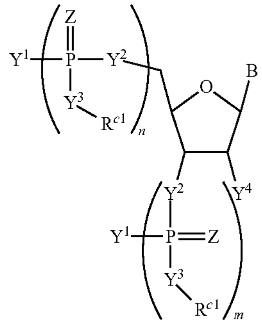

wherein:

Z is O or S;

each of $Y^1$ is independently selected from —$OR^{a1}$, —$NR^{a1}R^{b1}$, and —$SR^{a1}$;

each of $Y^2$ is independently selected from O, $NR^a$, S or a linker comprising an atom selected from the group consisting of C, O, N, and S;

each of Y 3 is independently selected from O and S;

Y 4 is selected from H, —$OR^a$, —$SR^a$, and —$NHR^a$;

n is 0, 1, 2, or 3;

m is 0, 1, 2 or 3;

B is a nucleobase;

$R^a$ is H, $C_{1-20}$ alkyl, $C_{2-20}$ alkenyl, $C_{2-20}$ alkynyl, or $C_{6-20}$ aryl;

$R^{a1}$ and $R^{b1}$ are each independently H or a counterion; and —$Y^3$-$R^{c1}$ is OH or SH at a pH of about 1 or is $O^-$ or $S^-$ at physiological pH;

or —$Y^3$-$R^{c1}$ is $C_{1-20}$ alkoxy, $C_{2-20}$—O-alkenyl, or $C_{1-20}$—O-alkynyl;

wherein when B is an unmodified nucleobase selected from cytosine, guanine, uracil and adenine, then at least one of Z, $Y^1$ or $Y^2$ is not O or OH.

In some embodiments, B is a nucleobase of Formula II-a, II-b, or

II-a

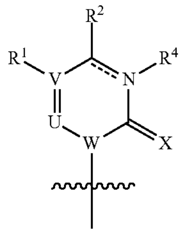

II-b

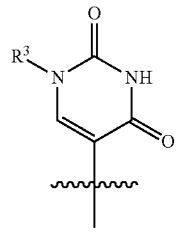

II-c

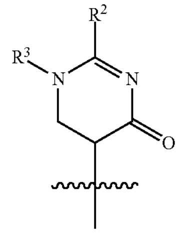

wherein:

denotes a single or double bond;

X is O or S;

U and W are each independently C or N;

V is O, S, C or N;

wherein when V is C then $R^1$ is H, $C_{1-6}$ alkyl, $C_{1-6}$ alkenyl, $C_{1-6}$ alkynyl, halo, or —$OR^c$, wherein $C_{1-20}$ alkyl, $C_{2-20}$ alkenyl, $C_{2-20}$ alkynyl are each optionally substituted with —OH, —$NR^aR^b$, —SH, —C(O)$R^c$, —C(O)$OR^c$, —NHC(O)$R^c$, or —NHC(O)$OR^c$;

and wherein when V is O, S, or N then $R^1$ is absent;

$R^2$ is H, —$OR^c$, —$SR^c$, —$NR^aR^b$, or halo;

or when V is C then $R^1$ and $R^2$ together with the carbon atoms to which they are attached can form a 5- or 6-membered ring optionally substituted with 1-4 substituents selected from halo, —OH, —SH, —$NR^aR^b$, $C_{1-20}$ alkyl, $C_{2-20}$ alkenyl, $C_{2-20}$ alkynyl, $C_{1-20}$ alkoxy, or $C_{1-20}$ thioalkyl;

$R^3$ is H or $C_{1-20}$ alkyl;

$R^4$ is H or $C_{1-20}$ alkyl; wherein when denotes a double bond then $R^4$ is absent, or N—$R^4$, taken together, forms a positively charged N substituted with $C_{1-20}$ alkyl;

$R^a$ and $R^b$ are each independently H, $C_{1-20}$ alkyl, $C_{2-20}$ alkenyl, $C_{2-20}$ alkynyl, or $C_{6-20}$ aryl; and $R^c$ is H, $C_{1-20}$ alkyl, $C_{2-20}$ alkenyl, phenyl, benzyl, a polyethylene glycol group, or an amino-polyethylene glycol group.

In some embodiments, B is a nucleobase of Formula II-a1, II-a2, II-a3, II-a4, or II-a5:

II-a1

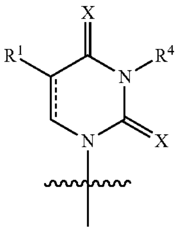

II-a2

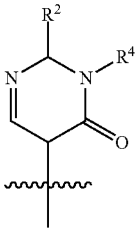

II-a3

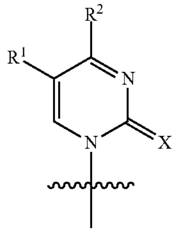

II-a4

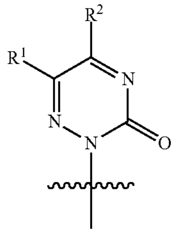

II-a5

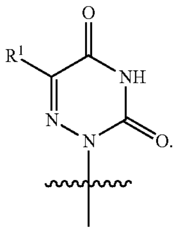

In some embodiments, B is a nucleobase selected from the group consisting of cytosine, guanine, adenine, and uracil.

In some embodiments, B is a pyrimidine or derivative thereof.

In some embodiments the nucleotide is a compound of Formula I-a:

I-a

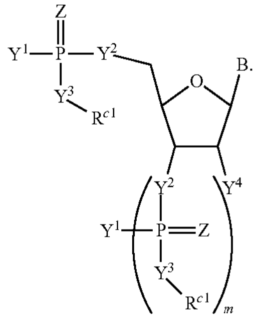

In some embodiments the nucleotide is a compound of Formula I-b:

I-b

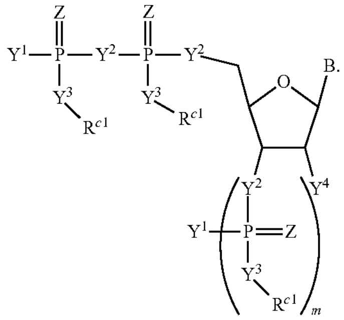

In some embodiments the nucleotide is a compound of Formula I-c:

I-c

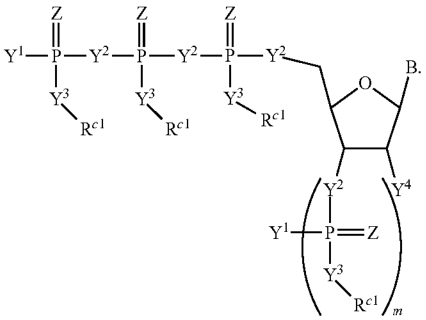

In some embodiments, the nucleotide is selected from the group consisting of:

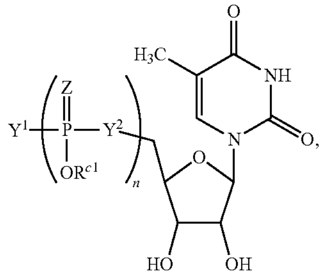

-continued
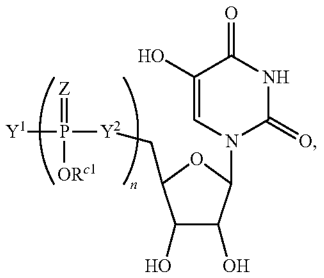
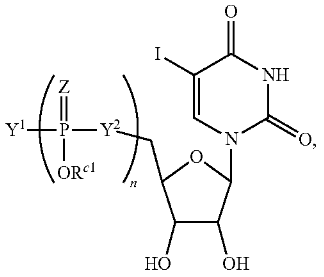
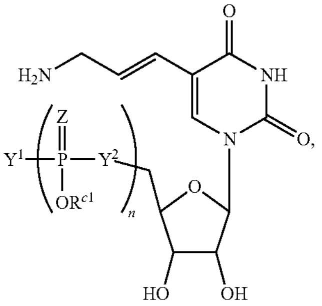
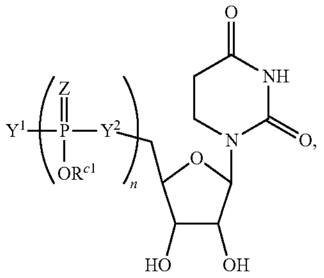
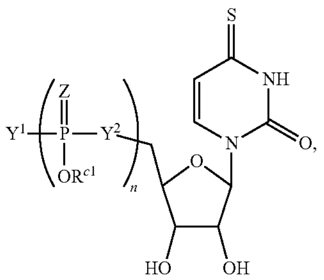
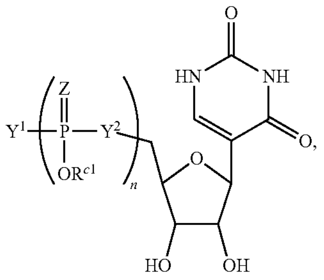
-continued
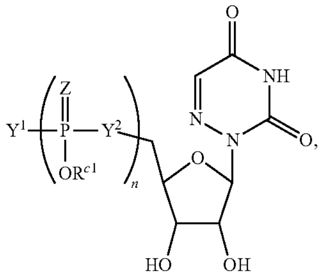
and
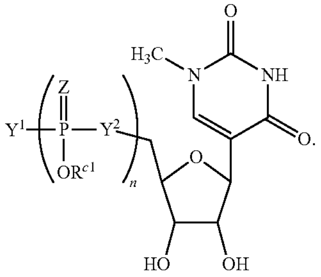
In some embodiments, the nucleotide is selected from the group consisting of:
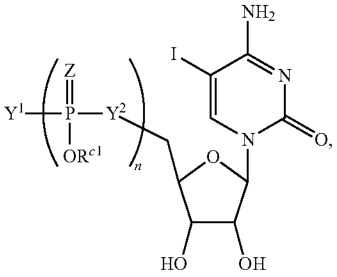
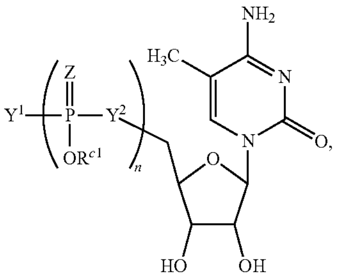
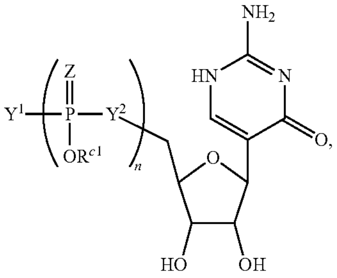

-continued

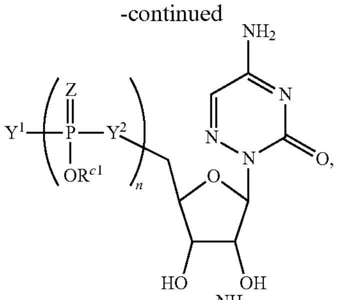

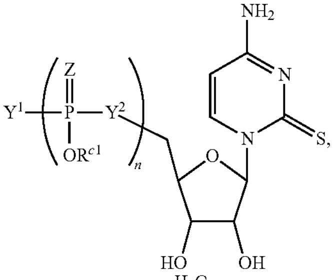

and

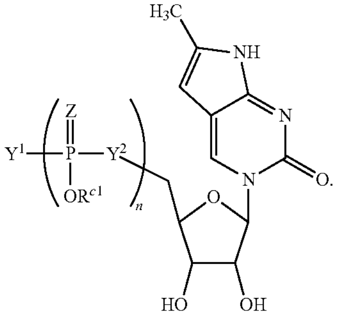

For example, the modified nucleotide can be:

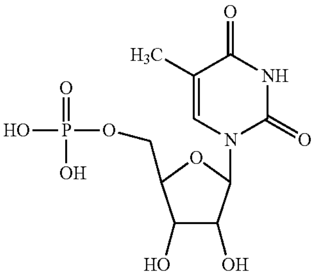

or

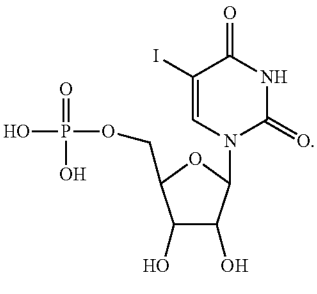

In some embodiments, the major groove chemical modification can include replacement of the C—H group at C-5 with an —NH— group or a —NH($CH_3$)— group. For example, the modified nucleotide can be:

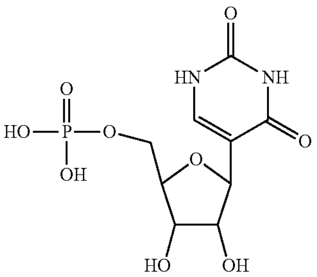

or

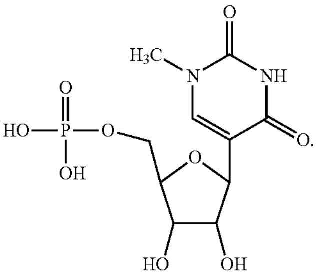

In another embodiment, the major groove chemical modification can include replacement of the hydrogen at C-5 of cytosine with a halo group or a methyl group.

For example, the modified nucleotide can be:

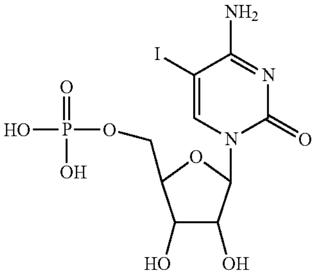

or

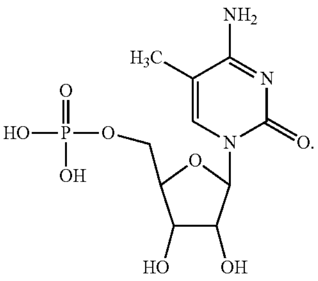

In yet a further embodiment, the major groove chemical modification can include a fused ring that is formed by the $NH_2$ at the C-4 position and the carbon atom at the C-5 position.

For example, the modified nucleotide can be:

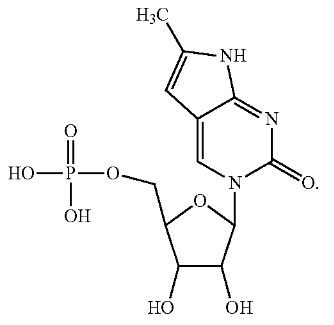 [SMILES: Cc1cc2cn(C3OC(COP(=O)(O)O)C(O)C3O)c(=O)nc2[nH]1]

In some embodiments, a modified nucleotide is 5'-O-(1-Thiophosphate)-Adenosine, 5'-O-(1-Thiophosphate)-Cytidine, 5'-O-(1-Thiophosphate)-Guanosine, 5'-O-(1-Thiophosphate)-Uridine or 5'-O-(1-Thiophosphate)-Pseudouridine.

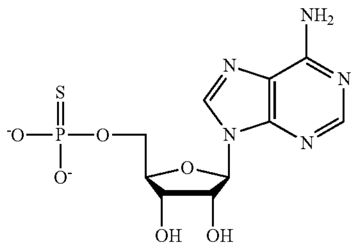

5'-O-(1-Thiophosphate)-Adenosine

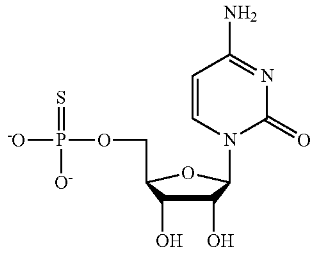

5'-O-(1-Thiophosphate)-Cytidine

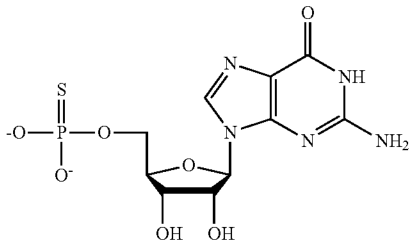

5'-O-(1-Thiophosphate)-Guanosine

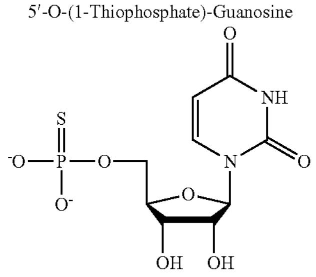

5'-O-(1-Thiophosphate)-Uridine

-continued

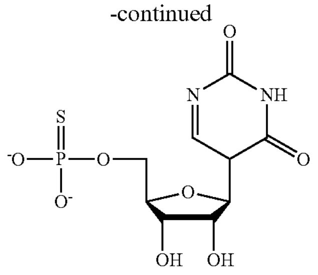

5'-O-(1-Thiophosphate)-Pseudouridine

The α-thio substituted phosphate moiety is provided to confer stability to RNA and DNA polymers through the unnatural phosphorothioate backbone linkages. Phosphorothioate DNA and RNA have increased nuclease resistance and subsequently a longer half-life in a cellular environment. Phosphorothioate linked nucleic acids are expected to also reduce the innate immune response through weaker binding/activation of cellular innate immune molecules.

Further examples of modified nucleotides and modified nucleotide combinations are provided below in Table 2.

TABLE 2

| Modified Nucleotide | Modified Nucleotide Combination |
|---|---|
| 6-aza-cytidine | α-thio-cytidine/5-iodo-uridine |
| 2-thio-cytidine | α-thio-cytidine/N1-methyl-pseudo-uridine |
| α-thio-cytidine | α-thio-cytidine/α-thio-uridine |
| Pseudo-iso-cytidine | α-thio-cytidine/5-methyl-uridine |
| 5-aminoallyl-uridine | α-thio-cytidine/pseudo-uridine |
| 5-iodo-uridine | Pseudo-iso-cytidine/5-iodo-uridine |
| N1-methyl-pseudouridine | Pseudo-iso-cytidine/N1-methyl-pseudo-uridine |
| 5,6-dihydrouridine | Pseudo-iso-cytidine/α-thio-uridine |
| α-thio-uridine | Pseudo-iso-cytidine/5-methyl-uridine |
| 4-thio-uridine | Pseudo-iso-cytidine/Pseudo-uridine |
| 6-aza-uridine | Pyrrolo-cytidine |
| 5-hydroxy-uridine | Pyrrolo-cytidine/5-iodo-uridine |
| Deoxy-thymidine | Pyrrolo-cytidine/N1-methyl-pseudo-uridine |
| Pseudo-uridine | Pyrrolo-cytidine/α-thio-uridine |
| Inosine | Pyrrolo-cytidine/5-methyl-uridine |
| α-thio-guanosine | Pyrrolo-cytidine/Pseudo-uridine |
| 8-oxo-guanosine | 5-methyl-cytidine/5-iodo-uridine |
| O6-methyl-guanosine | 5-methyl-cytidine/N1-methyl-pseudo-uridine |
| 7-deaza-guanosine | 5-methyl-cytidine/α-thio-uridine |
| No modification | 5-methyl-cytidine/5-methyl-uridine |
| N1-methyl-adenosine | 5-methyl-cytidine/Pseudo-uridine |
| 2-amino-6-Chloro-purine | 5-methyl-cytidine |
| N6-methyl-2-amino-purine | 25% Pseudo-iso-cytidine |
| 6-Chloro-purine | 25% N1-methyl-pseudo-uridine |
| N6-methyl-adenosine | 25% N1-Methyl-pseudo-uridine/75%-pseudo-uridine |
| α-thio-adenosine | 5-methyl-uridine |
| 8-azido-adenosine | 5-iodo-cytidine |
| 7-deaza-adenosine | |

Synthesis of Modified Nucleotides

The modified nucleosides and nucleotides disclosed herein can be prepared from readily available starting materials using the following general methods and procedures. It is understood that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures. The processes described herein can be monitored according to any suitable method known in the art. For example, product formation can be monitored by spectroscopic means, such as nuclear magnetic resonance spectroscopy (e.g., $^{1}H$ or $^{13}C$) infrared spectroscopy, spectrophotometry (e.g., UV-visible), or mass spectrometry, or by chromatography such as high performance liquid chromatography (HPLC) or thin layer chromatography.

Preparation of modified nucleosides and nucleotides can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis,* 2d. Ed., Wiley & Sons, 1991, which is incorporated herein by reference in its entirety.

The reactions of the processes described herein can be carried out in suitable solvents, which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. Resolution of racemic mixtures of modified nucleosides and nucleotides can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art.

Exemplary syntheses of modified nucleotides are provided below in Schemes 1 and 2.

Scheme 1

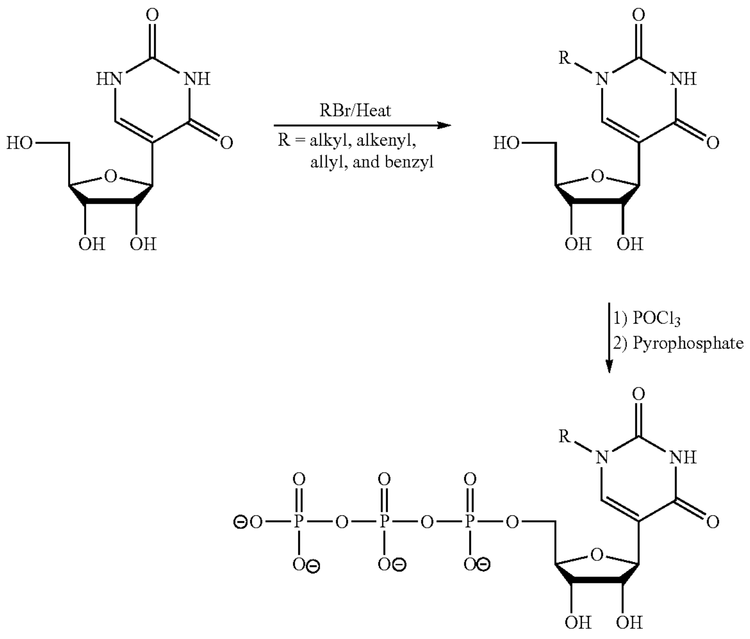

Scheme 2

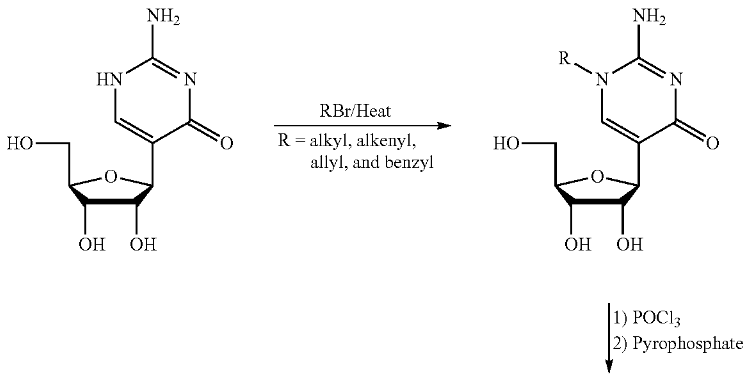

-continued

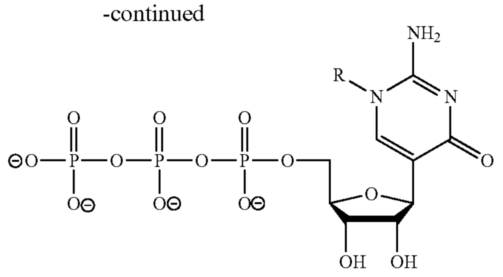

Modified nucleosides and nucleotides can also be prepared according to the synthetic methods described in Ogata et al. *Journal of Organic Chemistry* 74:2585-2588, 2009; Purmal et al. *Nucleic Acids Research* 22(1): 72-78, 1994; Fukuhara et al. *Biochemistry* 1(4): 563-568, 1962; and Xu et al. *Tetrahedron* 48(9): 1729-1740, 1992, each of which are incorporated by reference in their entirety.

Modified Nucleic Acids

The present disclosure provides nucleic acids, including RNAs such as mRNAs that contain one or more modified nucleosides (termed "modified nucleic acids") or nucleotides as described herein, which have useful properties including the significant decrease or lack of a substantial induction of the innate immune response of a cell into which the mRNA is introduced, or the suppression thereof. Because these modified nucleic acids enhance the efficiency of protein production, intracellular retention of nucleic acids, and viability of contacted cells, as well as possess reduced immunogenicity, of these nucleic acids compared to unmodified nucleic acids, having these properties are termed "enhanced nucleic acids" herein.

In addition, the present disclosure provides nucleic acids, which have decreased binding affinity to a major groove interacting, e.g. binding, partner. For example, the nucleic acids are comprised of at least one nucleotide that has been chemically modified on the major groove face as described herein.

The term "nucleic acid," in its broadest sense, includes any compound and/or substance that is or can be incorporated into an oligonucleotide chain. Exemplary nucleic acids for use in accordance with the present disclosure include, but are not limited to, one or more of DNA, RNA including messenger mRNA (mRNA), hybrids thereof, RNAi-inducing agents, RNAi agents, siRNAs, shRNAs, miRNAs, antisense RNAs, ribozymes, catalytic DNA, RNAs that induce triple helix formation, aptamers, vectors, etc., described in detail herein.

Provided are modified nucleic acids containing a translatable region and one, two, or more than two different nucleoside modifications. In some embodiments, the modified nucleic acid exhibits reduced degradation in a cell into which the nucleic acid is introduced, relative to a corresponding unmodified nucleic acid. Exemplary nucleic acids include ribonucleic acids (RNAs), deoxyribonucleic acids (DNAs), threose nucleic acids (TNAs), glycol nucleic acids (GNAs), locked nucleic acids (LNAs) or a hybrid thereof. In preferred embodiments, the modified nucleic acid includes messenger RNAs (mRNAs). As described herein, the nucleic acids of the present disclosure do not substantially induce an innate immune response of a cell into which the mRNA is introduced.

In certain embodiments, it is desirable to intracellularly degrade a modified nucleic acid introduced into the cell, for example if precise timing of protein production is desired. Thus, the present disclosure provides a modified nucleic acid containing a degradation domain, which is capable of being acted on in a directed manner within a cell.

Other components of nucleic acid are optional, and are beneficial in some embodiments. For example, a 5' untranslated region (UTR) and/or a 3'UTR are provided, wherein either or both may independently contain one or more different nucleoside modifications. In such embodiments, nucleoside modifications may also be present in the translatable region. Also provided are nucleic acids containing a Kozak sequence.

Additionally, provided are nucleic acids containing one or more intronic nucleotide sequences capable of being excised from the nucleic acid.

Further, provided are nucleic acids containing an internal ribosome entry site (IRES). An IRES may act as the sole ribosome binding site, or may serve as one of multiple ribosome binding sites of an mRNA. An mRNA containing more than one functional ribosome binding site may encode several peptides or polypeptides that are translated independently by the ribosomes ("multicistronic mRNA"). When nucleic acids are provided with an IRES, further optionally provided is a second translatable region. Examples of IRES sequences that can be used according to the present disclosure include without limitation, those from picornaviruses (e.g. FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV).

In some embodiments, the nucleic acid sequences comprise a compound of Formula I-d:

I-d

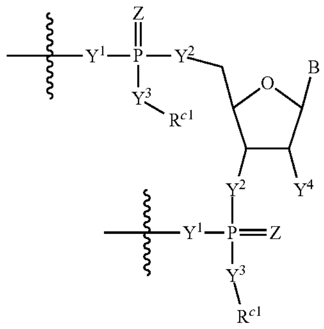

wherein:

Z is O or S;

each of $Y^1$ is independently selected from $-OR^{a1}$, $-NR^{a1}R^{b1}$, and $-SR^{a1}$;

each of $Y^2$ is independently selected from O, $NR^a$, S or a linker comprising an atom selected from the group consisting of C, O, N, and S;

each of $Y^3$ is independently selected from O and S;

$Y^4$ is selected from H, —$OR^a$, —$SR^a$, and —$NHR^a$;

B is a nucleobase;

$R^a$ is H, $C_{1-20}$ alkyl, $C_{2-20}$ alkenyl, $C_{2-20}$ alkynyl, or $C_{6-20}$ aryl;

$R^{a1}$ and $R^{b1}$ are each independently H or a counterion; and —$Y^3$—$R^{c1}$ is OH or SH at a pH of about 1 or —$Y^3$—$R^{c1}$ is $O^-$ or $S^-$ at physiological pH;

or —$Y^3R^{c1}$ is $C_{1-20}$ alkoxy, $C_{2-20}$ —O-alkenyl, or $C_{1-20}$ —O-alkynyl;

wherein when B is an unmodified nucleobase selected from cytosine, guanine, thymidine, uracil and adenine, then at least one of Z, $Y^1$ or $Y^2$ is not O or OH.

In some embodiments, B is a nucleobase of Formula II-a, II-b, or II-c:

II-a

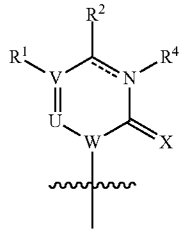

II-b

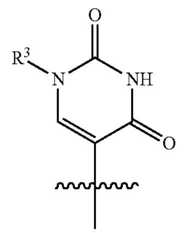

II-c

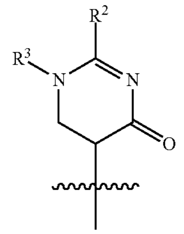

wherein:

- - - denotes a single or double bond;

X is O or S;

U and W are each independently C or N;

V is O, S, C or N;

wherein when V is C then $R^1$ is H, $C_{1-6}$ alkyl, $C_{1-6}$ alkenyl, $C_{1-6}$ alkynyl, halo, or —$OR^c$, wherein $C_{1-20}$ alkyl, $C_{2-20}$ alkenyl, $C_{2-20}$ alkynyl are each optionally substituted with —OH, —$NR^aR^b$, —SH, —C(O)$R^c$, —C(O)O$R^c$, —NHC(O)$R^c$, or —NHC(O)O$R^c$;

and wherein when V is O, S, or N then $R^1$ is absent;

$R^2$ is H, —$OR^c$, —$SR^c$, —$NR^aR^b$, or halo;

or when V is C then $R^1$ and $R^2$ together with the carbon atoms to which they are attached can form a 5- or 6-membered ring optionally substituted with 1-4 substituents selected from halo, —OH, —SH, —$NR^aR^b$, $C_{1-20}$ alkyl, $C_{2-20}$ alkenyl, $C_{2-20}$ alkynyl, $C_{1-20}$ alkoxy, or $C_{1-20}$ thioalkyl;

$R^3$ is H or $C_{1-20}$ alkyl;

$R^4$ is H or $C_{1-20}$ alkyl; wherein when - - - denotes a double bond then $R^4$ is absent, or N—$R^4$, taken together, forms a positively charged N substituted with $C_{1-20}$ alkyl;

$R^a$ and $R^b$ are each independently H, $C_{1-20}$ alkyl, $C_{2-20}$ alkenyl, $C_{2-20}$ alkynyl, or $C_{6-20}$ aryl; and $R^c$ is H, $C_{1-20}$ alkyl, $C_{2-20}$ alkenyl, phenyl, benzyl, a polyethylene glycol group, or an amino-polyethylene glycol group.

In some embodiments, B is a nucleobase of Formula II-a1, II-a2, II-a3, II-a4, or II-a5:

II-a1

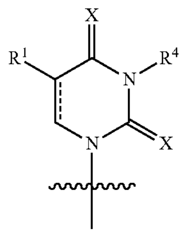

II-a2

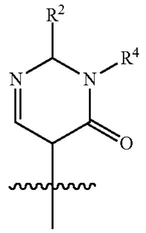

II-a3

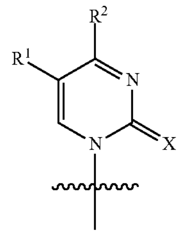

II-a4

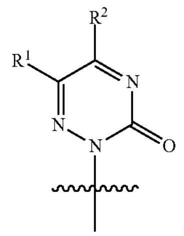

II-a5

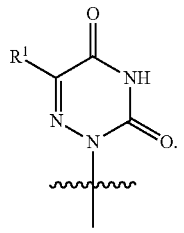

In some embodiments, at least 25% of the cytosines are replaced by a compound of Formula I-a (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%).

In some embodiments, at least 25% of the uracils are replaced by a compound of Formula I-a (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%).

In some embodiments, at least 25% of the cytosines and 25% of the uracils are replaced by a compound of Formula I-a (e.g., at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%).

In some embodiments, the nucleic acid is translatable.

Major Groove Interacting Partners

As described herein, the phrase "major groove interacting partner" refers RNA recognition receptors that detect and respond to RNA ligands through interactions, e.g. binding, with the major groove face of a nucleotide or nucleic acid. As such, RNA ligands comprising modified nucleotides or nucleic acids as described herein decrease interactions with major groove binding partners, and therefore decrease an innate immune response, or expression and secretion of pro-inflammatory cytokines, or both.

Example major groove interacting, e.g. binding, partners include, but are not limited to the following nucleases and helicases. Within membranes, TLRs (Toll-like Receptors) 3, 7, and 8 can respond to single- and double-stranded RNAs. Within the cytoplasm, members of the superfamily 2 class of DEX(D/H) helicases and ATPases can sense RNAs to initiate antiviral responses. These helicases include the RIG-I (retinoic acid-inducible gene I) and MDA5 (melanoma differentiation-associated gene 5). Other examples include laboratory of genetics and physiology 2 (LGP2), HIN-200 domain containing proteins, or Helicase-domain containing proteins.

Prevention or Reduction of Innate Cellular Immune Response Activation Using Modified Nucleic Acids The term "innate immune response" includes a cellular response to exogenous nucleic acids, including single stranded nucleic acids, generally of viral or bacterial origin, which involves the induction of cytokine expression and release, particularly the interferons, and cell death. Protein synthesis is also reduced during the innate cellular immune response. While it is advantageous to eliminate the innate immune response in a cell, the present disclosure provides modified mRNAs that substantially reduce the immune response, including interferon signaling, without entirely eliminating such a response. In some embodiments, the immune response is reduced by 10%, 20%, 30%, 40%, 50%, 60%, 70%, 80%, 90%, 95%, 99%, 99.9%, or greater than 99.9% as compared to the immune response induced by a corresponding unmodified nucleic acid. Such a reduction can be measured by expression or activity level of Type 1 interferons or the expression of interferon-regulated genes such as the toll-like receptors (e.g., TLR7 and TLR8). Reduction of innate immune response can also be measured by decreased cell death following one or more administrations of modified RNAs to a cell population; e.g., cell death is 10%, 25%, 50%, 75%, 85%, 90%, 95%, or over 95% less than the cell death frequency observed with a corresponding unmodified nucleic acid. Moreover, cell death may affect fewer than 50%, 40%, 30%, 20%, 10%, 5%, 1%, 0.1%, 0.01% or fewer than 0.01% of cells contacted with the modified nucleic acids.

The present disclosure provides for the repeated introduction (e.g., transfection) of modified nucleic acids into a target cell population, e.g., in vitro, ex vivo, or in vivo. The step of contacting the cell population may be repeated one or more times (such as two, three, four, five or more than five times). In some embodiments, the step of contacting the cell population with the modified nucleic acids is repeated a number of times sufficient such that a predetermined efficiency of protein translation in the cell population is achieved. Given the reduced cytotoxicity of the target cell population provided by the nucleic acid modifications, such repeated transfections are achievable in a diverse array of cell types.

Polypeptide Variants

Provided are nucleic acids that encode variant polypeptides, which have a certain identity with a reference polypeptide sequence. The term "identity" as known in the art, refers to a relationship between the sequences of two or more peptides, as determined by comparing the sequences. In the art, "identity" also means the degree of sequence relatedness between peptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related peptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

In some embodiments, the polypeptide variant has the same or a similar activity as the reference polypeptide. Alternatively, the variant has an altered activity (e.g., increased or decreased) relative to a reference polypeptide. Generally, variants of a particular polynucleotide or polypeptide of the present disclosure will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular reference polynucleotide or polypeptide as determined by sequence alignment programs and parameters described herein and known to those skilled in the art.

As recognized by those skilled in the art, protein fragments, functional protein domains, and homologous proteins are also considered to be within the scope of this present disclosure. For example, provided herein is any protein fragment of a reference protein (meaning a polypeptide sequence at least one amino acid residue shorter than a reference polypeptide sequence but otherwise identical) 10, 20, 30, 40, 50, 60, 70, 80, 90, 100 or greater than 100 amino acids in length In another example, any protein that includes a stretch of about 20, about about 40, about 50, or about 100 amino acids which are about 40%, about 50%, about 60%, about 70%, about 80%, about 90%, about 95%, or about 100% identical to any of the sequences described herein can be utilized in accordance with the present disclosure. In certain embodiments, a protein sequence to be utilized in accordance with the present disclosure includes 2, 3, 4, 5, 6, 7, 8, 9, 10, or more mutations as shown in any of the sequences provided or referenced herein.

Polypeptide Libraries

Also provided are polynucleotide libraries containing nucleoside modifications, wherein the polynucleotides individually contain a first nucleic acid sequence encoding a polypeptide, such as an antibody, protein binding partner, scaffold protein, and other polypeptides known in the art. Preferably, the polynucleotides are mRNA in a form suitable for direct introduction into a target cell host, which in turn synthesizes the encoded polypeptide.

In certain embodiments, multiple variants of a protein, each with different amino acid modification(s), are produced and tested to determine the best variant in terms of pharmacokinetics, stability, biocompatibility, and/or biological activity, or a biophysical property such as expression level. Such a library may contain 10, $10^2$, $10^3$, $10^4$, $10^5$, $10^6$, $10^7$, $10^8$, $10^9$, or over $10^9$ possible variants (including substitutions, deletions of one or more residues, and insertion of one or more residues).

Polypeptide-Nucleic Acid Complexes

Proper protein translation involves the physical aggregation of a number of polypeptides and nucleic acids associated with the mRNA. Provided by the present disclosure are protein-nucleic acid complexes, containing a translatable mRNA having one or more nucleoside modifications (e.g., at least two different nucleoside modifications) and one or more polypeptides bound to the mRNA. Generally, the proteins are provided in an amount effective to prevent or reduce an innate immune response of a cell into which the complex is introduced.

Untranslatable Modified Nucleic Acids

As described herein, provided are mRNAs having sequences that are substantially not translatable. Such mRNA is effective as a vaccine when administered to a mammalian subject.

Also provided are modified nucleic acids that contain one or more noncoding regions. Such modified nucleic acids are generally not translated, but are capable of binding to and sequestering one or more translational machinery component such as a ribosomal protein or a transfer RNA (tRNA), thereby effectively reducing protein expression in the cell. The modified nucleic acid may contain a small nucleolar RNA (sno-RNA), micro RNA (miRNA), small interfering RNA (siRNA) or Piwi-interacting RNA (piRNA).

Synthesis of Modified Nucleic Acids

Nucleic acids for use in accordance with the present disclosure may be prepared according to any available technique including, but not limited to chemical synthesis, enzymatic synthesis, which is generally termed in vitro transcription, enzymatic or chemical cleavage of a longer precursor, etc. Methods of synthesizing RNAs are known in the art (see, e.g., Gait, M. J. (ed.) *Oligonucleotide synthesis: a practical approach*, Oxford [Oxfordshire], Washington, DC: IRL Press, 1984; and Herdewijn, P. (ed.) *Oligonucleotide synthesis: methods and applications*, Methods in Molecular Biology, v. 288 (Clifton, N.J.) Totowa, N.J.: Humana Press, 2005; both of which are incorporated herein by reference).

The modified nucleosides and nucleotides disclosed herein can be prepared from readily available starting materials using the following general methods and procedures. It is understood that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

Preparation of modified nucleosides and nucleotides can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis,* 2d. Ed., Wiley & Sons, 1991, which is incorporated herein by reference in its entirety.

The reactions of the processes described herein can be carried out in suitable solvents, which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of modified nucleosides and nucleotides can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art. Modified nucleic acids need not be uniformly modified along the entire length of the molecule. Different nucleotide modifications and/or backbone structures may exist at various positions in the nucleic acid. One of ordinary skill in the art will appreciate that the nucleotide analogs or other modification(s) may be located at any position(s) of a nucleic acid such that the function of the nucleic acid is not substantially decreased. A modification may also be a 5' or 3' terminal modification. The nucleic acids may contain at a minimum one and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the nucleic acids may contain a modified pyrimidine such as uracil or cytosine. In some embodiments, at least 5%, at least 10%, at least 25%, at least 50%, at least 80%, at least 90% or 100% of the uracil in the nucleic acid is replaced with a modified uracil. The modified uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the nucleic acid is replaced with a modified cytosine. The modified cytosine can be replaced by a compound having a single unique structure, or can be replaced by a plurality of compounds having different structures (e.g., 2, 3, 4 or more unique structures).

Generally, the shortest length of a modified mRNA of the present disclosure can be the length of an mRNA sequence that is sufficient to encode for a dipeptide. In another embodiment, the length of the mRNA sequence is sufficient to encode for a tripeptide. In another embodiment, the length of an mRNA sequence is sufficient to encode for a tetrapeptide. In another embodiment, the length of an mRNA sequence is sufficient to encode for a pentapeptide. In another embodiment, the length of an mRNA sequence is sufficient to encode for a hexapeptide. In another embodiment, the length of an mRNA sequence is sufficient to encode for a heptapeptide. In another embodiment, the length of an mRNA sequence is sufficient to encode for an octapeptide. In another embodiment, the length of an mRNA sequence is sufficient to encode for a nonapeptide. In another embodiment, the length of an mRNA sequence is sufficient to encode for a decapeptide.

Examples of dipeptides that the modified nucleic acid sequences can encode for include, but are not limited to, carnosine and anserine.

In a further embodiment, the mRNA is greater than 30 nucleotides in length. In another embodiment, the RNA molecule is greater than 35 nucleotides in length. In another embodiment, the length is at least 40 nucleotides. In another embodiment, the length is at least 45 nucleotides. In another embodiment, the length is at least 55 nucleotides. In another embodiment, the length is at least 60 nucleotides. In another embodiment, the length is at least 60 nucleotides. In another embodiment, the length is at least 80 nucleotides. In another embodiment, the length is at least nucleotides. In another embodiment, the length is at least 100 nucleotides. In another embodiment, the length is at least 120 nucleotides. In another embodiment, the length is at least 140 nucleotides. In another embodiment, the length is at least 160 nucleotides. In another embodiment, the length is at least 180 nucleotides. In another embodiment, the length is at least 200 nucleotides. In another embodiment, the length is at least 250 nucleotides. In another embodiment, the length is at least 300 nucleotides. In another embodiment, the length is at least 350 nucleotides. In another embodiment, the length is at least 400 nucleotides. In another embodiment, the length is at least 450 nucleotides. In another embodiment, the length is at least 500 nucleotides. In another embodiment, the length is at least 600 nucleotides. In another embodiment, the length is at least 700 nucleotides. In another embodiment, the length is at least 800 nucleotides. In another embodiment, the length is at least 900 nucleotides. In another embodiment, the length is at least 1000 nucleotides. In another embodiment, the length is at least 1100 nucleotides. In another embodiment, the length is at least 1200 nucleotides. In another embodiment, the length is at least 1300 nucleotides. In another embodiment, the length is at least 1400 nucleotides. In another embodiment, the length is at least 1500 nucleotides. In another embodiment, the length is at least 1600 nucleotides. In another embodiment, the length is at least 1800 nucleotides. In another embodiment, the length is at least 2000 nucleotides. In another embodiment, the length is at least 2500 nucleotides. In another embodiment, the length is at least 3000 nucleotides. In another embodiment, the length is at least 4000 nucleotides. In another embodiment, the length is at least 5000 nucleotides, or greater than 5000 nucleotides.

The present disclosure provides methods of preparing a nucleic acid sequence comprising a nucleotide that disrupts binding of a major groove interacting partner with the nucleic acid sequence, wherein the nucleic acid sequence comprises a compound of Formula I-d:

I-d

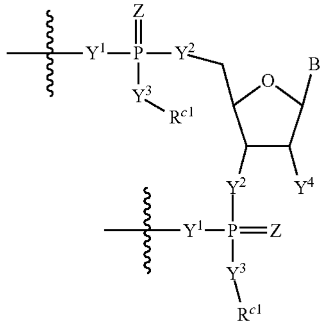

wherein:

Z is O or S;

each of $Y^1$ is independently selected from —$OR^{a1}$, —$NR^{a1}R^{b1}$, and —$SR^{a1}$;

each of $Y^2$ is independently selected from O, $NR^a$, S or a linker comprising an atom selected from the group consisting of C, O, N, and S;

each of $Y^3$ is independently selected from O and S;

$Y^4$ is selected from H, —$OR^a$, —$SR^a$, and —$NHR^a$;

B is a nucleobase;

$R^a$ is H, $C_{1-20}$ alkyl, $C_{2-20}$ alkenyl, $C_{2-20}$ alkynyl, or $C_{6-20}$ aryl;

$R^{a1}$ and $R^{b1}$ are each independently H or a counterion; and

—$Y^3$—$R^{c1}$ is OH or SH at a pH of about 1 or —$Y^3$—$R^{c1}$ is $O^-$ or $S^-$ at physiological pH;

or —$Y^3$—$R^{c1}$ is $C_{1-20}$ alkoxy, $C_{2-20}$ —O-alkenyl, or $C_{1-20}$ —O-alkynyl;

wherein when B is an unmodified nucleobase selected from cytosine, guanine, uracil and adenine, then at least one of Z, $Y^1$ or $Y^2$ is not O or OH;

the method comprising:

reacting a compound of Formula I-c:

I-c

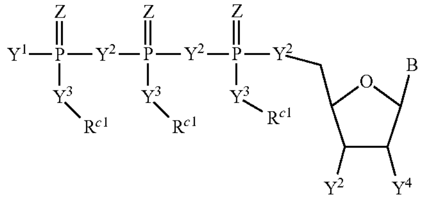

with an RNA polymerase, and a cDNA template.

In some embodiments, the reaction is repeated from 1 to about 7,000 times.

In some embodiments, B is a nucleobase of Formula II-a, II-b, or II-c:

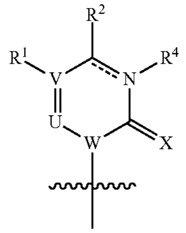

II-a

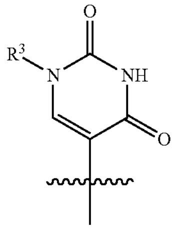

II-b

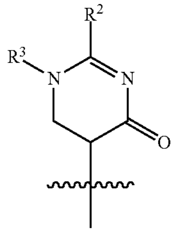

II-c wherein:

 denotes a single or double bond;

X is O or S;

U and W are each independently C or N;

V is O, S, C or N;

wherein when V is C then $R^1$ is H, $C_{1-6}$ alkyl, $C_{1-6}$ alkenyl, $C_{1-6}$ alkynyl, halo, or —$OR^c$, wherein $C_{1-20}$ alkyl, $C_{2-20}$ alkenyl, $C_{2-20}$ alkynyl are each optionally substituted with —OH, —SH, —$C(O)R^c$, —$C(O)OR^c$, —$NHC(O)R^c$, or —$NHC(O)OR^c$;

and wherein when V is O, S, or N then $R^1$ is absent;

$R^2$ is H, —$OR^c$, —$SR^c$, —$NR^aR^b$, or halo;

or when V is C then $R^1$ and $R^2$ together with the carbon atoms to which they are attached can form a 5- or 6-membered ring optionally substituted with 1-4 substituents selected from halo, —OH, —SH, $C_{1-20}$ alkyl, $C_{2-20}$ alkenyl, $C_{2-20}$ alkynyl, $C_{1-20}$ alkoxy, or $C_{1-20}$ thioalkyl;

$R^3$ is H or $C_{1-20}$ alkyl;

$R^4$ is H or $C_{1-20}$ alkyl; wherein when denotes a double bond then $R^4$ is absent, or N—$R^4$, taken together, forms a positively charged N substituted with $C_{1-20}$ alkyl;

$^a$ and $R^b$ are each independently H, $C_{1-20}$ alkyl, $C_{2-20}$ alkenyl, $C_{2-20}$ alkynyl, or $C_{6-20}$ aryl; and $R^c$ is H, $C_{1-20}$ alkyl, $C_{2-20}$ alkenyl, phenyl, benzyl, a polyethylene glycol group, or an amino-polyethylene glycol group.

In some embodiments, B is a nucleobase of Formula II-a1, II-a2, II-a3, II-a4, or II-a5:

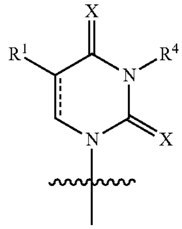

II-a1

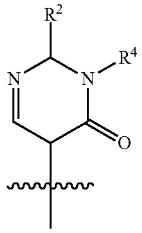

II-a2

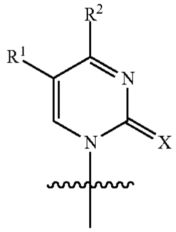

II-a3

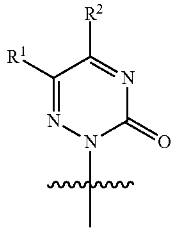

II-a4

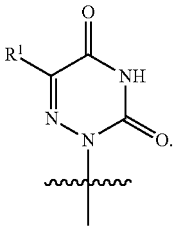

II-a5

In some embodiments, the methods further comprise a nucleotide selected from the group consisting of adenosine, cytosine, guanosine, and uracil.

In some embodiments, the nucleobase is a pyrimidine or derivative thereof.

In a further aspect, the present disclosure provides methods of amplifying a nucleic acid sequence comprising a nucleotide that disrupts binding of a major groove binding partner with the nucleic acid sequence, the method comprising: reacting a compound of Formula I-c:

I-c

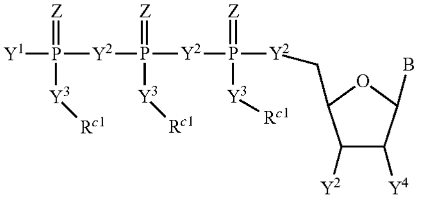

Z is O or S;

each of $Y^1$ is independently selected from —$OR^{a1}$, —$NR^{a1}R^{b1}$ and —$SR^{a1}$;

each of $Y^2$ is independently selected from O, $NR^a$, S or a linker comprising an atom selected from the group consisting of C, O, N, and S;

each of $Y^3$ is independently selected from O and S;

$Y^4$ is selected from H, —$OR^a$, —$SR^a$, and —$NHR^a$;

B is a nucleobase;

$R^a$ is H, $C_{1-20}$ alkyl, $C_{2-20}$ alkenyl, $C_{2-20}$ alkynyl, or $C_{6-20}$ aryl;

$R^{a1}$ and $R^{b1}$ are each independently H or a counterion; and —$Y^3$—$R^{c1}$ is OH or SH at a pH of about 1 or is $O^-$ or $S^-$ at physiological pH; or —$Y^3$—R is $C_{1-20}$ alkoxy, $C_{2-20}$ —O-alkenyl, or $C_{1-20}$ —O-alkynyl;

wherein when B is an unmodified nucleobase selected from cytosine, guanine, uracil and adenine, then at least one of Z, $Y^1$ or $Y^2$ is not O or OH;

with a primer, a cDNA template, and an RNA polymerase.

In some embodiments, B is a nucleobase of Formula II-a, II-b, or II-c:

II-a

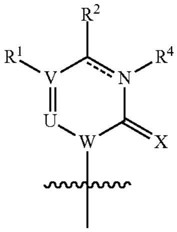

II-b

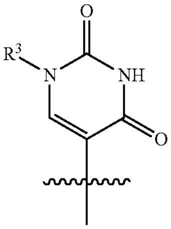

II-c

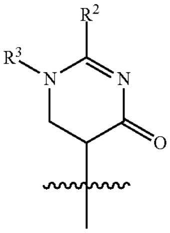

wherein:

 denotes a single or double bond;

X is O or S;

U and W are each independently C or N;

V is O, S, C or N;

wherein when V is C then $R^1$ is H, $C_{1-6}$ alkyl, $C_{1-6}$ alkenyl, $C_{1-6}$ alkynyl, halo, or —$OR^c$, wherein $C_{1-20}$ alkyl, $C_{2-20}$ alkenyl, $C_{2-20}$ alkynyl are each optionally substituted with —OH, —SH, —C(O)$R^c$, —C(O)O$R^c$, —NHC(O)$R^c$, or —NHC(O)O$R^c$;

and wherein when V is O, S, or N then $R^1$ is absent;

$R^2$ is H, —$OR^c$, $SR^c$, —$NR^aR^b$, or halo;

or when V is C then $R^1$ and $R^2$ together with the carbon atoms to which they are attached can form a 5- or 6-membered ring optionally substituted with 1-4 substituents selected from halo, —OH, —SH, $C_{1-20}$ alkyl, $C_{2-20}$ alkenyl, $C_{2-20}$ alkynyl, $C_{1-20}$ alkoxy, or $C_{1-20}$ thioalkyl;

$R^3$ is H or $C_{1-20}$ alkyl;

$R^4$ is H or $C_{1-20}$ alkyl; wherein when  denotes a double bond then $R^4$ is absent, or N—$R^4$, taken together, forms a positively charged N substituted with $C_{1-20}$ alkyl;

$R^a$ and $R^b$ are each independently H, $C_{1-20}$ alkyl, $C_{2-20}$ alkenyl, $C_{2-20}$ alkynyl, or $C_{6-20}$ aryl; and $R^c$ is H, $C_{1-20}$ alkyl, $C_{2-20}$ alkenyl, phenyl, benzyl, a polyethylene glycol group, or an amino-polyethylene glycol group.

In some embodiments, B is a nucleobase of Formula II-a1, II-a2, II-a3, II-a4, or II-a5:

II-a1

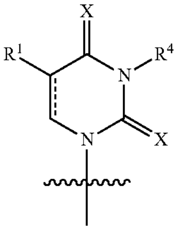

II-a2

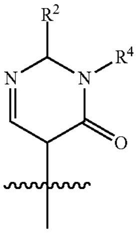

II-a3

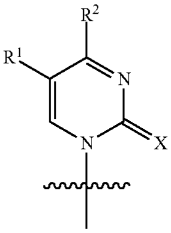

II-a4

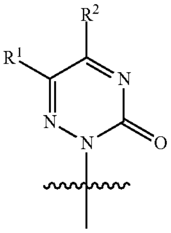

-continued

II-a5

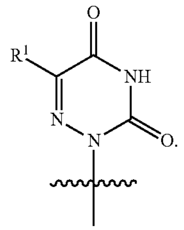

In some embodiments, the methods further comprise a nucleotide selected from the group consisting of adenosine, cytosine, guanosine, and uracil.

In some embodiments, the nucleobase is a pyrimidine or derivative thereof.

Uses of Modified Nucleic Acids

Therapeutic Agents

The modified nucleic acids and the proteins translated from the modified nucleic acids described herein can be used as therapeutic agents. For example, a modified nucleic acid described herein can be administered to a subject, wherein the modified nucleic acid is translated in vivo to produce a therapeutic peptide in the subject. Accordingly, provided herein are compositions, methods, kits, and reagents for treatment or prevention of disease or conditions in humans and other mammals. The active therapeutic agents of the present disclosure include modified nucleic acids, cells containing modified nucleic acids or polypeptides translated from the modified nucleic acids, polypeptides translated from modified nucleic acids, and cells contacted with cells containing modified nucleic acids or polypeptides translated from the modified nucleic acids.

In certain embodiments, provided are combination therapeutics containing one or more modified nucleic acids containing translatable regions that encode for a protein or proteins that boost a mammalian subject's immunity along with a protein that induces antibody-dependent cellular toxicity. For example, provided are therapeutics containing one or more nucleic acids that encode trastuzumab and granulocyte-colony stimulating factor (G-CSF). In particular, such combination therapeutics are useful in Her2+ breast cancer patients who develop induced resistance to trastuzumab. (See, e.g., Albrecht, Immunotherapy. 2(6): 795-8 (2010)).

Provided are methods of inducing translation of a recombinant polypeptide in a cell population using the modified nucleic acids described herein. Such translation can be in vivo, ex vivo, in culture, or in vitro. The cell population is contacted with an effective amount of a composition containing a nucleic acid that has at least one nucleoside modification, and a translatable region encoding the recombinant polypeptide. The population is contacted under conditions such that the nucleic acid is localized into one or more cells of the cell population and the recombinant polypeptide is translated in the cell from the nucleic acid.

An effective amount of the composition is provided based, at least in part, on the target tissue, target cell type, means of administration, physical characteristics of the nucleic acid (e.g., size, and extent of modified nucleosides), and other determinants. In general, an effective amount of the composition provides efficient protein production in the cell, preferably more efficient than a composition containing a corresponding unmodified nucleic acid. Increased efficiency may be demonstrated by increased cell transfection (i.e., the percentage of cells transfected with the nucleic acid), increased protein translation from the nucleic acid, decreased nucleic acid degradation (as demonstrated, e.g., by increased duration of protein translation from a modified nucleic acid), or reduced innate immune response of the host cell.

Aspects of the present disclosure are directed to methods of inducing in vivo translation of a recombinant polypeptide in a mammalian subject in need thereof. Therein, an effective amount of a composition containing a nucleic acid that has at least one nucleoside modification and a translatable region encoding the recombinant polypeptide is administered to the subject using the delivery methods described herein. The nucleic acid is provided in an amount and under other conditions such that the nucleic acid is localized into a cell of the subject and the recombinant polypeptide is translated in the cell from the nucleic acid. The cell in which the nucleic acid is localized, or the tissue in which the cell is present, may be targeted with one or more than one rounds of nucleic acid administration. Other aspects of the present disclosure relate to transplantation of cells containing modified nucleic acids to a mammalian subject. Administration of cells to mammalian subjects is known to those of ordinary skill in the art, such as local implantation (e.g., topical or subcutaneous administration), organ delivery or systemic injection (e.g., intravenous injection or inhalation), as is the formulation of cells in pharmaceutically acceptable carrier. Compositions containing modified nucleic acids are formulated for administration intramuscularly, transarterially, intraperitoneally, intravenously, intranasally, subcutaneously, endoscopically, transdermally, or intrathecally. In some embodiments, the composition is formulated for extended release.

The subject to whom the therapeutic agent is administered suffers from or is at risk of developing a disease, disorder, or deleterious condition. Provided are methods of identifying, diagnosing, and classifying subjects on these bases, which may include clinical diagnosis, biomarker levels, genome-wide association studies (GWAS), and other methods known in the art.

In certain embodiments, the administered modified nucleic acid directs production of one or more recombinant polypeptides that provide a functional activity which is substantially absent in the cell in which the recombinant polypeptide is translated. For example, the missing functional activity may be enzymatic, structural, or gene regulatory in nature.

In other embodiments, the administered modified nucleic acid directs production of one or more recombinant polypeptides that replace a polypeptide (or multiple polypeptides) that is substantially absent in the cell in which the recombinant polypeptide is translated. Such absence may be due to genetic mutation of the encoding gene or regulatory pathway thereof.

Alternatively, the recombinant polypeptide functions to antagonize the activity of an endogenous protein present in, on the surface of, or secreted from the cell. Usually, the activity of the endogenous protein is deleterious to the subject, for example, do to mutation of the endogenous protein resulting in altered activity or localization. Additionally, the recombinant polypeptide antagonizes, directly or indirectly, the activity of a biological moiety present in, on the surface of, or secreted from the cell. Examples of antagonized biological moieties include lipids (e.g., cholesterol), a lipoprotein (e.g., low density lipoprotein), a nucleic acid, a carbohydrate, or a small molecule toxin.

The recombinant proteins described herein are engineered for localization within the cell, potentially within a specific compartment such as the nucleus, or are engineered for secretion from the cell or translocation to the plasma membrane of the cell.

As described herein, a useful feature of the modified nucleic acids of the present disclosure is the capacity to reduce the innate immune response of a cell to an exogenous nucleic acid. Provided are methods for performing the titration, reduction or elimination of the immune response in a cell or a population of cells. In some embodiments, the cell is contacted with a first composition that contains a first dose of a first exogenous nucleic acid including a translatable region and at least one nucleoside modification, and the level of the innate immune response of the cell to the first exogenous nucleic acid is determined. Subsequently, the cell is contacted with a second composition, which includes a second dose of the first exogenous nucleic acid, the second dose containing a lesser amount of the first exogenous nucleic acid as compared to the first dose. Alternatively, the cell is contacted with a first dose of a second exogenous nucleic acid. The second exogenous nucleic acid may contain one or more modified nucleosides, which may be the same or different from the first exogenous nucleic acid or, alternatively, the second exogenous nucleic acid may not contain modified nucleosides. The steps of contacting the cell with the first composition and/or the second composition may be repeated one or more times.

Additionally, efficiency of protein production (e.g., protein translation) in the cell is optionally determined, and the cell may be re-transfected with the first and/or second composition repeatedly until a target protein production efficiency is achieved.

Therapeutics for Diseases and Conditions

Provided are methods for treating or preventing a symptom of diseases characterized by missing or aberrant protein activity, by replacing the missing protein activity or overcoming the aberrant protein activity. Because of the rapid initiation of protein production following introduction of modified mRNAs, as compared to viral DNA vectors, the compounds of the present disclosure are particularly advantageous in treating acute diseases such as sepsis, stroke, and myocardial infarction. Moreover, the lack of transcriptional regulation of the modified mRNAs of the present disclosure is advantageous in that accurate titration of protein production is achievable.

Diseases characterized by dysfunctional or aberrant protein activity include, but not limited to, cancer and proliferative diseases, genetic diseases (e.g., cystic fibrosis), autoimmune diseases, diabetes, neurodegenerative diseases, cardiovascular diseases, and metabolic diseases. The present disclosure provides a method for treating such conditions or diseases in a subject by introducing nucleic acid or cell-based therapeutics containing the modified nucleic acids provided herein, wherein the modified nucleic acids encode for a protein that antagonizes or otherwise overcomes the aberrant protein activity present in the cell of the subject. Specific examples of a dysfunctional protein are the missense mutation variants of the cystic fibrosis transmembrane conductance regulator (CFTR) gene, which produce a dysfunctional protein variant of CFTR protein, which causes cystic fibrosis.

Multiple diseases are characterized by missing (or substantially diminished such that proper protein function does not occur) protein activity. Such proteins may not be present, or are essentially non-functional. The present disclosure provides a method for treating such conditions or diseases in a subject by introducing nucleic acid or cell-based therapeutics containing the modified nucleic acids provided herein, wherein the modified nucleic acids encode for a protein that replaces the protein activity missing from the target cells of the subject. Specific examples of a dysfunctional protein are the nonsense mutation variants of the cystic fibrosis transmembrane conductance regulator (CFTR) gene, which produce a nonfunctional protein variant of CFTR protein, which causes cystic fibrosis.

Thus, provided are methods of treating cystic fibrosis in a mammalian subject by contacting a cell of the subject with a modified nucleic acid having a translatable region that encodes a functional CFTR polypeptide, under conditions such that an effective amount of the CTFR polypeptide is present in the cell. Preferred target cells are epithelial cells, such as the lung, and methods of administration are determined in view of the target tissue; i.e., for lung delivery, the RNA molecules are formulated for administration by inhalation.

In another embodiment, the present disclosure provides a method for treating hyperlipidemia in a subject, by introducing into a cell population of the subject with a modified mRNA molecule encoding Sortilin, a protein recently characterized by genomic studies, thereby ameliorating the hyperlipidemia in a subject. The SORT1 gene encodes a trans-Golgi network (TGN) transmembrane protein called Sortilin. Genetic studies have shown that one of five individuals has a single nucleotide polymorphism, rs12740374, in the 1p13 locus of the SORT1 gene that predisposes them to having low levels of low-density lipoprotein (LDL) and very-low-density lipoprotein (VLDL). Each copy of the minor allele, present in about 30% of people, alters LDL cholesterol by 8 mg/dL, while two copies of the minor allele, present in about 5% of the population, lowers LDL cholesterol 16 mg/dL. Carriers of the minor allele have also been shown to have a 40% decreased risk of myocardial infarction. Functional in vivo studies in mice describes that overexpression of SORT1 in mouse liver tissue led to significantly lower LDL-cholesterol levels, as much as 80% lower, and that silencing SORT1 increased LDL cholesterol approximately 200% (Musunuru K et al. From noncoding variant to phenotype via SORT1 at the 1p13 cholesterol locus. Nature 2010; 466: 714-721).

Methods of Cellular Nucleic Acid Delivery

Methods of the present disclosure enhance nucleic acid delivery into a cell population, in vivo, ex vivo, or in culture. For example, a cell culture containing a plurality of host cells (e.g., eukaryotic cells such as yeast or mammalian cells) is contacted with a composition that contains an enhanced nucleic acid having at least one nucleoside modification and, optionally, a translatable region. The composition also generally contains a transfection reagent or other compound that increases the efficiency of enhanced nucleic acid uptake into the host cells. The enhanced nucleic acid exhibits enhanced retention in the cell population, relative to a corresponding unmodified nucleic acid. The retention of the enhanced nucleic acid is greater than the retention of the unmodified nucleic acid. In some embodiments, it is at least about 50%, 75%, 90%, 95%, 100%, 150%, 200% or more than 200% greater than the retention of the unmodified nucleic acid. Such retention advantage may be achieved by one round of transfection with the enhanced nucleic acid, or may be obtained following repeated rounds of transfection.

In some embodiments, the enhanced nucleic acid is delivered to a target cell population with one or more additional nucleic acids. Such delivery may be at the same time, or the enhanced nucleic acid is delivered prior to delivery of the one or more additional nucleic acids.

The additional one or more nucleic acids may be modified nucleic acids or unmodified nucleic acids. It is understood that the initial presence of the enhanced nucleic acids does not substantially induce an innate immune response of the cell population and, moreover, that the innate immune response will not be activated by the later presence of the unmodified nucleic acids. In this regard, the enhanced nucleic acid may not itself contain a translatable region, if the protein desired to be present in the target cell population is translated from the unmodified nucleic acids.

Targeting Moieties

In some embodiments, modified nucleic acids are provided to express a protein-binding partner or a receptor on the surface of the cell, which functions to target the cell to a specific tissue space or to interact with a specific moiety, either in vivo or in vitro. Suitable protein-binding partners include antibodies and functional fragments thereof, scaffold proteins, or peptides. Additionally, modified nucleic acids can be employed to direct the synthesis and extracellular localization of lipids, carbohydrates, or other biological moieties.

Permanent Gene Expression Silencing

A method for epigenetically silencing gene expression in a mammalian subject, comprising a nucleic acid where the translatable region encodes a polypeptide or polypeptides capable of directing sequence-specific histone H3 methylation to initiate heterochromatin formation and reduce gene transcription around specific genes for the purpose of silencing the gene. For example, a gain-of-function mutation in the Janus Kinase 2 gene is responsible for the family of Myeloproliferative Diseases.

Pharmaceutical Compositions

The present disclosure provides proteins generated from modified mRNAs. Pharmaceutical compositions may optionally comprise one or more additional therapeutically active substances. In accordance with some embodiments, a method of administering pharmaceutical compositions comprising one or more proteins to be delivered to a subject in need thereof is provided. In some embodiments, compositions are administered to humans. For the purposes of the present disclosure, the phrase "active ingredient" generally refers to a protein or protein-containing complex as described herein.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, shaping and/or packaging the product into a desired single- or multi-dose unit.

A pharmaceutical composition in accordance with the present disclosure may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure will vary, depending upon the identity, size, and/or condition of the subject treated and further depending upon the route by which the composition is to be administered. By way of example, the composition may comprise between 0.1% and 100% (w/w) active ingredient.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy,* $21^{st}$ Edition, A. R. Gennaro (Lippincott, Williams & Wilkins, Baltimore, MD, 2006; incorporated herein by reference) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this present disclosure.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical formulations. Excipients such as cocoa butter and suppository waxes, coloring agents, coating agents, sweetening, flavoring, and/or perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and/or combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween®20], polyoxyethylene sorbitan [Tween®60], polyoxyethylene sorbitan monooleate [Tween®80], sorbitan monopalmitate [Span®40], sorbitan monostearate [Span®60], sorbitan tristearate [Span®65], glyceryl monooleate, sorbitan monooleate [Span®80]), polyoxyethylene esters (e.g. polyoxyethylene monostearate [Myrj®45], polyoxyethylene hydrogenated castor oil, polyethoxylated castor oil, polyoxymethylene stearate, and Solutol®), sucrose fatty acid esters, polyethylene glycol fatty acid esters (e.g. Cremophor), polyoxyethylene ethers, (e.g. polyoxyethylene lauryl ether [Brij®30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic®F 68, Poloxamer®188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol,); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus®, Phenonip®, methylparaben, Germall®115, Germaben®II, Neolone™, Kathon™, and/or Euxyl®.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, d-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Liquid dosage forms for oral and parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as Cremophor®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions which are compatible with body tissues.

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, an active ingredient is mixed with at least one inert, pharmaceutically acceptable excipient such as sodium citrate or dicalcium phosphate and/or fillers or extenders (e.g. starches, lactose, sucrose, glucose, mannitol, and silicic acid), binders (e.g. carboxymethylcellulose, alginates, gelatin, polyvinylpyrrolidinone, sucrose, and acacia), humectants (e.g. glycerol), disintegrating agents (e.g. agar, calcium carbonate, potato or tapioca starch, alginic acid, certain silicates, and sodium carbonate), solution retarding agents (e.g. paraffin), absorption accelerators (e.g. quaternary ammonium compounds), wetting agents (e.g. cetyl alcohol and glycerol monostearate), absorbents (e.g. kaolin and bentonite clay), and lubricants (e.g. talc, calcium stearate, magnesium stearate, solid polyethylene glycols, sodium lauryl sulfate), and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Dosage forms for topical and/or transdermal administration of a composition may include ointments, pastes, creams, lotions, gels, powders, solutions, sprays, inhalants and/or patches. Generally, an active ingredient is admixed under sterile conditions with a pharmaceutically acceptable excipient and/or any needed preservatives and/or buffers as may be required. Additionally, the present disclosure contemplates the use of transdermal patches, which often have the added advantage of providing controlled delivery of a compound to the body. Such dosage forms may be prepared, for example, by dissolving and/or dispensing the compound in the proper medium. Alternatively or additionally, rate may be controlled by either providing a rate controlling membrane and/or by dispersing the compound in a polymer matrix and/or gel.

Suitable devices for use in delivering intradermal pharmaceutical compositions described herein include short needle devices such as those described in U.S. Pat. Nos. 4,886,499; 5,190,521; 5,527,288; 4,270,537; 5,015,235;

5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid compositions to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions.

Topically-administrable formulations may, for example, comprise from about 1% to about 10% (w/w) active ingredient, although the concentration of active ingredient may be as high as the solubility limit of the active ingredient in the solvent. Formulations for topical administration may further comprise one or more of the additional ingredients described herein.

A pharmaceutical composition may be prepared, packaged, and/or sold in a formulation suitable for pulmonary administration via the buccal cavity. Such a formulation may comprise dry particles which comprise the active ingredient and which have a diameter in the range from about 0.5 nm to about 7 nm or from about 1 nm to about 6 nm. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nm and at least 95% of the particles by number have a diameter less than 7 nm. Alternatively, at least 95% of the particles by weight have a diameter greater than 1 nm and at least 90% of the particles by number have a diameter less than 6 nm. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (w/w) of the composition, and active ingredient may constitute 0.1% to 20% (w/w) of the composition. A propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide an active ingredient in the form of droplets of a solution and/or suspension. Such formulations may be prepared, packaged, and/or sold as aqueous and/or dilute alcoholic solutions and/or suspensions, optionally sterile, comprising active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. Droplets provided by this route of administration may have an average diameter in the range from about 0.1 nm to about 200 nm.

Formulations described herein as being useful for pulmonary delivery are useful for intranasal delivery of a pharmaceutical composition. Another formulation suitable for intranasal administration is a coarse powder comprising the active ingredient and having an average particle from about 0.2 μm to 500 μm. Such a formulation is administered in the manner in which snuff is taken, i.e. by rapid inhalation through the nasal passage from a container of the powder held close to the nose.

Formulations suitable for nasal administration may, for example, comprise from about as little as 0.1% (w/w) and as much as 100% (w/w) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, 0.1% to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein.

A pharmaceutical composition may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid excipient. Such drops may further comprise buffering agents, salts, and/or one or more other of any additional ingredients described herein. Other opthalmically-administrable formulations which are useful include those which comprise the active ingredient in microcrystalline form and/or in a liposomal preparation. Ear drops and/or eye drops are contemplated as being within the scope of this present disclosure.

General considerations in the formulation and/or manufacture of pharmaceutical agents may be found, for example, in *Remington: The Science and Practice of Pharmacy* $21^{st}$ ed., Lippincott Williams & Wilkins, 2005 (incorporated herein by reference).

Administration

The present disclosure provides methods comprising administering proteins or complexes in accordance with the present disclosure to a subject in need thereof. Proteins or complexes, or pharmaceutical, imaging, diagnostic, or prophylactic compositions thereof, may be administered to a subject using any amount and any route of administration effective for preventing, treating, diagnosing, or imaging a disease, disorder, and/or condition (e.g., a disease, disorder, and/or condition relating to working memory deficits). The exact amount required will vary from subject to subject, depending on the species, age, and general condition of the subject, the severity of the disease, the particular composition, its mode of administration, its mode of activity, and the like. Compositions in accordance with the present disclosure are typically formulated in dosage unit form for ease of administration and uniformity of dosage. It will be understood, however, that the total daily usage of the compositions of the present disclosure will be decided by the attending physician within the scope of sound medical judgment. The specific therapeutically effective, prophylactially effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Proteins to be delivered and/or pharmaceutical, prophylactic, diagnostic, or imaging compositions thereof may be administered to animals, such as mammals (e.g., humans, domesticated animals, cats, dogs, mice, rats, etc.). In some embodiments, pharmaceutical, prophylactic, diagnostic, or imaging compositions thereof are administered to humans.

Proteins to be delivered and/or pharmaceutical, prophylactic, diagnostic, or imaging compositions thereof in accordance with the present disclosure may be administered by any route. In some embodiments, proteins and/or pharmaceutical, prophylactic, diagnostic, or imaging compositions thereof, are administered by one or more of a variety of routes, including oral, intravenous, intramuscular, intraarterial, intramedullary, intrathecal, subcutaneous, intraventricular, transdermal, interdermal, rectal, intravaginal, intraperitoneal, topical (e.g. by powders, ointments, creams, gels, lotions, and/or drops), mucosal, nasal, buccal, enteral, vitreal, intratumoral, sublingual; by intratracheal instillation, bronchial instillation, and/or inhalation; as an oral spray, nasal spray, and/or aerosol, and/or through a portal vein catheter. In some embodiments, proteins or complexes, and/or pharmaceutical, prophylactic, diagnostic, or imaging compositions thereof, are administered by systemic intravenous injection. In specific embodiments, proteins or complexes and/or pharmaceutical, prophylactic, diagnostic, or imaging compositions thereof may be administered intravenously and/or orally. In specific embodiments, proteins or complexes, and/or pharmaceutical, prophylactic, diagnostic, or imaging compositions thereof, may be administered in a way which allows the protein or complex to cross the blood-brain barrier, vascular barrier, or other epithelial barrier.

However, the present disclosure encompasses the delivery of proteins or complexes, and/or pharmaceutical, prophylactic, diagnostic, or imaging compositions thereof, by any appropriate route taking into consideration likely advances in the sciences of drug delivery.

In general the most appropriate route of administration will depend upon a variety of factors including the nature of the protein or complex comprising proteins associated with at least one agent to be delivered (e.g., its stability in the environment of the gastrointestinal tract, bloodstream, etc.), the condition of the patient (e.g., whether the patient is able to tolerate particular routes of administration), etc. The present disclosure encompasses the delivery of the pharmaceutical, prophylactic, diagnostic, or imaging compositions by any appropriate route taking into consideration likely advances in the sciences of drug delivery.

In certain embodiments, compositions in accordance with the present disclosure may be administered at dosage levels sufficient to deliver from about 0.0001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

Proteins or complexes may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. In some embodiments, the present disclosure encompasses the delivery of pharmaceutical, prophylactic, diagnostic, or imaging compositions in combination with agents that improve their bioavailability, reduce and/or modify their metabolism, inhibit their excretion, and/or modify their distribution within the body.

It will further be appreciated that therapeutically, prophylactically, diagnostically, or imaging active agents utilized in combination may be administered together in a single composition or administered separately in different compositions. In general, it is expected that agents utilized in combination with be utilized at levels that do not exceed the levels at which they are utilized individually. In some embodiments, the levels utilized in combination will be lower than those utilized individually.

The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, a composition useful for treating cancer in accordance with the present disclosure may be administered concurrently with a chemotherapeutic agent), or they may achieve different effects (e.g., control of any adverse effects).

Kits

The present disclosure provides a variety of kits for conveniently and/or effectively carrying out methods of the present disclosure. Typically kits will comprise sufficient amounts and/or numbers of components to allow a user to perform multiple treatments of a subject(s) and/or to perform multiple experiments.

In one aspect, the disclosure provides kits for protein production, comprising a first isolated nucleic acid comprising a translatable region and a nucleic acid modification, wherein the nucleic acid is capable of evading an innate immune response of a cell into which the first isolated nucleic acid is introduced, and packaging and instructions.

In one aspect, the disclosure provides kits for protein production, comprising: a first isolated nucleic acid comprising a translatable region, provided in an amount effective to produce a desired amount of a protein encoded by the translatable region when introduced into a target cell; a second nucleic acid comprising an inhibitory nucleic acid, provided in an amount effective to substantially inhibit the innate immune response of the cell; and packaging and instructions.

In one aspect, the disclosure provides kits for protein production, comprising a first isolated nucleic acid comprising a translatable region and a nucleoside modification, wherein the nucleic acid exhibits reduced degradation by a cellular nuclease, and packaging and instructions.

In one aspect, the disclosure provides kits for protein production, comprising a first isolated nucleic acid comprising a translatable region and at least two different nucleoside modifications, wherein the nucleic acid exhibits reduced degradation by a cellular nuclease, and packaging and instructions.

In one aspect, the disclosure provides kits for protein production, comprising a first isolated nucleic acid comprising a translatable region and at least one nucleoside modification, wherein the nucleic acid exhibits reduced degradation by a cellular nuclease; a second nucleic acid comprising an inhibitory nucleic acid; and packaging and instructions.

In some embodiments, the first isolated nucleic acid comprises messenger RNA (mRNA). In some embodiments the mRNA comprises at least one nucleoside selected from the group consisting of pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-l-deaza-pseudouridine, 2-thio-1-methyl-l-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In some embodiments, the mRNA comprises at least one nucleoside selected from the group consisting of 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-l-methyl-pseudoi socyti dine, 4-thio-l-methyl-1-deaza-pseudoisocytidine, 1-methyl-l-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-l-methyl-pseudoisocytidine.

In some embodiments, the mRNA comprises at least one nucleoside selected from the group consisting of 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyl adenosine, N6, N6-dimethyladenosine, 7-methyladenine, 2-methylthio-adenine, and 2-methoxy-adenine.

In some embodiments, the mRNA comprises at least one nucleoside selected from the group consisting of inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methyl-guanosine, N2, N2-dimethylguanosine, 8-oxo-guanosine, 7-methyl-8-oxo-guanosine, 1-methyl-6-thio-guanosine, N2-methyl-6-thio-guanosine, and N2, N2-dimethyl-6-thio-guanosine.

In another aspect, the disclosure provides compositions for protein production, comprising a first isolated nucleic acid comprising a translatable region and a nucleoside modification, wherein the nucleic acid exhibits reduced degradation by a cellular nuclease, and a mammalian cell suitable for translation of the translatable region of the first nucleic acid.

EXAMPLES

The invention is further described in the following examples, which do not limit the scope of the invention described in the claims.

Example 1

Modified mRNA In Vitro Transcription

Materials and Methods

Modified mRNAs (modRNAs) were made using standard laboratory methods and materials for in vitro transcription with the exception that the nucleotide mix contained modified nucleotides. The open reading frame (ORF) of the gene of interest is flanked by a 5' untranslated region (UTR) containing a strong Kozak translational initiation signal and an alpha-globin 3' UTR terminating with an oligo(dT) sequence for templated addition of a polyA tail for modRNAs not incorporating Adenosine analogs. Adenosine-containing modRNAs were synthesized without an oligo (dT) sequence to allow for post-transcription poly (A) polymerase poly-(A) tailing. The modRNAs were modified by incorporating chemically modified nucleotides indicated in Table 3 (below) during the in vitro transcription with 100% replacement of the corresponding natural nucleotide or partial replacement of the corresponding natural nucleotide at the indicated percentage.

Table 3 indicates the chemical identity of each chemically-distinct modified nucleotide incorporated into a modified mRNA with the given chemistry designation number.

TABLE 3

| Modified Nucleotide | Chemistry # |
|---|---|
| 6-aza-cytidine | Chem 1 |
| 2-thio-cytidine | Chem 2 |
| α-thio-cytidine | Chem 3 |
| Pseudo-iso-cytidine | Chem 4 |
| 5-aminoallyl-uridine | Chem 5 |
| 5-iodo-uridine | Chem 6 |
| N1-methyl-pseudouridine | Chem 7 |
| 5,6-dihydrouridine | Chem 8 |
| α-thio-uridine | Chem 9 |

TABLE 3-continued

| | Chemistry # |
|---|---|
| 4-thio-uridine | Chem 10 |
| 6-aza-uridine | Chem 11 |
| 5-hydroxy-uridine | Chem 12 |
| Deoxy-thymidine | Chem 13 |
| Pseudo-uridine | Chem 14 |
| Inosine | Chem 15 |
| α-thio-guanosine | Chem 16 |
| 8-oxo-guanosine | Chem 17 |
| O6-methyl-guanosine | Chem 18 |
| 7-deaza-guanosine | Chem 19 |
| No modification | Chem 20 |
| N1-methyl-adenosine | Chem 21 |
| 2-amino-6-Chloro-purine | Chem 22 |
| N6-methyl-2-amino-purine | Chem 23 |
| 6-Chloro-purine | Chem 24 |
| N6-methyl-adenosine | Chem 25 |
| α-thio-adenosine | Chem 26 |
| 8-azido-adenosine | Chem 27 |
| 7-deaza-adenosine | Chem 28 |
| Modified Nucleotide Combination | |
| α-thio-cytidine/5-iodo-uridine | Chem 29 |
| α-thio-cytidine/N1-methyl-pseudo-uridine | Chem 30 |
| α-thio-cytidine/α-thio-uridine | Chem 31 |
| α-thio-cytidine/5-methyl-uridine | Chem 32 |
| α-thio-cytidine/pseudo-uridine | Chem 33 |
| Pseudo-iso-cytidine/5-iodo-uridine | Chem 34 |
| Pseudo-iso-cytidine/N1-methyl-pseudo-uridine | Chem 35 |
| Pseudo-iso-cytidine/α-thio-uridine | Chem 36 |
| Pseudo-iso-cytidine/5-methyl-uridine | Chem 37 |
| Pseudo-iso-cytidine/Pseudo-uridine | Chem 38 |
| Pyrrolo-cytidine | Chem 39 |
| Pyrrolo-cytidine/5-iodo-uridine | Chem 40 |
| Pyrrolo-cytidine/N1-methyl-pseudo-uridine | Chem 41 |
| Pyrrolo-cytidine/α-thio-uridine | Chem 42 |
| Pyrrolo-cytidine/5-methyl-uridine | Chem 43 |
| Pyrrolo-cytidine/Pseudo-uridine | Chem 44 |
| 5-methyl-cytidine/5-iodo-uridine | Chem 45 |
| 5-methyl-cytidine/N1-methyl-pseudo-uridine | Chem 46 |
| 5-methyl-cytidine/α-thio-uridine | Chem 47 |
| 5-methyl-cytidine/5-methyl-uridine | Chem 48 |
| 5-methyl-cytidine/Pseudo-uridine | Chem 49 |
| 5-methyl-cytidine | Chem 50 |
| 25% Pseudo-iso-cytidine | Chem 51 |
| 25% N1-methyl-pseudo-uridine | Chem 52 |
| 25% N1-Methyl-pseudo-uridine/75%-pseudo-uridine | Chem 53 |
| 5-methyl-uridine | Chem 54 |
| 5-iodo-cytidine | Chem 55 |

Agarose Gel Electrophoresis of modRNA: Individual modRNAs (200-400 ng in a 20 volume) were loaded into a well on a non-denaturing 1.2% Agarose E-Gel (Invitrogen, Carlsbad, CA) and run for 12-15 minutes according to the manufacturer protocol (FIG. 1A). Tables 4 and 5 below indicate the modified nucleotide (Table 4) or nucleic acid (Table 5) loaded in each lane. These data indicate which chemically modified nucleotides were transcribed into chemically-modified mRNAs and the quality of each individual modRNA. These data demonstrate that nucleotides with chemical modifications on the major groove and minor groove face of the nucleotide were capable of being transcribed into a modRNA.

TABLE 4

| Lane | Modified NTP |
|---|---|
| 1 | α-thio-cytidine |
| 2 | Pseudo-iso-cytidine |
| 3 | 5-aminoallyl-uridine |
| 4 | 5-iodo-uridine |
| 5 | N1-methyl-pseudo-uridine |
| 6 | α-thio-uridine |
| 7 | 4-thio-uridine |
| 8 | 5-hydroxy-uridine |
| 9 | Deoxy-thymidine |
| 10 | Pseudo-uridine |
| 11 | Inosine |
| 12 | α-thio-guanosine |
| 13 | 8-oxo-guanosine |
| 14 | N1-methyl-guanosine |
| 15 | O6-methyl-guanosine |
| 16 | No modification |
| 17 | N1-methyl-adenosine |
| 18 | 2-amino-6-Chloro-purine |
| 19 | N6-methyl-2-amino-purine |
| 20 | 6-Chloro-purine |
| 21 | α-thio-adenosine |
| 22 | 8-azido-adenosine |
| 23 | 7-deaza-adenosine |
| 24 | 6-aza-cytidine |
| 25 | 2-thio-cytidine |
| 26 | 5,6-dihydro-uridine |
| 27 | 6-aza-uridine |
| 28 | 7-deaza-guanosine |
| 29 | N6-methyl-adenosine |

TABLE 5

| Lane | Modified NTP combination |
|---|---|
| 1 | α-thio-cytidine/5-iodo-uridine |
| 2 | α-thio-cytidine/N1-methyl-pseudouridine |
| 3 | α-thio-cytidine/α-thio-uridine |
| 4 | α-thio-cytidine/5-methyl-uridine |
| 5 | α-thio-cytidine/pseudouridine |
| 6 | 5-iodo-cytidine/5-iodo-uridine |
| 7 | 5-iodo-cytidine/N1-methyl-pseudouridine |
| 8 | 5-iodo-cytidine/α-thio-uridine |
| 9 | 5-iodo-cytidine/5-methyl-uridine |
| 10 | 5-iodo-cytidine/pseudouridine |
| 11 | Pseudo-iso-cytidine/5-iodo-uridine |
| 12 | Pyrrolo-cytidine |
| 13 | Pyrrolo-cytidine/5-iodo-uridine |
| 14 | Pyrrolo-cytidine/N1-methyl-pseudouridine |
| 15 | Pyrrolo-cytidine/α-thio-uridine |
| 16 | Pyrrolo-cytidine/5-methyl-uridine |
| 17 | Pyrrolo-cytidine/pseudouridine |
| 18 | 5-methyl-cytidine/5-iodo-uridine |
| 19 | 5-methyl-cytidine/N1-methyl-uridine |
| 20 | 5-methyl-cytidine/α-thio-uridine |
| 21 | 5-methyl-cytidine/5-methyl-uridine |
| 22 | 5-methyl-cytidine/pseudouridine |
| 23 | Pseudo-iso-cytidine/N1-methyl-pseudouridine |
| 24 | Pseudo-iso-cytidine/α-thio-uridine |
| 25 | Pseudo-iso-cytidine/5-methyl-uridine |
| 26 | Pseudo-iso-cytidine/pseudouridine |
| 27 | 5-methyl-cytidine |
| 28 | 25% pseudo-iso-cytidine |
| 29 | 25% N1-methyl-pseudouridine |
| 30 | 25% N1-methyl-pseudouridine/75% pseudouridine |

Figure 1B:
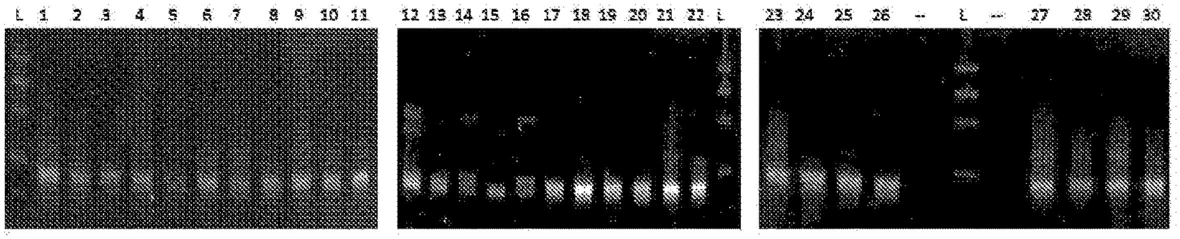

Agarose Gel Electrophoresis of RT-PCR products: Individual reverse transcribed-PCR products (200-400ng) were loaded into a well of a non-denaturing 1.2% Agarose E-Gel (Invitrogen, Carlsbad, CA) and run for 12-15 minutes according to the manufacturer protocol (FIG. 1B). Table 5 below indicates the modified nucleotide loaded in each lane.

Nanodrop modRNA quantification and UV spectral data: modRNAs in TE buffer (1 μl) were used for Nanodrop UV absorbance readings to quantitate the yield of each modRNA from an in vitro transcription reaction (UV absorbance traces are shown in FIGS. 6A-6L).

These data indicate which chemically modified nucleotides were transcribed into chemically-modified mRNAs. These data also demonstrate that nucleotides with chemical modifications on the major groove and minor groove face of the nucleotide were capable of being transcribed into a modRNA. These data further demonstrate that the nucleotides of the present invention are transcription-competent and compatible with incorporation into a modRNA, which may have altered UV spectra due to the presence of a given modified nucleotide. For example, Pyrrolo-C containing modRNAs have an increase in UV absorbance at a lower wavelength due to the presence of the pyrrolo ring of the modified C nucleotide. In another example, 2-amino-adenine nucleotide-containing modRNAs have an increase in UV absorbance at a higher wavelength due to the presence of an exocyclic amine off the purine ring. Nucleotides that are not transcription-competent and cannot be incorporated into a modRNA have a scrambled UV spectrum indicating no product from the transcription reaction.

Example 2

Modified RNA Transfection

Reverse Transfection: For experiments performed in a 24-well collagen-coated tissue culture plate, Keratinocytes were seeded at a cell density of $1\times10^5$. For experiments performed in a 96-well collagen-coated tissue culture plate, Keratinocytes were seeded at a cell density of $0.5\times10^5$. For each modRNA to be transfected, modRNA: RNAiMAX was prepared as described and mixed with the cells in the multi-well plate within a period of time, e.g., 6 hours, of cell seeding before cells had adhered to the tissue culture plate.

Forward Transfection: In a 24-well collagen-coated tissue culture plate, Keratinocytes were seeded at a cell density of $0.7\times10^5$. For experiments performed in a 96-well collagen-coated tissue culture plate, Keratinocytes were seeded at a cell density of $0.3\times10^5$. Keratinocytes were then grown to a confluency of >70% for over 24 hours. For each modRNA to be transfected, modRNA: RNAiMAX was prepared as described and transfected onto the cells in the multi-well plate over 24 hours after cell seeding and adherence to the tissue culture plate.

modRNA Translation Screen: G-CSF ELISA

Figure 2A:
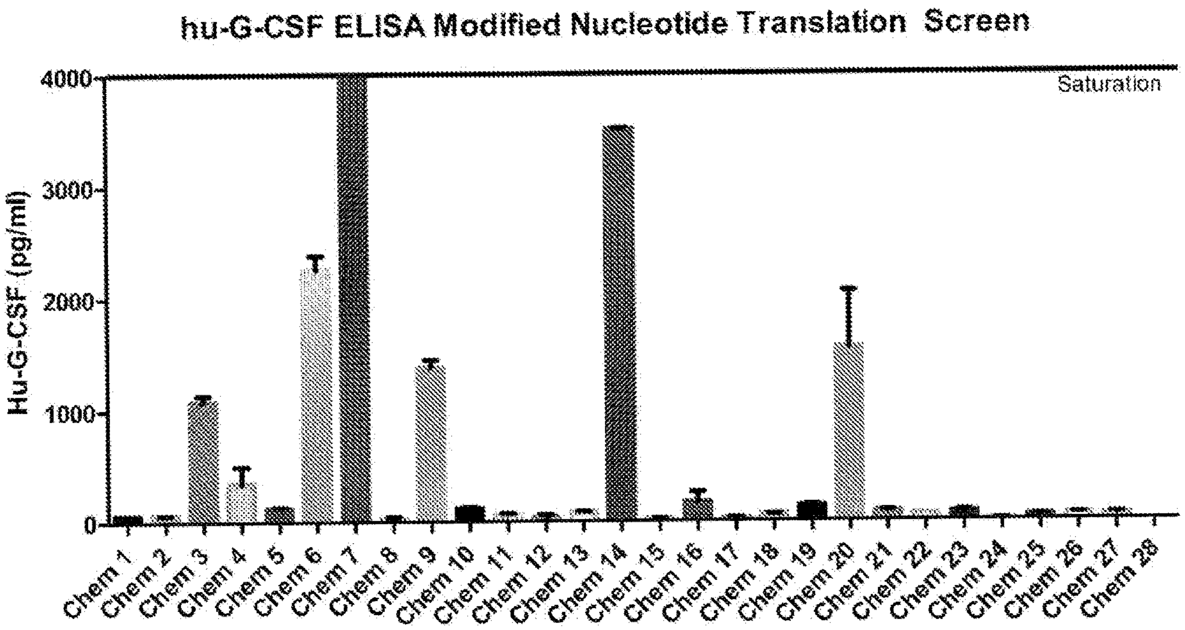
FIGS. 2A and 2B depict images of an Enzyme-linked immunosorbent assay (ELISA) for Human Granulocyte-Colony Stimulating Factor (G-CSF) of in vitro transfected Human Keratinocyte cells with each indicated modRNA encoding human G-CSF and the line indicates a saturating level of maximum detectable limit of secreted G-CSF in the assay.
Figure 2B:
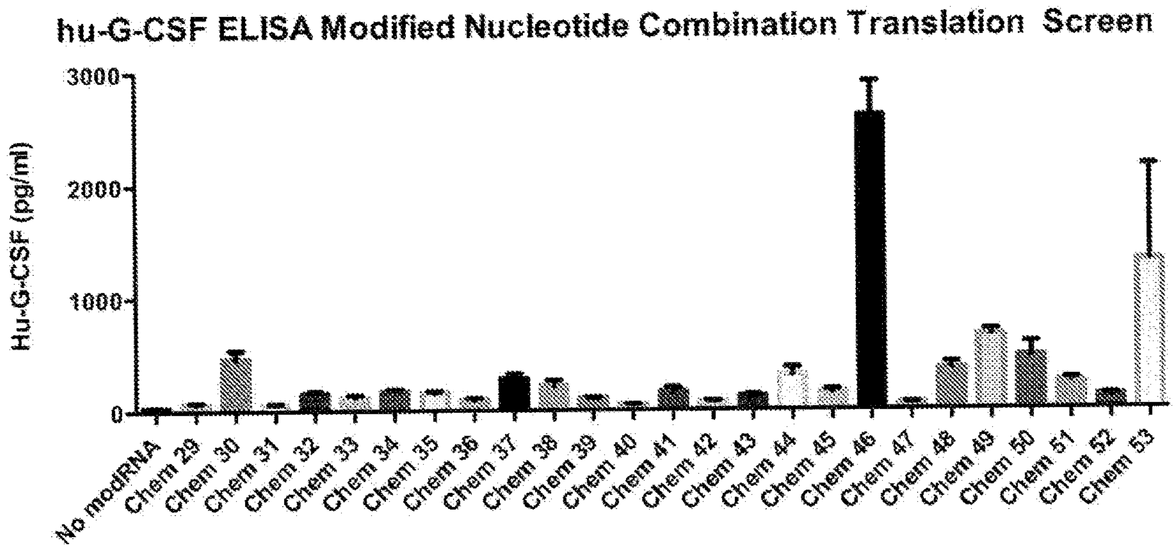

FIGS. 2A and 2B show an Enzyme-linked immunosorbent assay (ELISA) for Human Granulocyte-Colony Stimulating Factor (hu-G-CSF) of in vitro transfected Human Keratinocyte cells. Keratinocytes were grown in EpiLife medium with Supplement S7 from Invitrogen at a confluence of >70%. FIG. 2A keratinocytes were reverse transfected with 300 ng of the indicated chemically modified mRNA complexed with RNAiMAX from Invitrogen. FIG. 2B keratinocytes were forward transfected with 300 ng modRNA complexed with RNAiMAX from Invitrogen. The RNA:RNAiMAX complex was formed by first incubating the RNA with Supplement-free EpiLife media in a 5× volumetric dilution for 10 minutes at room temperature.

In a second vial, RNAiMAX reagent was incubated with Supplement-free EpiLife Media in a volumetric dilution for 10 minutes at room temperature. The RNA vial was then mixed with the RNAiMAX vial and incubated for 20-30 at room temperature before being added to the cells in a drop-wise fashion. Secreted huG-CSF concentration in the culture medium was measured at 18 hours post-transfection for each of the chemically modified mRNAs in triplicate. Secretion of Human Granulocyte-Colony Stimulating Factor (G-CSF) from transfected human keratinocytes was quantified using an ELISA kit from Invitrogen or R&D Systems (Minneapolis, MN) following the manufacturers recommended instructions. These data show that huG-CSF modRNAs comprised of chemically distinct nucleotide analogs (SEQ ID NO: 2) is capable of being translated in Human Keratinocyte cells and that huG-CSF is transported out of the cells and released into the extracellular environment. These data indicate which modified nucleotides were translated into protein when incorporated into a chemically modified mRNA. These data show that modified RNA containing nucleotides with chemical modifications on the major groove face of pyrimidine analogs have the highest levels of secreted hu-G-CSF into the cell culture medium.

modRNA Dose and Duration: G-CSF ELISA

Figure 3A:
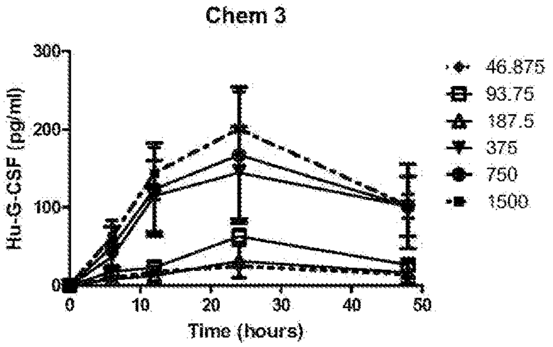
FIGS. 3A-N depict line graphs of a series of Enzyme-linked immunosorbent assays (ELISA) for Human Granulocyte-Colony Stimulating Factor (G-CSF) secreted from in vitro-transfected Human Keratinocyte cells at different time points with each indicated human G-CSF-encoding modRNA at the indicated doses. The line indicates a saturating level of maximum detectable limit of secreted G-CSF in the assay.
Figure 3B:
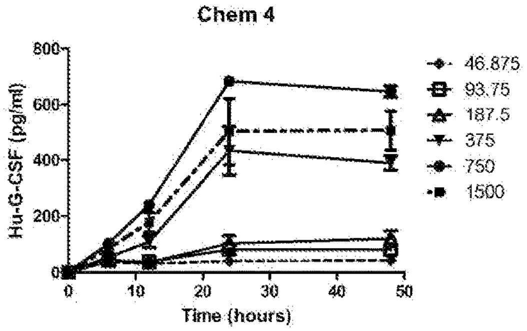
Figure 3C:
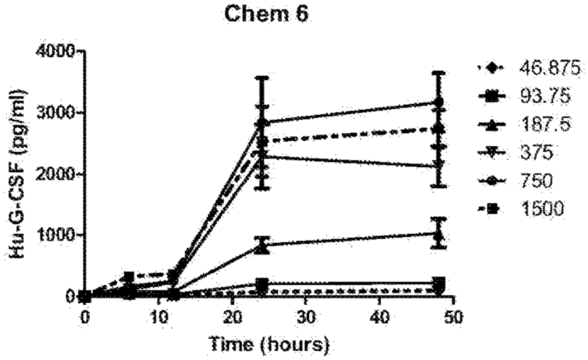
Figure 3D:
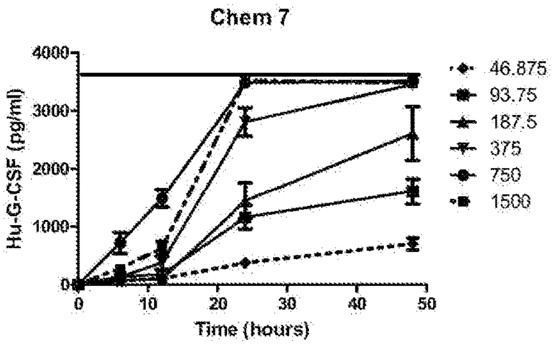
Figure 3E:
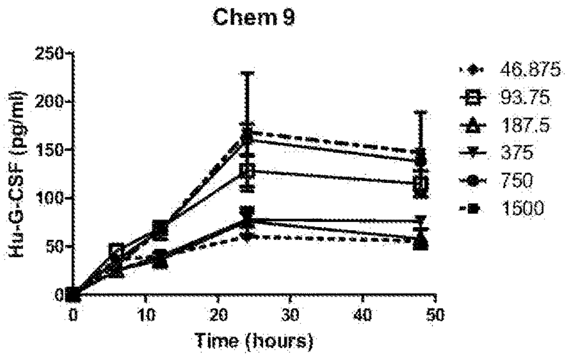
Figure 3F:
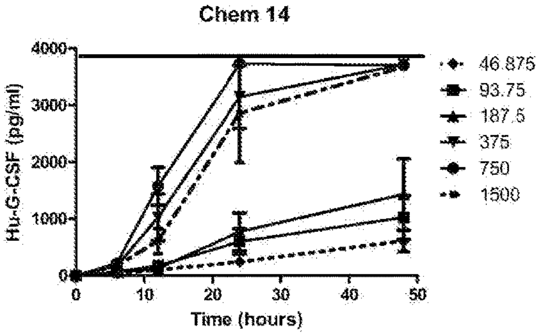
Figure 3G:
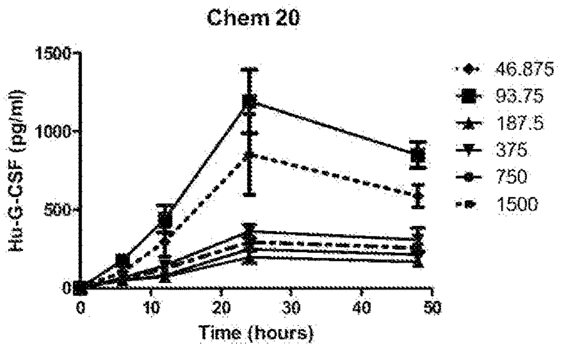
Figure 3H:
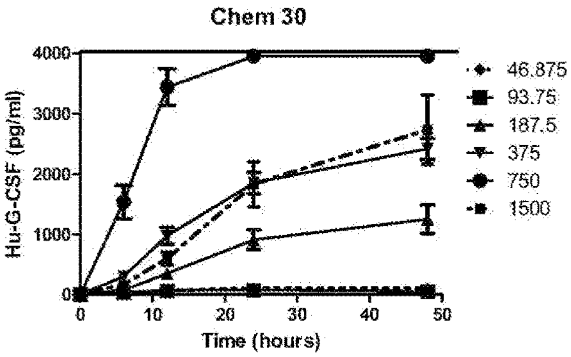
Figure 3I:
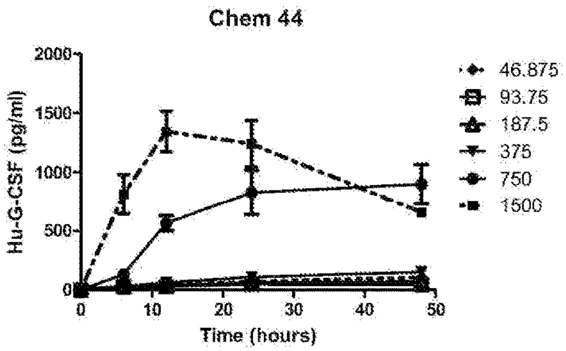
Figure 3J:
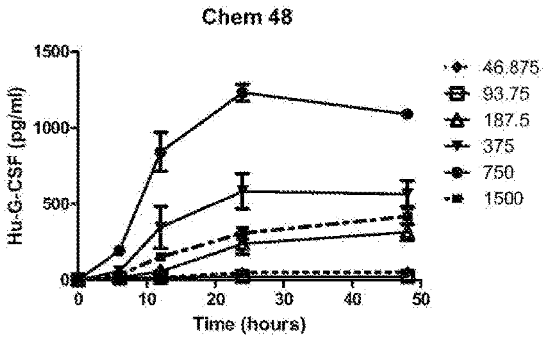
Figure 3K:
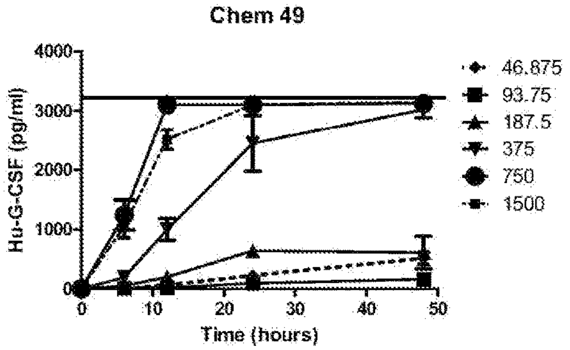
Figure 3L:
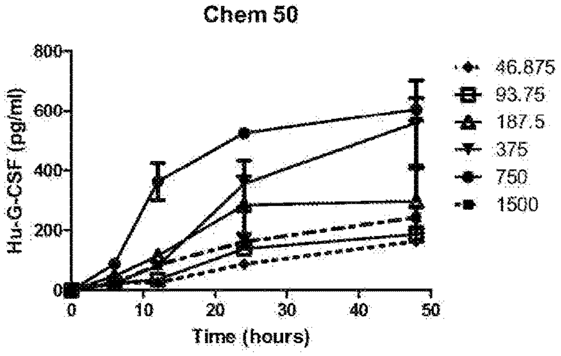
Figure 3M:
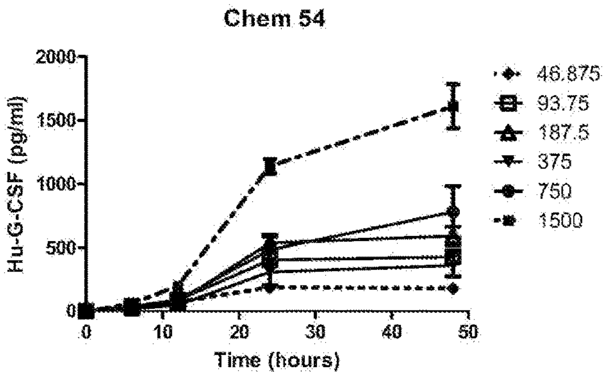
Figure 3N:
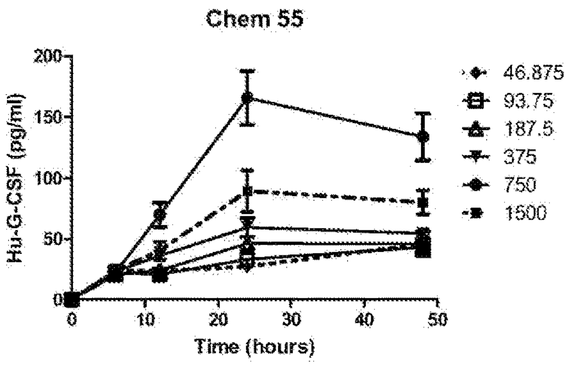

FIGS. 3A-N show Enzyme-linked immunosorbent assays (ELISA) for Human Granulocyte-Colony Stimulating Factor (G-CSF) of in vitro transfected Human Keratinocyte cells. Keratinocytes were grown in EpiLife medium with Supplement S7 from Invitrogen at a confluence of >70%. Keratinocytes were reverse transfected with 0 ng, 46.875 ng, 93.75 ng, 187.5 ng, 375 ng, 750 ng, or 1500 ng modRNA complexed with RNAiMAX from Invitrogen. The modRNA:RNAiMAX complex was formed as described. Secreted huG-CSF concentration in the culture medium was measured at 0, 6, 12, 24, and 48 hours post-transfection for each concentration of each modRNA in triplicate. Secretion of Human Granulocyte-Colony Stimulating Factor (G-CSF) from transfected human keratinocytes was quantified using an ELISA kit from Invitrogen or R&D Systems following the manufacturers recommended instructions. These data show that huG-CSF modRNAs comprised of chemically distinct nucleotide analogs (SEQ ID NO: X and Table 6) secreted hu-G-CSF protein in a modRNA dose-dependent manner from Human Keratinocyte cells and that huG-CSF is transported out of the cells and released into the extracellular environment. These data indicate which modified RNAs containing modified nucleotide analogs sustain hu-G-CSF expression for the longest and at the highest levels. These data show that modified RNA containing modified nucleotides with chemical modifications on the major groove face of pyrimidine analogs have the highest levels of secreted hu-G-CSF into the cell culture medium and that 750 ng of modRNA elicits the highest level of secreted hu-G-CSF.

Example 3

Cellular Innate Immune Response to modRNA

Figure 4A:
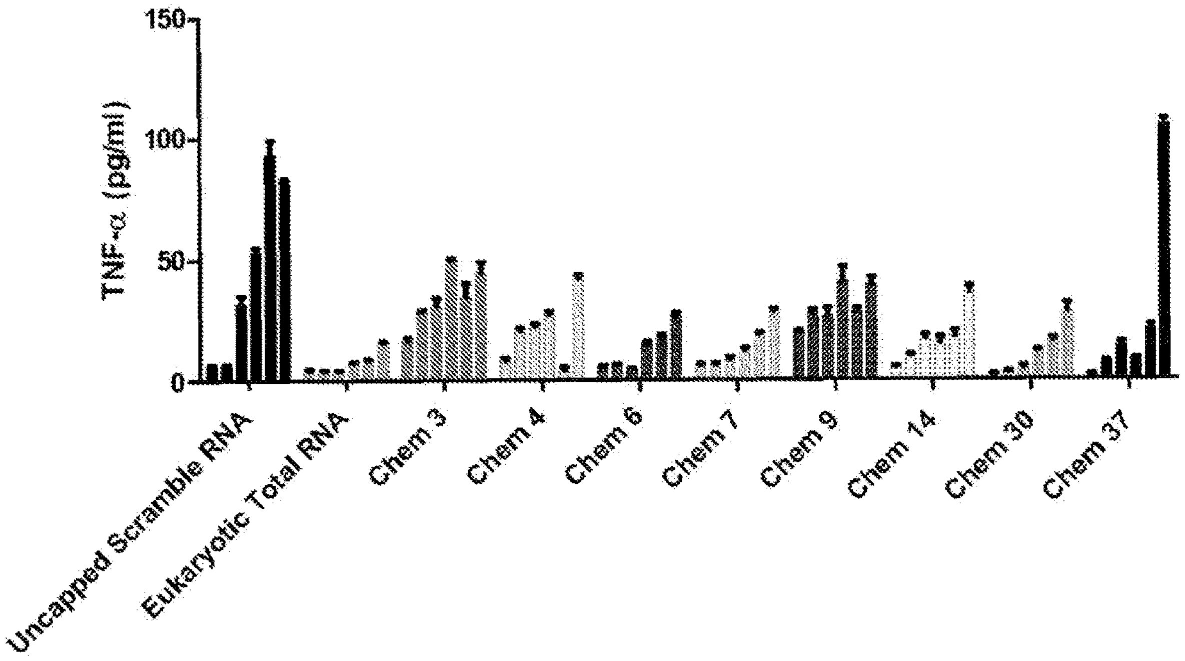
FIGS. 4A and 4B depict bar graphs of a series of Enzyme-linked immunosorbent assays (ELISA) for endogenous cellular human Tumor Necrosis Factor-α (TNF-α) secreted from in vitro-transfected Human Keratinocyte cells at 24 hours with each indicated hu-G-CSF-encoding modRNA at increasing doses.
Figure 4B:
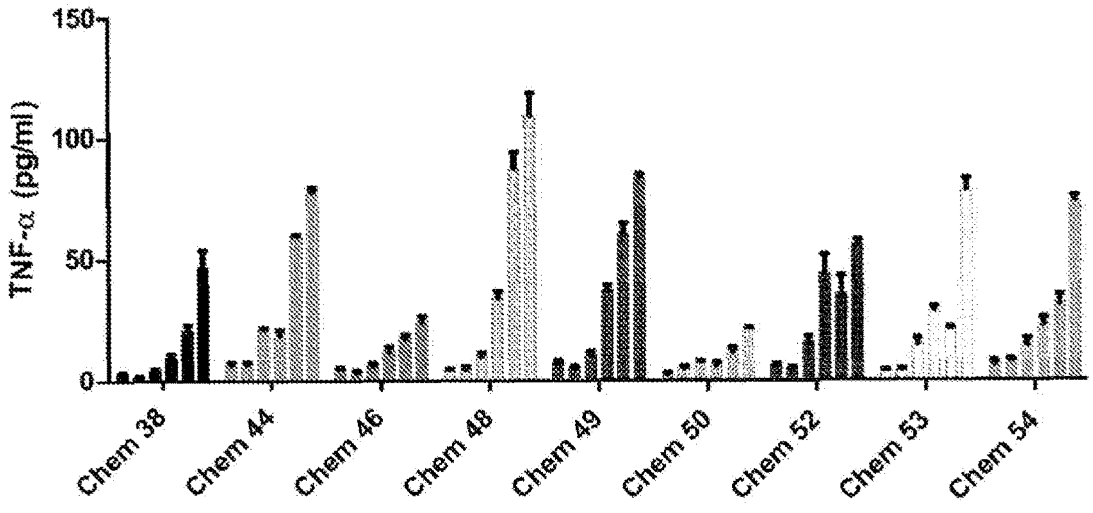

IFN-β ELISA and TNF-α ELISA:

FIGS. 4A-F show an Enzyme-linked immunosorbent assay (ELISA) for Human Tumor Necrosis Factor-α (TNF-α) (FIGS. 4A and 4B); Human Interferon-β (IFN-β) (FIGS. 4C and 4D); and Human Granulocyte-Colony Stimulating Factor (G-CSF) (FIGS. 4E and 4F) secreted from in vitro-transfected Human Keratinocyte cells. Keratinocytes were grown in EpiLife medium with Human Keratinocyte Growth Supplement in the absence of hydrocortisone from Invitrogen at a confluence of >70%. In FIGS. 4A and 4B, keratinocytes were reverse transfected with Ong, 93.75 ng, 187.5 ng, 375 ng, 750 ng, 1500 ng or 3000 ng of the indicated chemically modified mRNA complexed with RNAiMAX from Invitrogen as described in triplicate. Secreted TNF-a in the culture medium was measured 24 hours post-transfection for each of the chemically modified mRNAs using an ELISA kit from Invitrogen according to the manufacturer protocols.

Figure 4C:
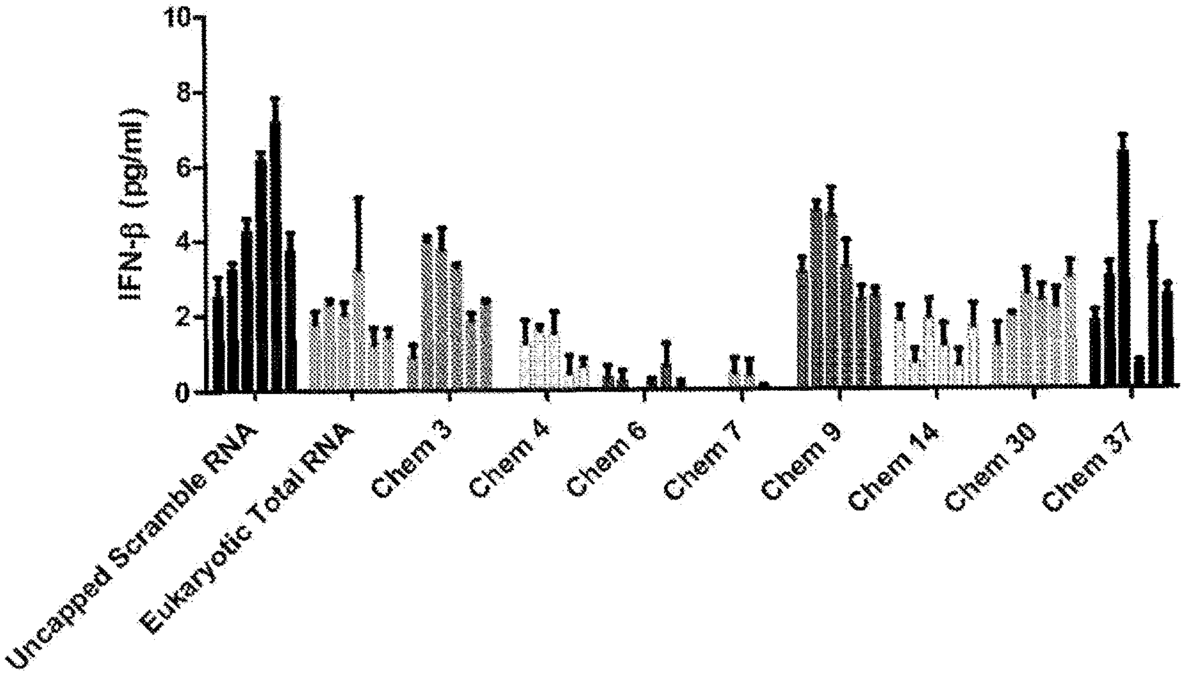
FIGS. 4C and 4D depict bar graphs of a series of Enzyme-linked immunosorbent assays (ELISA) for endogenous cellular human Interferon-β (IFN-β) secreted from in vitro-transfected Human Keratinocyte cells at 24 hours with each indicated hu-G-CSF-encoding modRNA at increasing doses.
Figure 4D:
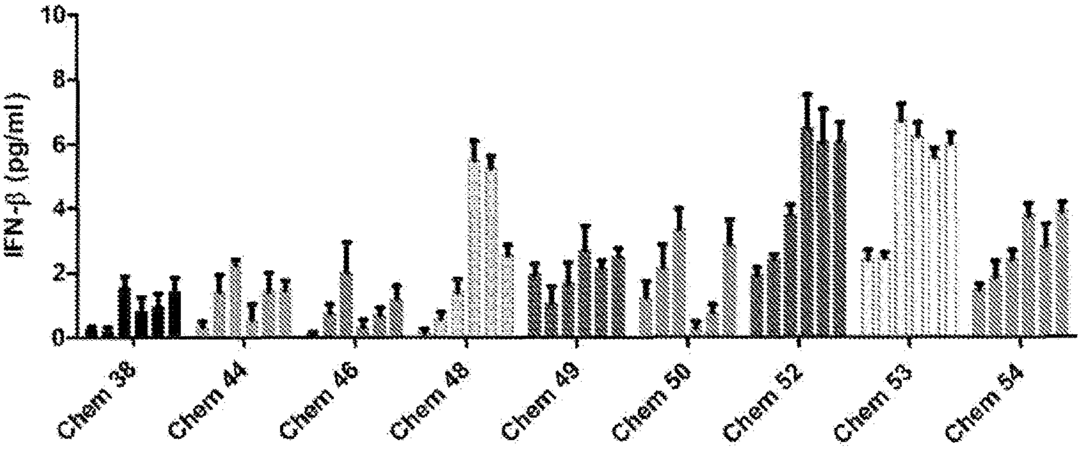
Figure 4E:
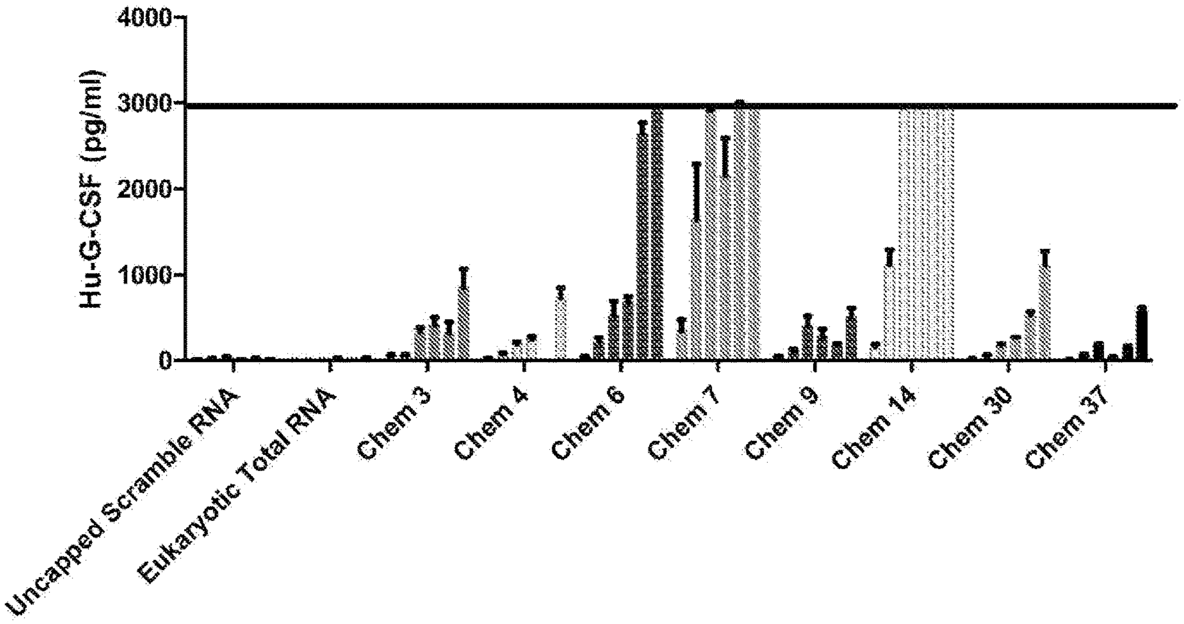
FIGS. 4E and 4F depict bar graphs of a series of Enzyme-linked immunosorbent assays (ELISA) for human-G-CSF secreted from in vitro-transfected Human Keratinocyte cells at 24 hours with each indicated hu-G-CSF-encoding modRNA at increasing doses.
Figure 4F:
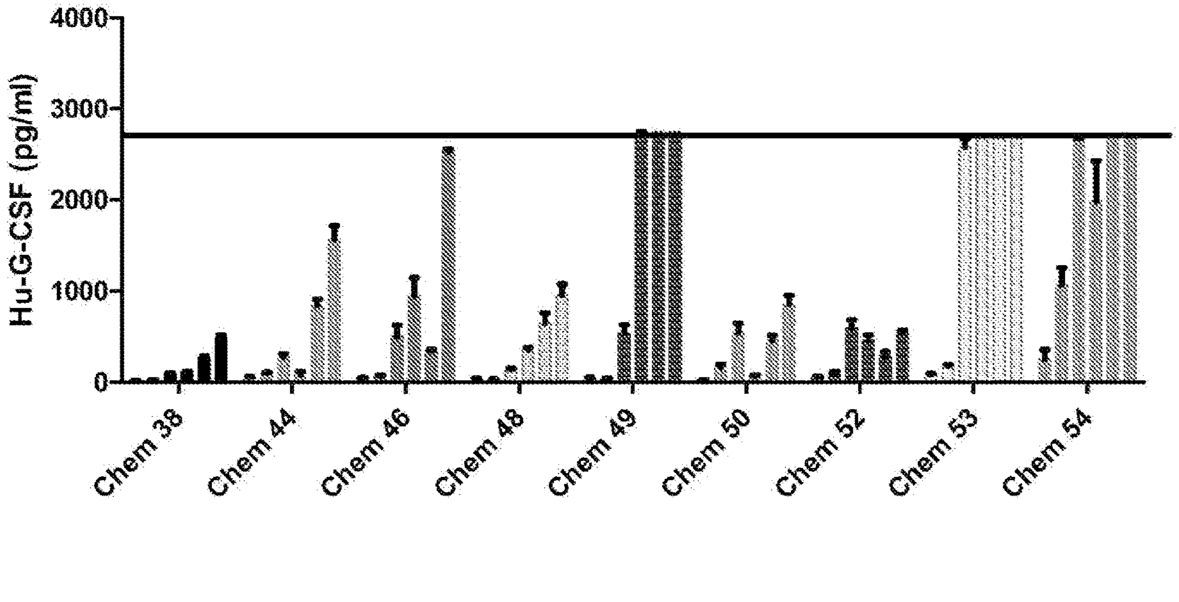

In FIGS. 4C and 4D, secreted IFN-β in the same culture medium was measured 24 hours post-transfection for each of the chemically modified mRNAs using an ELISA kit from Invitrogen according to the manufacturer protocols. In FIGS. 4E and 4F, secreted hu-G-CSF concentration in the same culture medium was measured at 24 hours post-transfection for each of the chemically modified mRNAs. Secretion of Human Granulocyte-Colony Stimulating Factor (G-CSF) from transfected human keratinocytes was quantified using an ELISA kit from Invitrogen or R&D Systems (Minneapolis, MN) following the manufacturers recommended instructions. These data indicate which modified RNAs containing modified nucleotides were capable of eliciting a reduced cellular innate immune response in comparison to natural and other chemically modified nucleotides by measuring exemplary type I cytokines TNF-α and IFN-β. These data show that modified RNAs containing modified nucleotides with chemical modifications on the major groove face of pyrimidine analogs have the lowest levels of secreted TNF-α and IFN-β into the cell culture medium while maintaining high levels of modRNA-encoding hu-G-CSF secretion into the cell culture medium.

Example 4

Human Granulocyte-Colony Stimulating Factor-modified RNA-induced Cell Proliferation Assay FIGS. 5A-D show modRNA-encoding hu-G-CSF produced by a human keratinocyte feeder cell layer induced the proliferation of both human myeloblast cells KG-1 and Kasumi-1 that express the G-CSF-receptor where the cell populations are separated by a semi-permeable membrane.

Human keratinocytes were grown in EpiLife medium with Supplement S7 from Invitrogen at a confluence of >70% in a 24-well collagen-coated Transwell® (Corning, Lowell, MA) co-culture tissue culture plate. Keratinocytes were reverse transfected with 750 ng of the indicated chemically modified mRNA complexed with RNAiMAX from Invitrogen as described in triplicate. The modRNA: RNAiMAX complex was formed as described. Keratinocyte media was exchanged 6-8 hours post-transfection. 42-hours post-transfection, the 24-well Transwell® plate insert with a 0.4 μm-pore semi-permeable polyester membrane was placed into the hu-G-CSF modRNA-transfected keratinocyte containing culture plate. FIG. 5A is a table showing the results from an Enzyme-linked immunosorbent assay (ELISA) for human-G-CSF secreted from in vitro-transfected Human Keratinocyte cells sampled from individual wells in a co-culture 24-well tissue culture plate 42 hours post-transfection with 750 ng of each indicated hu-G-CSF-encoding modRNA.

Human myeloblast cells, Kasumi-1 cells (FIG. 5C) or KG-1 (FIG. 5D) ($0.2\times10^5$ cells), were seeded into the insert well and cell proliferation was quantified 42 hours post-co-culture initiation using the CyQuant Direct Cell Proliferation Assay (Invitrogen) in a 100-120 μl volume in a 96-well plate. modRNA-encoding hu-G-CSF-induced myeloblast cell proliferation was expressed as a percent cell proliferation normalized to untransfected keratinocyte/myeloblast co-culture control wells. Secreted hu-G-CSF concentration in both the keratinocyte and myeloblast insert co-culture wells was measured at 42 hours post-co-culture initiation for each modRNA in duplicate. Secretion of Human Granulocyte-Colony Stimulating Factor (G-CSF) was quantified using an ELISA kit from Invitrogen following the manufacturers recommended instructions.

Transfected hu-G-CSF modRNA in human keratinocyte feeder cells and untransfected human myeloblast cells were detected by RT-PCR. Total RNA from sample cells was extracted and lysed using RNeasy kit (Qiagen, Valencia, CA) according to the manufacturer instructions.

Figure 5B:
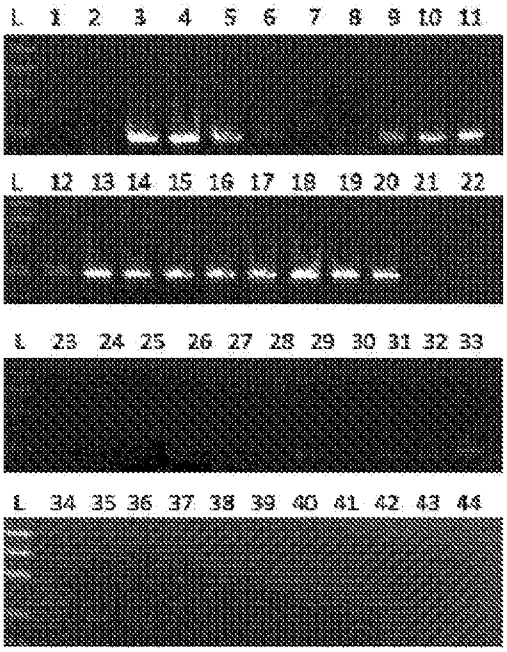
FIG. 5B depicts an image of an agarose gel of RT-PCR hu-G-CSF modRNA products from co-culture cell extracts 42 hours post-transfection of the human keratinocyte feeder layer with hu-G-CSG modRNA and the un-transfected Kasumi-1 and KG-1 insert culture cells.
Figure 5C:
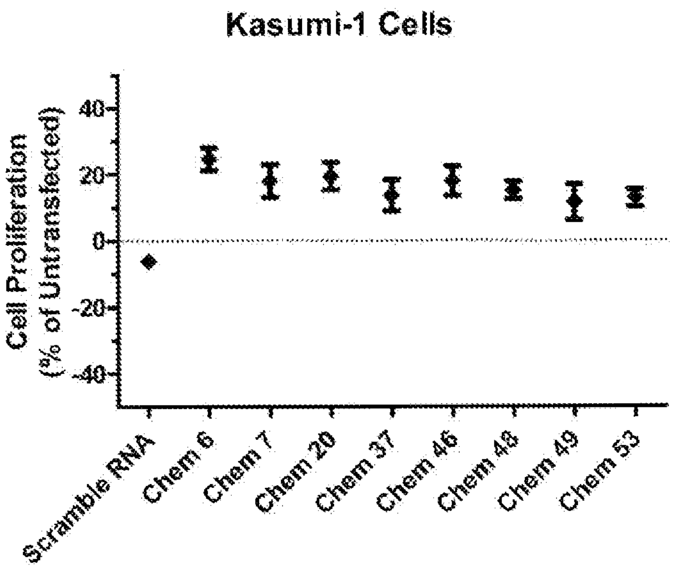
FIGS. 5C and 5D depict graphs of results from a hu-G-CSF-modRNA-induced cell proliferation assay of Kasumi-1 (FIG. 5C) and KG-1 (FIG. 5D) cells normalized to untransfected cells. Hu-G-CSF modRNA identity transfected into human keratinocyte feeder cells is indicated.
Figure 5D:
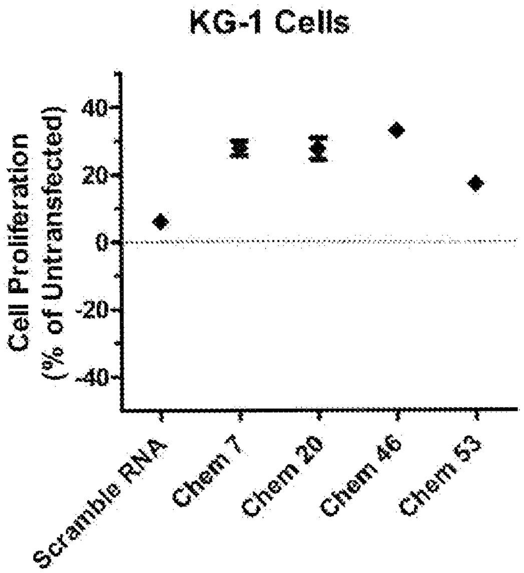
Figure 6A:
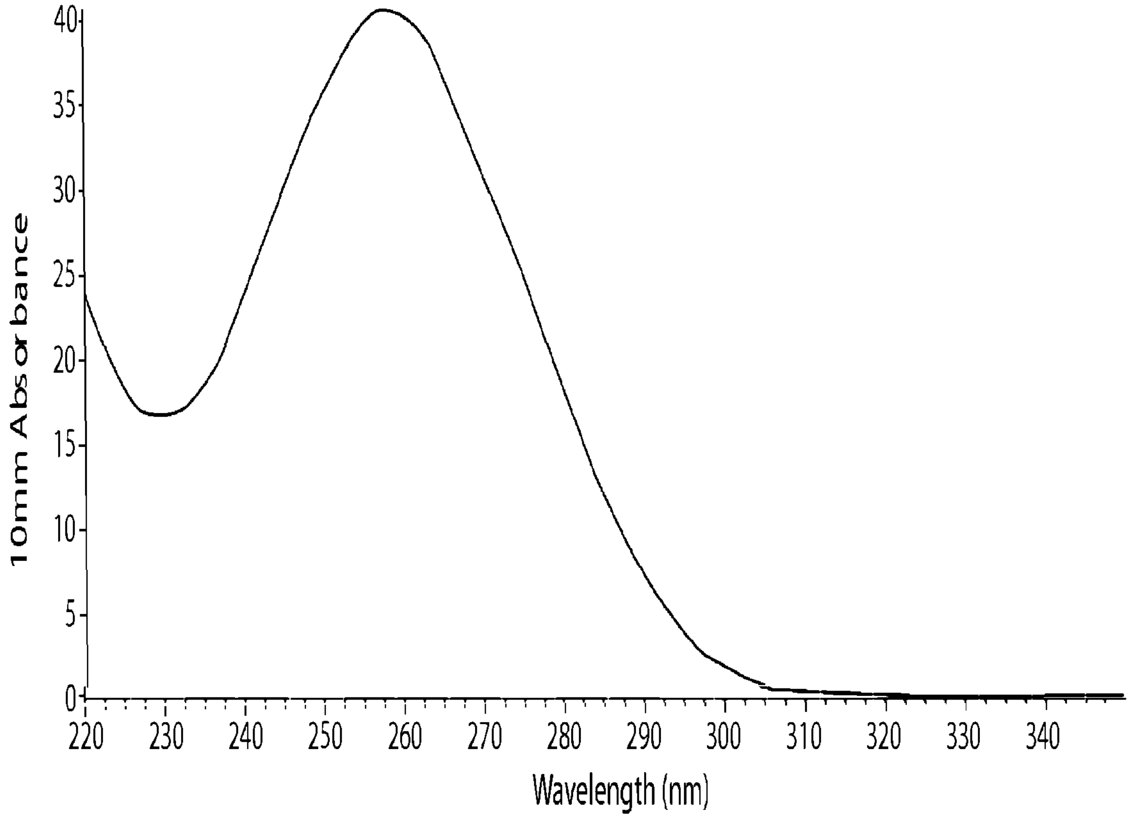
FIGS. 6A-L depict graphs of the UV absorbance spectra for exemplary modRNA molecules that incorporate the indicated modified nucleotide.
Figure 6B:
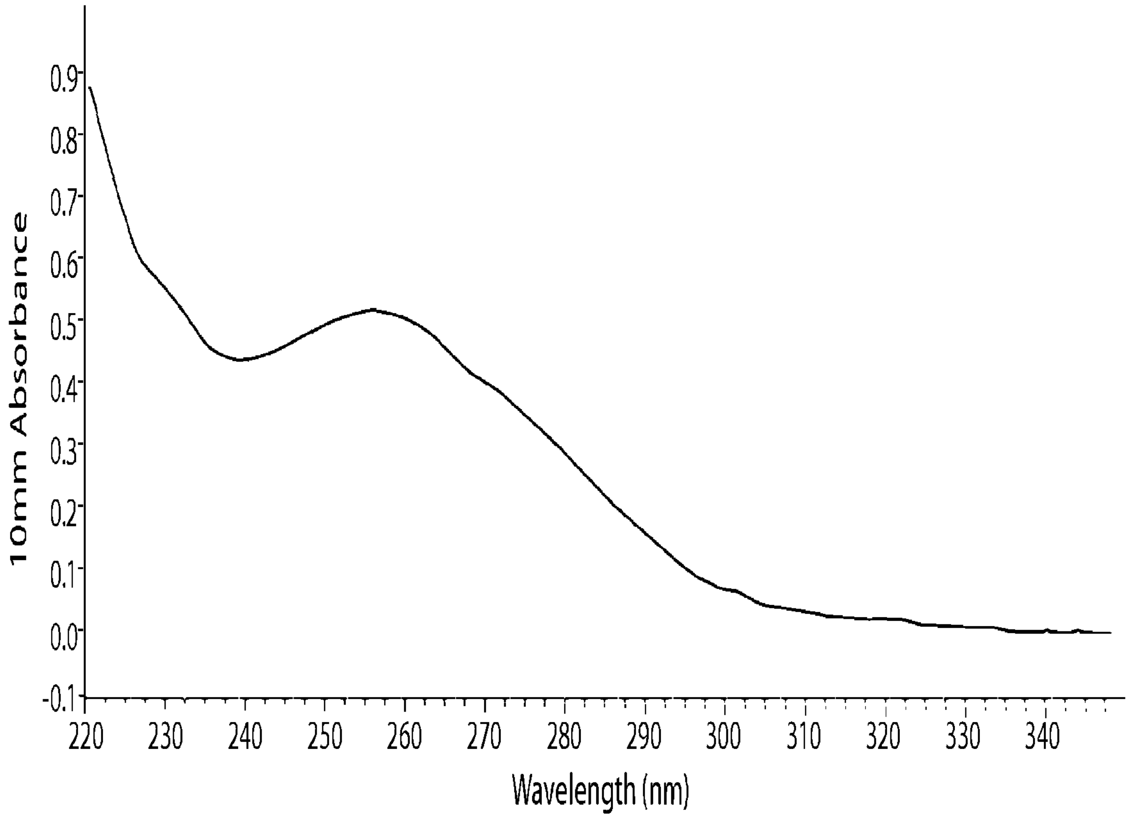
Figure 6C:
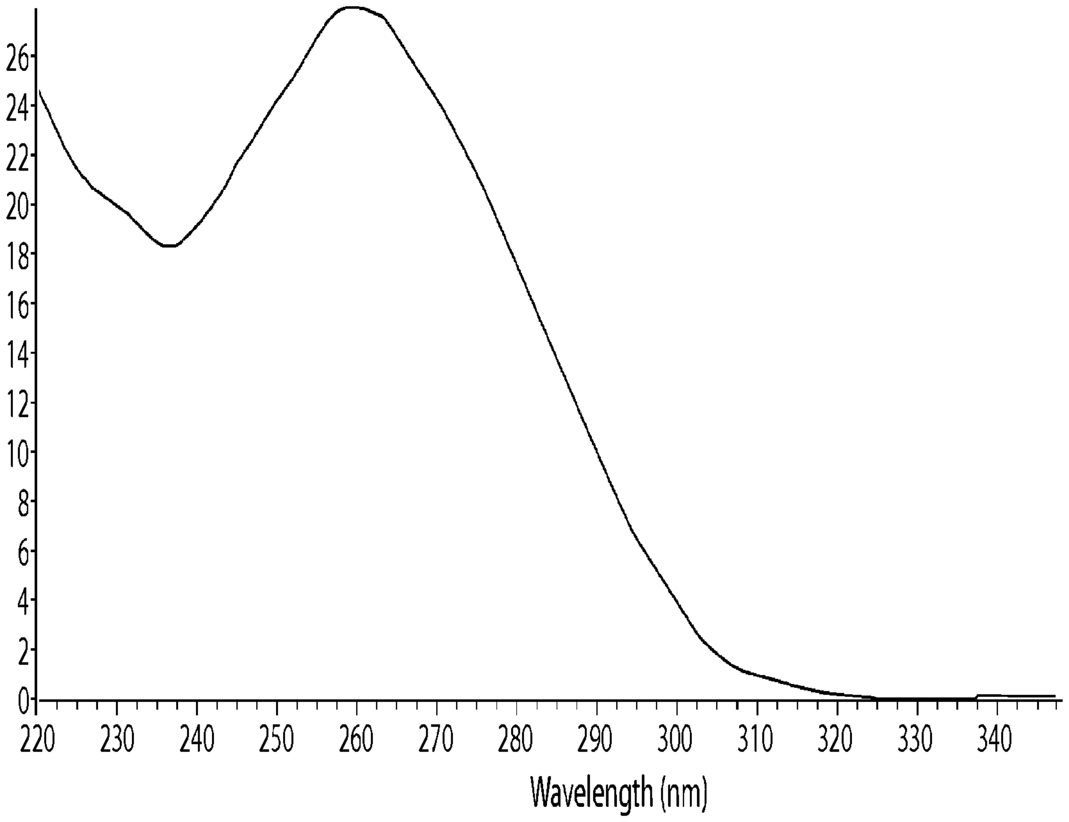
Figure 6D:
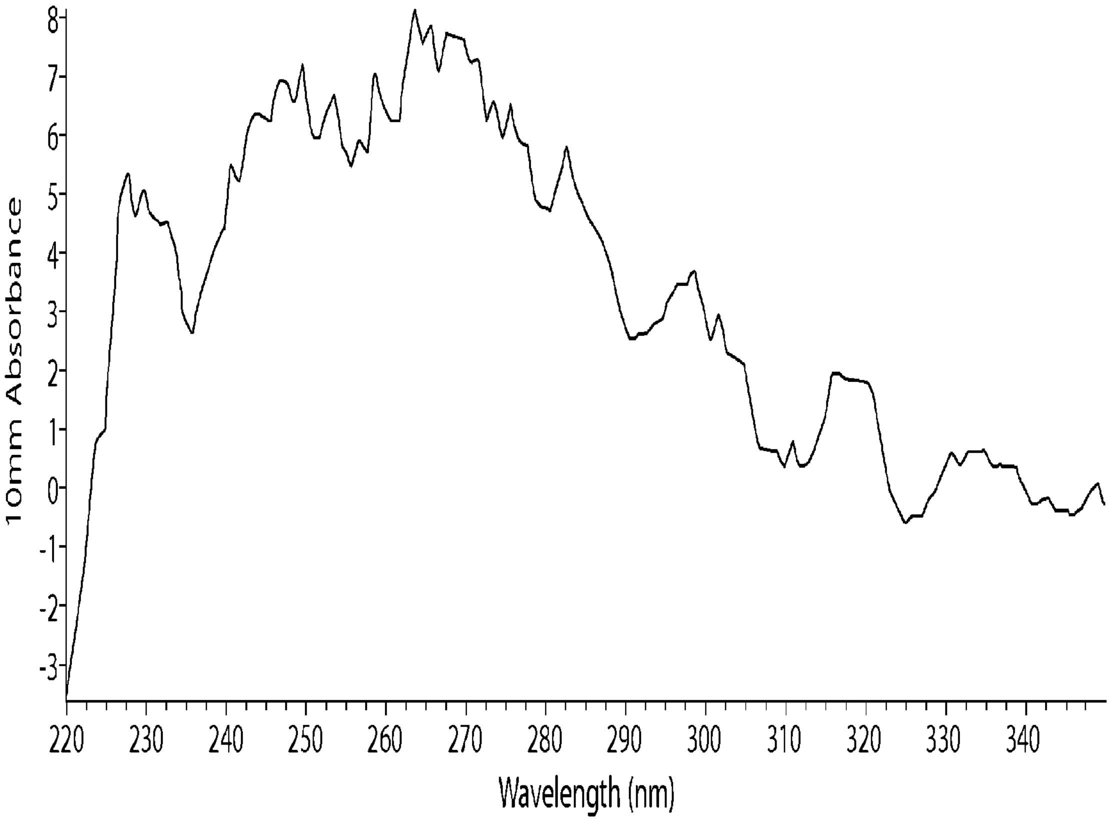
Figure 6E:
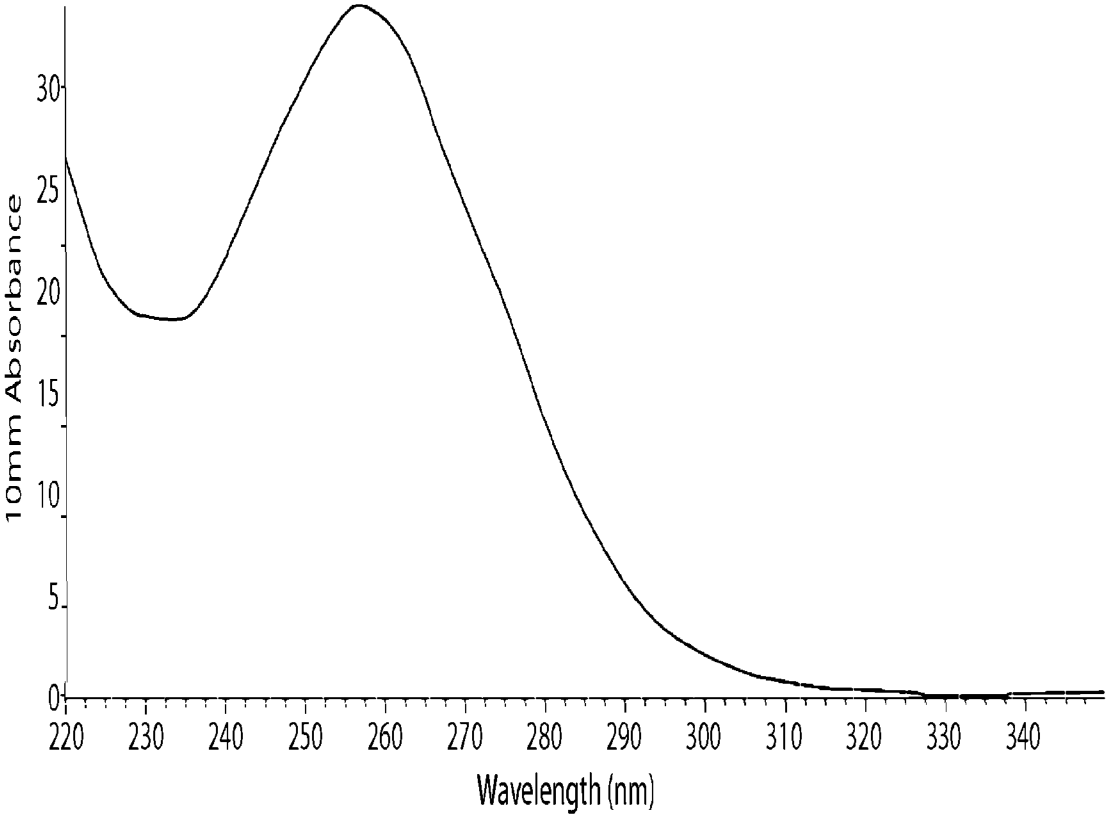
Figure 6F:
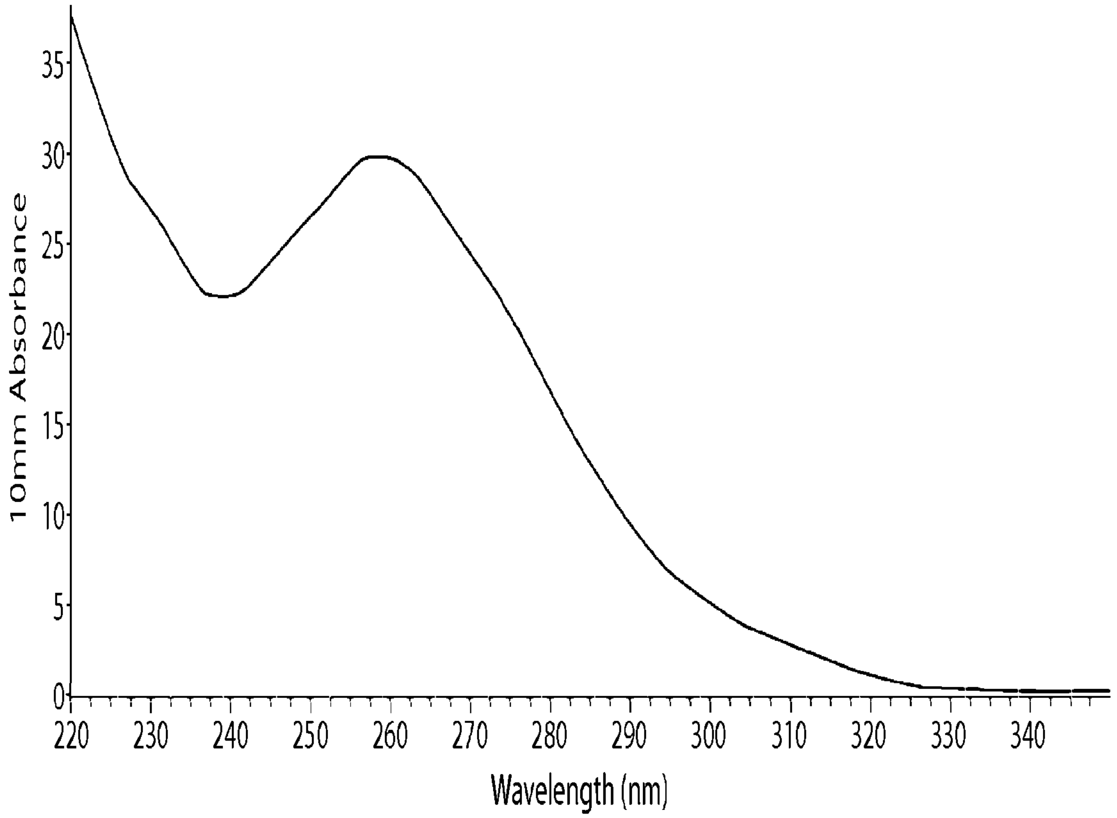
Figure 6G:
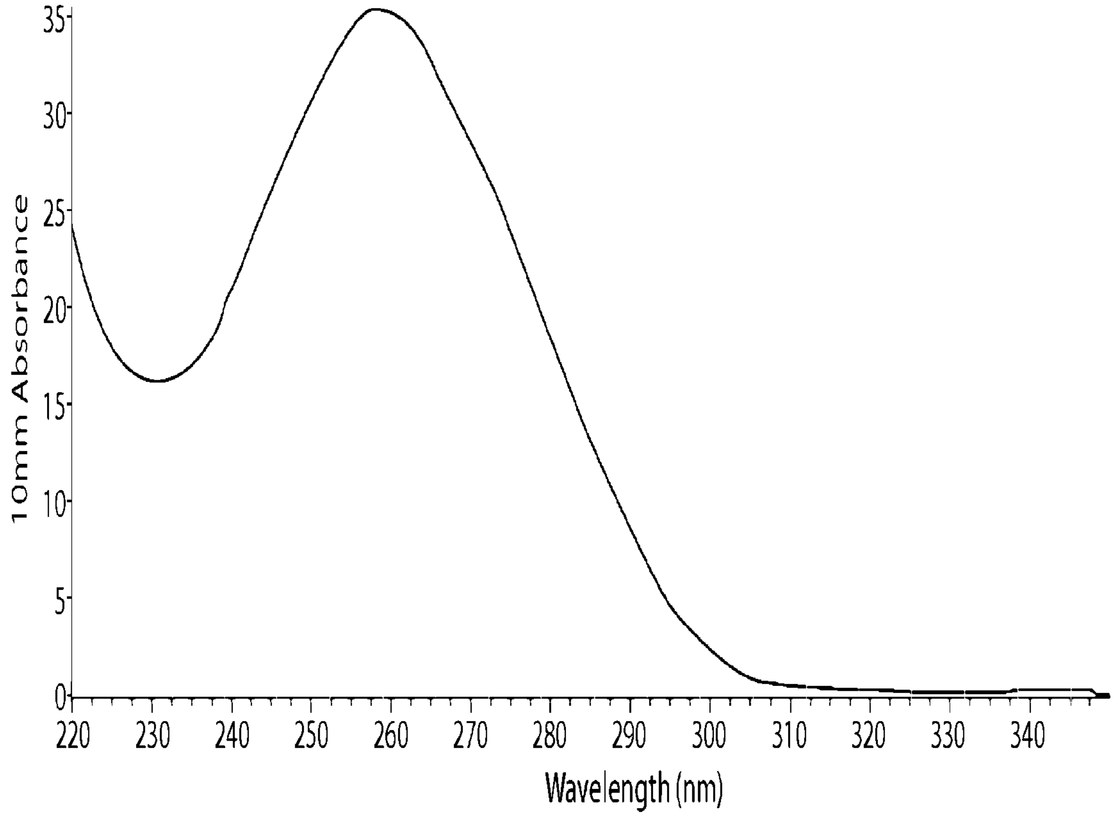
Figure 6H:
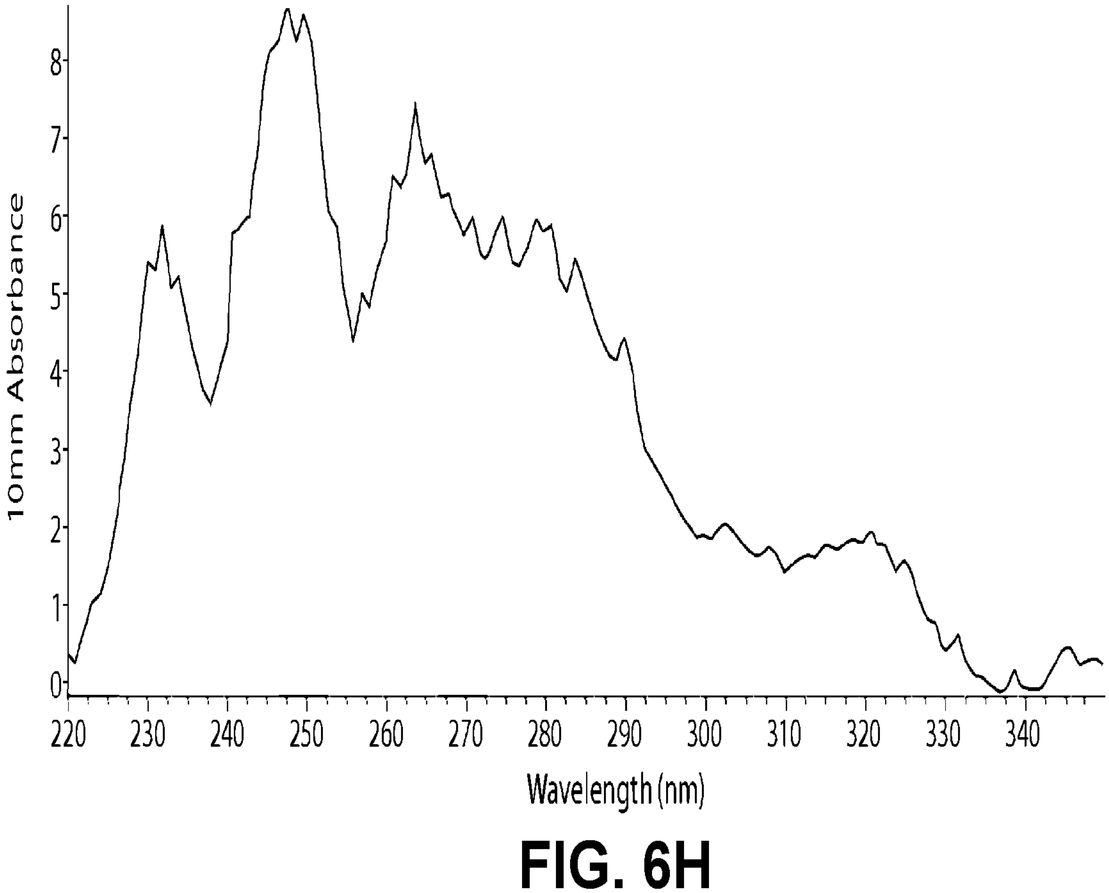
Figure 6I:
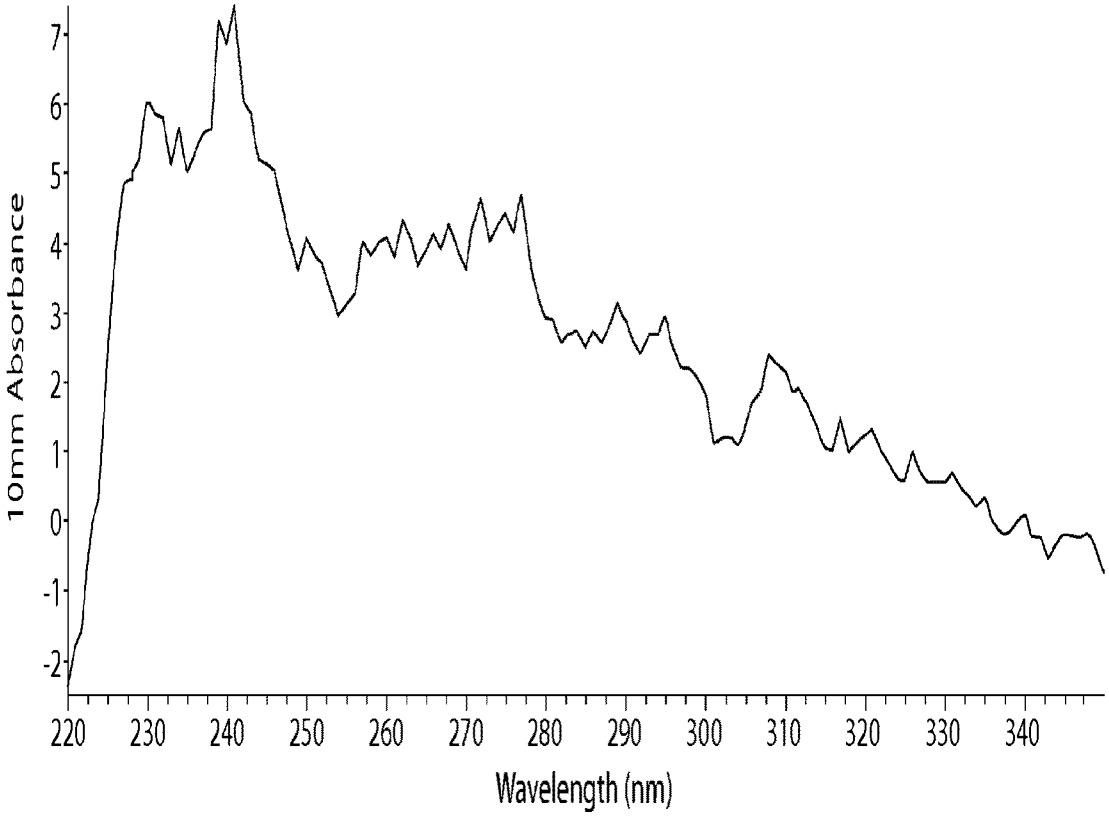
Figure 6J:
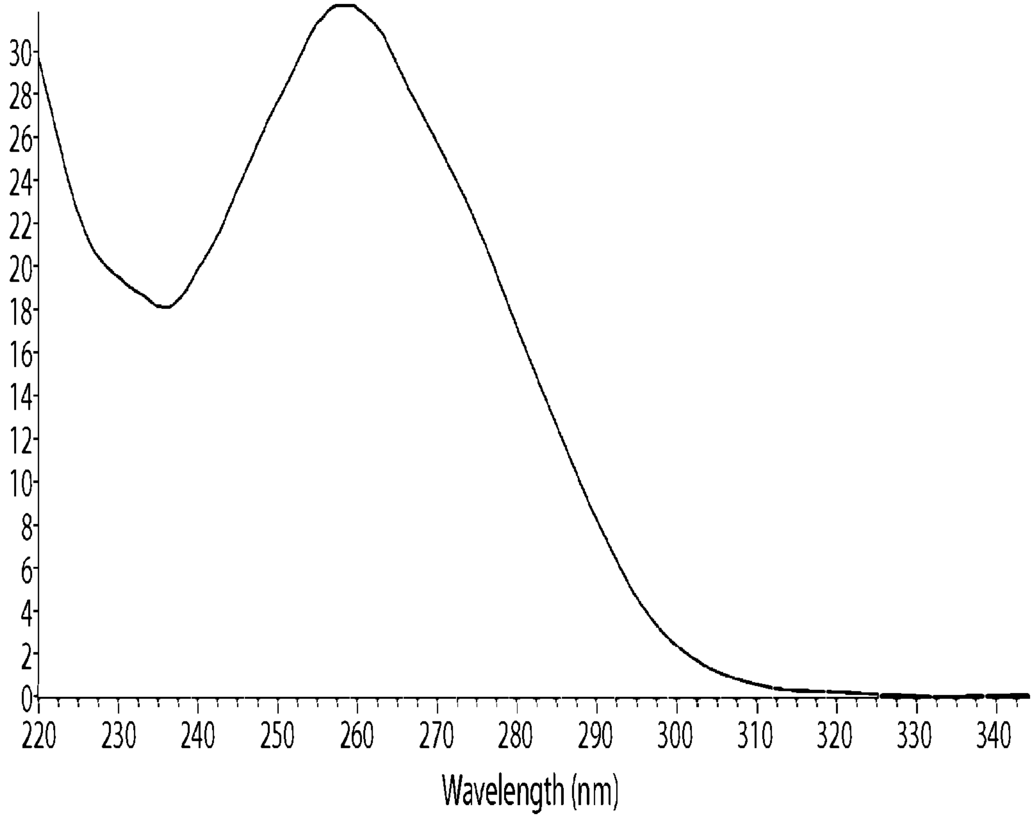
Figure 6K:
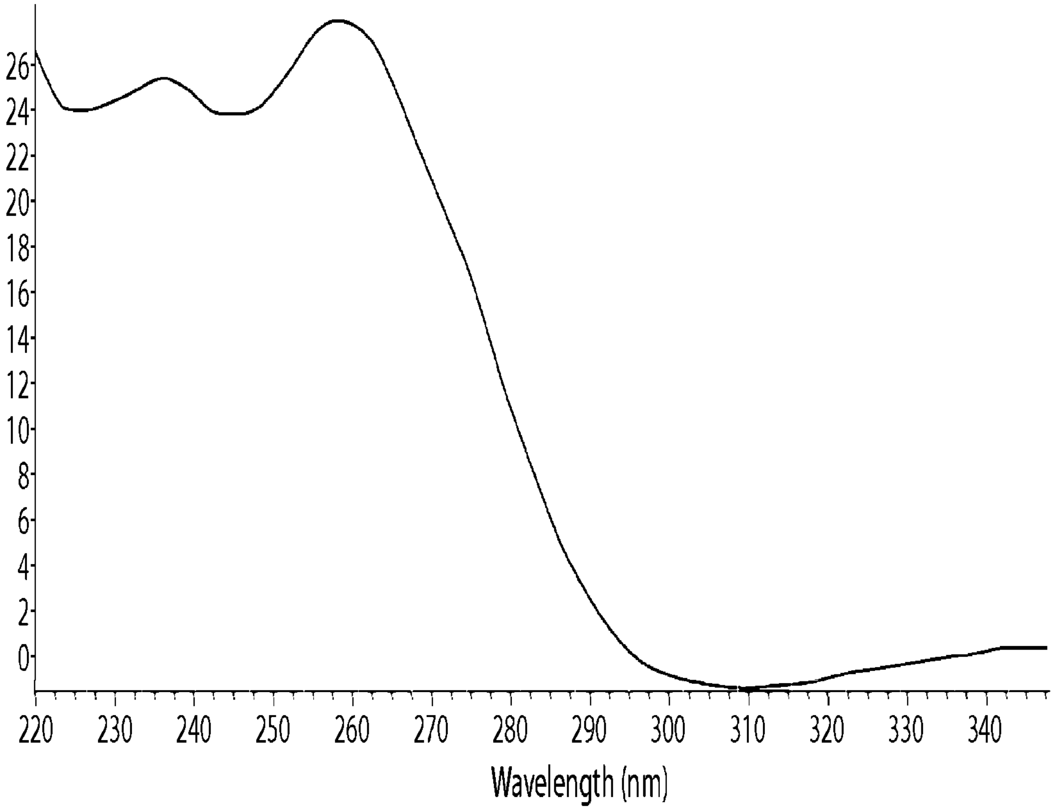
Figure 6L:
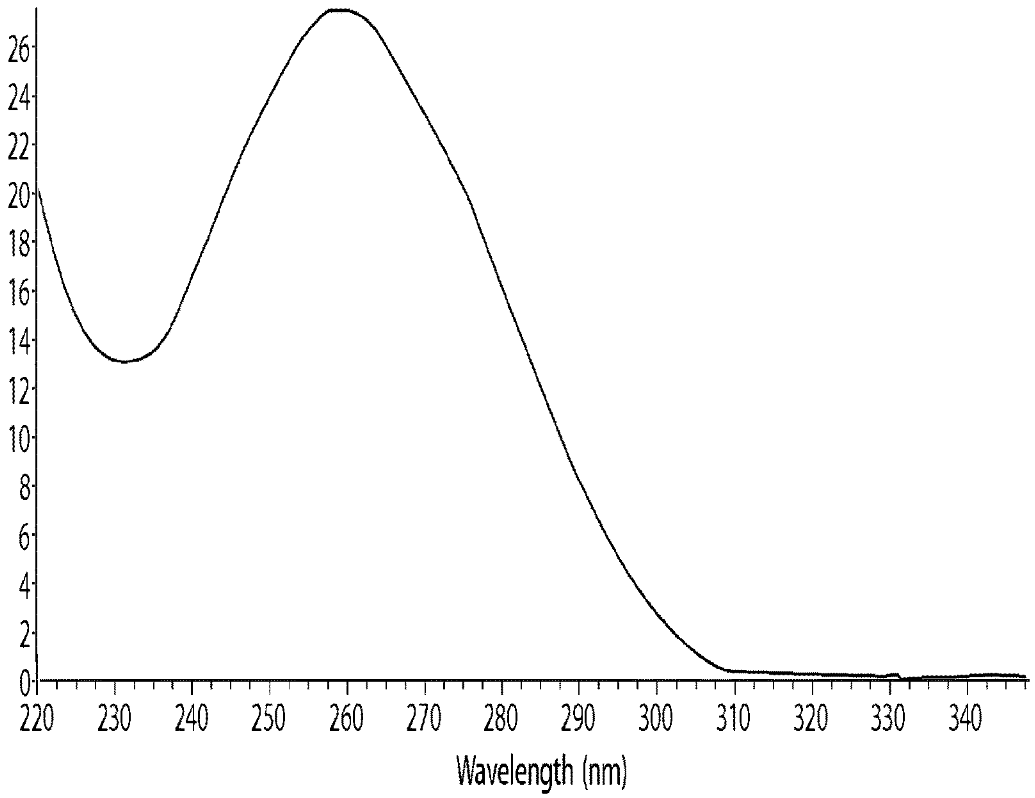

Extracted total RNA was submitted to RT-PCR for specific amplification of modRNA-G-CSF using ProtoScript® M-MuLV Taq RT-PCR kit (New England BioLabs, Ipswich, MA) according to the manufacturer instructions with hu-G-CSF-specific primers (see below). RT-PCR products were visualized by 1.2% agarose gel electrophoresis (FIG. 5B). Table 6 below shows which modRNAs were run on the agarose gel.

TABLE 6

| Lane | Cell type | RT-PCR hu-G-CSF modRNA Target |
|---|---|---|
| 1 | Keratinocyte KG-1 Feeder | Vehicle |
| 2 | Keratinocyte KG-1 Feeder | Scramble RNA |
| 3 | Keratinocyte KG-1 Feeder | No Modification |
| 4 | Keratinocyte KG-1 Feeder | Chem 7 |
| 5 | Keratinocyte KG-1 Feeder | Chem 6 |
| 6 | Keratinocyte KG-1 Feeder | Chem 37 |
| 7 | Keratinocyte Kasumi-1 Feeder | Vehicle |
| 8 | Keratinocyte Kasumi-1 Feeder | Scramble RNA |
| 9 | Keratinocyte Kasumi-1 Feeder | No Modification |
| 10 | Keratinocyte Kasumi-1 Feeder | Chem 7 |
| 11 | Keratinocyte Kasumi-1 Feeder | Chem 6 |
| 12 | Keratinocyte Kasumi-1 Feeder | Chem 37 |
| 13 | Keratinocyte KG-1 Feeder | Chem 46 |
| 14 | Keratinocyte KG-1 Feeder | Chem 48 |
| 15 | Keratinocyte KG-1 Feeder | Chem 49 |
| 16 | Keratinocyte KG-1 Feeder | Chem 53 |
| 17 | Keratinocyte Kasumi-1 Feeder | Chem 46 |
| 18 | Keratinocyte Kasumi-1 Feeder | Chem 48 |
| 19 | Keratinocyte Kasumi-1 Feeder | Chem 49 |
| 20 | Keratinocyte Kasumi-1 Feeder | Chem 53 |
| 21 | Kasumi-1 | Vehicle |
| 22 | KG-1 | Vehicle |
| 23 | Kasumi-1 | Vehicle |
| 24 | Kasumi-1 | Scramble RNA |
| 25 | Kasumi-1 | No Modification |
| 26 | Kasumi-1 | Chem 7 |
| 27 | Kasumi-1 | Chem 6 |
| 28 | Kasumi-1 | Chem 37 |
| 29 | Kasumi-1 | Chem 46 |
| 30 | Kasumi-1 | Chem 48 |
| 31 | Kasumi-1 | Chem 49 |
| 32 | Kasumi-1 | Chem 53 |
| 33 | KG-1 | Vehicle |
| 34 | KG-1 | Scramble RNA |
| 35 | KG-1 | No Modification |
| 36 | KG-1 | Chem 7 |
| 37 | Empty | Empty |
| 38 | Empty | Empty |
| 39 | Empty | Empty |
| 40 | Empty | Empty |
| 41 | Empty | Empty |
| 42 | Empty | Empty |
| 43 | Empty | Empty |
| 44 | Empty | Empty |

These data show that human keratinocyte cells containing hu-G-CSF modRNAs comprised of chemically distinct nucleotide analogs secreted hu-G-CSF protein and that the secreted hu-G-CSF was physiologically-active in inducing the proliferation of human myeloblast cells expressing the G-CSF receptor. These data also show the secreted hu-G-CSF protein was permeable across a semi-permeable membrane and acted on a different non-G-CSF-producing cell population. Additionally, these data show that hu-G-CSF modRNA-transfected into human keratinocyte cells in a co-culture environment was present in only the transfected keratinocyte cells and not the un-transfected myeloblast cells. Further, these data show that the modified nucleotide chemical composition of hu-G-CSF modRNA did not affect resultant protein activity.

Example 5

The Effect of modRNA on Cellular Viability

Cytotoxicity and Apoptosis:

This experiment demonstrates cellular viability, cytotoxity and apoptosis for distinct modRNA-in vitro transfected Human Keratinocyte cells. Keratinocytes are grown in EpiLife medium with Human Keratinocyte Growth Supplement in the absence of hydrocortisone from Invitrogen at a confluence of >70%. Keratinocytes are reverse transfected with 0 ng, 46.875 ng, 93.75 ng, 187.5 ng, 375 ng, 750 ng, 1500 ng, 3000 ng, or 6000 ng of modRNA complexed with RNAiMAX from Invitrogen. The modRNA:RNAiMAX complex is formed. Secreted huG-CSF concentration in the culture medium is measured at 0, 6, 12, 24, and 48 hours post-transfection for each concentration of each modRNA in triplicate. Secretion of Human Granulocyte-Colony Stimulating Factor (G-CSF) from transfected human keratinocytes is quantified using an ELISA kit from Invitrogen or R&D Systems following the manufacturers recommended instructions. Cellular viability, cytotoxicity and apoptosis is measured at 0, 12, 48, 96, and 192 hours post-transfection using the ApoToxGlo kit from Promega (Madison, WI) according to manufacturer instructions.

Example 6

Co-culture

The modified mRNA comprised of chemically-distinct modified nucleotides encoding human Granulocyte-Colony Stimulating Factor (G-CSF) may stimulate the cellular proliferation of a transfection incompetent cell in co-culture environment. The co-culture includes a highly transfectable cell type such as a human keratinocyte and a transfection incompetent cell type such as a white blood cell (WBC). The modified mRNA encoding G-CSF may be transfected into the highly transfectable cell allowing for the production and secretion of G-CSF protein into the extracellular environment where G-CSF acts in a paracrine-like manner to stimulate the white blood cell expressing the G-CSF receptor to proliferate. The expanded WBC population may be used to treat immune-compromised patients or partially reconstitute the WBC population of an immunosuppressed patient and thus reduce the risk of opportunistic infections.

Another example, a highly transfectable cell such as a fibroblast may be transfected with certain growth factors to support and simulate the growth, maintenance, or differentiation of poorly transfectable embryonic stem cells or induced pluripotent stem cells.

Example 7

5'-Guanosine Capping on Modified Nucleic Acids (modRNAs)

The cloning, gene synthesis and vector sequencing was performed by DNA2.0 Inc. (Menlo Park, CA). Sequence and insert sequence are set forth herein. The ORF was restriction digested using XbaI and used for cDNA synthesis using tailed-or tail-less-PCR. The tailed-PCR cDNA product was used as the template for the modified mRNA synthesis reaction using 25 mM mixture each modified nucleotide (all modified nucleotides were custom synthesized or purchased from TriLink Biotech, San Diego, CA except pyrrolo-C triphosphate purchased from Glen Research, Sterling VA; unmodifed nucleotides were purchased from Epicenter Biotechnologies, Madison, WI) and CellScript MegaScript™ (Epicenter Biotechnologies, Madison, WI) complete mRNA synthesis kit. The in vitro transcription reaction was run for 4 hours at 37° C. modRNAs incorporating adenosine analogs were poly (A) tailed using yeast Poly (A) Polymerase (Affymetrix, Santa Clara, CA). PCR reaction used HiFi PCR2× Master Mix™ (Kapa Biosystems, Woburn, MA). modRNAs were post-transcriptionally capped using recombinant Vaccinia Virus Capping Enzyme (New England BioLabs, Ipswich, MA) and a recombinant 2'-O-methyltransferase (Epicenter Biotechnologies, Madison, WI) to generate the 5'-guanosine Cap1 structure. Cap 2 structure and Cap 3 structures may be generated using additional 2'-O-methyltransferases. The in vitro transcribed mRNA product was run on an agarose gel and visualized. modRNA was purified with Ambion/Applied Biosystems (Austin, TX) MEGAClear RNA™ purification kit. PCR used PureLink™ PCR purification kit (Invitrogen, Carlsbad, CA). The product was quantified on Nanodrop™ UV Absorbance (ThermoFisher, Waltham, MA). Quality, UV absorbance quality and visualization of the product was performed on an 1.2% agarose gel. The product was resuspended in TE buffer.

5' Capping Modified Nucleic Acid (mRNA) Structure:

5'-modRNA capping may be completed concomitantly during the in vitro-transcription reaction using the following chemical RNA cap analogs to generate the 5'-guanosine cap structure according to manufacturer protocols: 3"-O-Me-$m^7$G(5')ppp(5')G; G(5')ppp(5')A; G(5')ppp(5')G; $m^7$G(5')ppp(5')A; $m^7$G(5')ppp(5')G (New England BioLabs, Ipswich, MA). 5'-modRNA capping may be completed post-transcriptionally using a Vaccinia Virus Capping Enzyme to generate the "Cap 0" structure: $m^7$G(5')ppp(5')G (New England BioLabs, Ipswich, MA). Cap 1 structure may be generated using both Vaccinia Virus Capping Enzyme and a 2'-O methyl-transferase to generate: m7G(5')ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-O methyl-transferase. Enzymes are preferably derived from a recombinant source.

```
Sequences:
G-CSF cDNA:
                                        (SEQ ID NO: 1)
agcttttggaccctcgtacagaagctaatacgactcacta

tagggaaataagagagaaaagaagagtaagaagaaatata

agagccaccatggccggtcccgcgacccaaagccccatga

aacttatggccctgcagttgctgctttggcactcggccct

ctggacagtccaagaagcgactcctctcggacctgcctca

tcgttgccgcagtcattccttttgaagtgtctggagcagg

tgcgaaagattcagggcgatggagccgcactccaagagaa
```

-continued

```
gctctgcgcgacatacaaactttgccatcccgaggagctc

gtactgctcgggcacagcttggggattccctgggctcctc

tctcgtcctgtccgtcgcaggctttgcagttggcagggtg

cctttcccagctccactccggtttgttcttgtatcaggga

ctgctgcaagcccttgagggaatctcgccagaattgggcc

cgacgctggacacgttgcagctcgacgtggcggatttcgc

aacaaccatctggcagcagatggaggaactggggatggca

cccgcgctgcagcccacgcaggggggcaatgccggcctttg

cgtccgcgtttcagcgcagggcgggtggagtcctcgtagc

gagccaccttcaatcattttggaagtctcgtaccgggtg

ctgagacatcttgcgcagccgtgaagcgctgccttctgcg

gggcttgccttctggccatgcccttcttctctcccttgca

cctgtacctcttggtctttgaataaagcctgagtaggaag

gcggccgctcgagcatgcatctagagggcccaattcgccc

tattcgaagtcg
```

G-CSF mRNA:

(SEQ ID NO: 2)

```
agcuuuuggacccucguacagaagcuaauacgacucacua

uagggaaauaagagagaaaagaagaguaagaagaaauaua

agagccaccauggccggucccgcgacccaaagccccauga

aacuuauggcccugcaguugcugcuuuggcacucggcccu

cuggacaguccaagaagcgacucccucucggaccugccuca

ucguugccgcagucauuccuuuugaagugucuggagcagg

ugcgaaagauucagggcgauggagccgcacuccaagagaa

gcucugcgcgacauacaaacuuugccaucccgaggagcuc

guacugcucgggcacagcuuggggauucccugggcuccuc

ucucguccuguccgucgcaggcuuugcaguugggggggcuu

uccagcuccacuccgguuuguucuuguaucagggacugcu

gcaagcccuugagggaaucucgccagaauugggcccgacg

cuggacacguugcagcucgacguggcggauuucgcaacaa

ccaucuggcagcagauggaggaacuggggauggcacccgc

gcugcagcccacgcagggggcaaugccggccuuugcgucc

gcguuucagcgcaggggggguggaguccucguagcgagcca
```

-continued

```
ccuucaaucauuuuuggaagucucguaccgggugcugaga

caucuugcgcagccgugaagcgcugccuucugggggcuug

ccuucuggccaugcccuucuucucucccuugcaccuguac

cucuuggucuuugaauaaagccugaguaggaaggggccgc

ucgagcaugcaucuagagggcccaauucgcccuauucgaa

gucg
```

G-CSF protein:

(SEQ ID NO: 3)

```
MAGPATQSPMKLMALQLLLWHSALWTVQEATPLGPASSLP

QSFLLKCLEQVRKIQGDGAALQEKLVSECATYKLCHPEEL

VLLGHSLGIPWAPLSSCPSQALQLAGCLSQLHSGLFLYQ

GLLQALEGISPELGPTLDTLQLDVADFATTIWQQMEELGM

APALQPTQGAMPAFASAFQRRAGGVLVASHLQSFLEVSYR

VLRHLAQP
```

cDNA synthesis primers:
Forward Primer:

(SEQ ID NO: 4)

5'-TTG GAC CCT CGT ACA GAA GCT AAT ACG

Reverse Primer for template Poly (A) tailing:

(SEQ ID NO: 5)

5'-T$_{(120)}$CT TCC TAC TCA GGC TTT

ATT CAA AGA CCA

Reverse Primer for post-transcriptional Poly (A) Polymerase tailing:

(SEQ ID NO: 6)

5'-CTT CCT ACT CAG GCT TTA

TTC AAA GAC CA

G-CSF modRNA RT-PCR primers:
Forward Primer:

(SEQ ID NO: 7)

5'-TGG CCG GTC CCG CGA CCC AA

Reverse Primer:

(SEQ ID NO: 8)

5'-GCT TCA CGG CTG CGC AAG AT

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method of synthesizing a messenger ribonucleic acid (mRNA), comprising the steps of:

a) providing a deoxyribonucleic acid (DNA) that encodes a protein of interest;

b) selecting a nucleotide that disrupts a binding of a major groove binding partner with the RNA, wherein the nucleotide has decreased binding affinity to the major groove binding partner selected from the group consisting of toll-like receptor (TLR) 3, TLR7, TLR8, retinoic acid-inducible gene I (RIG-I), melanoma differentiation-associated gene 5 (MDA5) and laboratory of genetics and physiology 2 (LGP2), and wherein the nucleotide comprises a modification on the major groove face of the nucleobase where an atom of the major groove face of the nucleobase is replaced or substituted with a $C_1$-$C_6$ alkyl group; and c) contacting the provided DNA and the selected nucleotide with an RNA polymerase, under conditions such that the mRNA is synthesized.

* * * * *

SEQUENCE LISTING

```
Sequence total quantity: 8
SEQ ID NO: 1           moltype = DNA  length = 852
FEATURE                Location/Qualifiers
source                 1..852
                       mol_type = other DNA
                       note = Description of Artificial Sequence: Synthetic
                        polynucleotide
                       organism = synthetic construct
SEQUENCE: 1
agcttttgga ccctcgtaca gaagctaata cgactcacta tagggaaata agagagaaaa  60
```

-continued

```
gaagagtaag aagaaatata agagccacca tggccggtcc cgcgacccaa agccccatga  120
aacttatggc cctgcagttg ctgctttggc actcggccct ctggacagtc caagaagcga  180
ctcctctcgg acctgcctca tcgttgccgc agtcattcct tttgaagtgt ctggagcagg  240
tgcgaaagat tcagggcgat ggagccgcac tccaagagaa gctctgcgcg acatacaaac  300
tttgccatcc cgaggagctc gtactgctcg ggcacagctt ggggattccc tgggctcctc  360
tctcgtcctg tccgtcgcag gctttgcagt tggcagggtg cctttcccag ctccactccg  420
gtttgttctt gtatcaggga ctgctgcaag cccttgaggg aatctcgcca gaattgggcc  480
cgacgctgga cacgttgcag ctcgacgtgg cggatttcgc aacaaccatc tggcagcaga  540
tggaggaact ggggatggca cccgcgctgc agcccacgca gggggcaatg ccggcctttg  600
cgtccgcgtt tcagcgcagg gcgggtggag tcctcgtagc gagccacctt caatcatttt  660
tggaagtctc gtaccgggtg ctgagacatc ttgcgcagcc gtgaagcgct gccttctgcg  720
gggcttgcct tctggccatg cccttcttct ctcccttgca cctgtacctc ttggtctttg  780
aataaagcct gagtaggaag gcggccgctc gagcatgcat ctagagggcc caattcgccc  840
tattcgaagt cg                                                      852

SEQ ID NO: 2            moltype = RNA  length = 852
FEATURE                 Location/Qualifiers
source                  1..852
                        mol_type = other RNA
                        note = Description of Artificial Sequence: Synthetic
                         polynucleotide
                        organism = synthetic construct
SEQUENCE: 2
agcttttgga ccctcgtaca gaagctaata cgactcacta tagggaaata agagagaaaa  60
gaagagtaag aagaaatata agagccacca tggccggtcc cgcgacccaa agccccatga  120
aacttatggc cctgcagttg ctgctttggc actcggccct ctggacagtc caagaagcga  180
ctcctctcgg acctgcctca tcgttgccgc agtcattcct tttgaagtgt ctggagcagg  240
tgcgaaagat tcagggcgat ggagccgcac tccaagagaa gctctgcgcg acatacaaac  300
tttgccatcc cgaggagctc gtactgctcg ggcacagctt ggggattccc tgggctcctc  360
tctcgtcctg tccgtcgcag gctttgcagt tggcagggtg cctttcccag ctccactccg  420
gtttgttctt gtatcaggga ctgctgcaag cccttgaggg aatctcgcca gaattgggcc  480
cgacgctgga cacgttgcag ctcgacgtgg cggatttcgc aacaaccatc tggcagcaga  540
tggaggaact ggggatggca cccgcgctgc agcccacgca gggggcaatg ccggcctttg  600
cgtccgcgtt tcagcgcagg gcgggtggag tcctcgtagc gagccacctt caatcatttt  660
tggaagtctc gtaccgggtg ctgagacatc ttgcgcagcc gtgaagcgct gccttctgcg  720
gggcttgcct tctggccatg cccttcttct ctcccttgca cctgtacctc ttggtctttg  780
aataaagcct gagtaggaag gcggccgctc gagcatgcat ctagagggcc caattcgccc  840
tattcgaagt cg                                                      852

SEQ ID NO: 3            moltype = AA  length = 207
FEATURE                 Location/Qualifiers
source                  1..207
                        mol_type = protein
                        note = Description of Artificial Sequence: Synthetic
                         polypeptide
                        organism = synthetic construct
SEQUENCE: 3
MAGPATQSPM KLMALQLLLW HSALWTVQEA TPLGPASSLP QSFLLKCLEQ VRKIQGDGAA  60
LQEKLVSECA TYKLCHPEEL VLLGHSLGIP WAPLSSCPSQ ALQLAGCLSQ LHSGLFLYQG  120
LLQALEGISP ELGPTLDTLQ LDVADFATTI WQQMEELGMA PALQPTQGAM PAFASAFQRR  180
AGGVLVASHL QSFLEVSYRV LRHLAQP                                      207

SEQ ID NO: 4            moltype = DNA  length = 27
FEATURE                 Location/Qualifiers
source                  1..27
                        mol_type = other DNA
                        note = Description of Artificial Sequence: Synthetic primer
                        organism = synthetic construct
SEQUENCE: 4
ttggaccctc gtacagaagc taatacg                                      27

SEQ ID NO: 5            moltype = DNA  length = 149
FEATURE                 Location/Qualifiers
source                  1..149
                        mol_type = other DNA
                        note = Description of Artificial Sequence: Synthetic primer
                        organism = synthetic construct
SEQUENCE: 5
tttttttttt tttttttttt tttttttttt tttttttttt tttttttttt tttttttttt  60
tttttttttt tttttttttt tttttttttt tttttttttt tttttttttt tttttttttt  120
cttcctactc aggctttatt caaagacca                                    149

SEQ ID NO: 6            moltype = DNA  length = 29
FEATURE                 Location/Qualifiers
source                  1..29
                        mol_type = other DNA
                        note = Description of Artificial Sequence: Synthetic primer
                        organism = synthetic construct
SEQUENCE: 6
```

-continued

```
cttcctactc aggctttatt caaagacca                                     29

SEQ ID NO: 7           moltype = DNA  length = 20
FEATURE                Location/Qualifiers
source                 1..20
                       mol_type = other DNA
                       note = Description of Artificial Sequence: Synthetic primer
                       organism = synthetic construct
SEQUENCE: 7
tggccggtcc cgcgacccaa                                               20

SEQ ID NO: 8           moltype = DNA  length = 20
FEATURE                Location/Qualifiers
source                 1..20
                       mol_type = other DNA
                       note = Description of Artificial Sequence: Synthetic primer
                       organism = synthetic construct
SEQUENCE: 8
gcttcacggc tgcgcaagat                                               20
```